(12) United States Patent
Elmaleh et al.

(10) Patent No.: US 7,790,142 B2
(45) Date of Patent: Sep. 7, 2010

(54) METHOD FOR MONITORING BLOOD FLOW AND METABOLIC UPTAKE IN TISSUE WITH RADIOLABELED ALKANOIC ACID

(75) Inventors: David R. Elmaleh, Boston, MA (US); Alan J. Fischman, Boston, MA (US); Timothy M. Shoup, Boston, MA (US)

(73) Assignee: The General Hospital Corporation, Boston, MA (US)

( * ) Notice: Subject to any disclaimer, the term of this patent is extended or adjusted under 35 U.S.C. 154(b) by 290 days.

(21) Appl. No.: 11/974,139

(22) Filed: Oct. 11, 2007

(65) Prior Publication Data
US 2008/0206135 A1 Aug. 28, 2008

Related U.S. Application Data

(62) Division of application No. 10/827,054, filed on Apr. 19, 2004, now Pat. No. 7,494,642.

(60) Provisional application No. 60/463,574, filed on Apr. 17, 2003.

(51) Int. Cl.
*A61K 51/00* (2006.01)
*A61M 36/14* (2006.01)
(52) U.S. Cl. .................. 424/1.89; 424/1.11; 424/1.65; 424/1.81; 424/1.85
(58) Field of Classification Search .............. 424/1.11, 424/1.65, 1.75, 1.81, 1.85, 1.89, 9.1, 9.3, 424/9.4, 9.5, 9.6, 9.7, 9.8, 1.49, 1.73
See application file for complete search history.

(56) References Cited

U.S. PATENT DOCUMENTS

| 4,202,902 | A | 5/1980 | Carr et al. |
|---|---|---|---|
| 4,323,547 | A | 4/1982 | Knust et al. |
| 4,524,059 | A | 6/1985 | Elmaleh et al. |
| 6,437,103 | B1 | 8/2002 | Babich et al. |
| 7,005,119 | B2 | 2/2006 | Elmaleh |
| 7,314,609 | B2 | 1/2008 | Elmaleh |
| 7,494,642 | B2 | 2/2009 | Elmaleh et al. |
| 2007/0128110 | A1 | 6/2007 | Elmaleh |
| 2008/0095702 | A1 | 4/2008 | Elmaleh et al. |
| 2008/0213173 | A1 | 9/2008 | Elmaleh et al. |
| 2008/0213178 | A1 | 9/2008 | Elmaleh et al. |
| 2008/0214851 | A1 | 9/2008 | Elmaleh et al. |
| 2008/0214853 | A1 | 9/2008 | Elmaleh et al. |
| 2008/0247948 | A1 | 10/2008 | Elmaleh |
| 2009/0156848 | A1 | 6/2009 | Elmaleh et al. |

FOREIGN PATENT DOCUMENTS

| WO | WO 97/19705 | 6/1997 |
|---|---|---|
| WO | WO 2004/092184 A1 | 10/2004 |

OTHER PUBLICATIONS

Jonas et al (Journal of Nuclear Medicine, 1996, vol. 37, No. 12, pp. 1990-1994).*
Ambrose et al., "Evaluation of the metabolism in rat hearts of two new radioiodinated 3-methyl-branched fatty acid myocardial imaging agents", Eur Jnl Nucl Med (1987), 12:486-491.
Ambrose et al., "Effect of 3-methyl-branching on the metabolism in rat hearts of radioiodinated iodovinyl long chain fatty acids", Eur Jnl Nucl Med (1987) 13:374-379.
De Geeter et al., "Relationship between blood flow and fatty acid metabolism in subacute myocardial infarction: a study by means of $^{99m}$Tc-Sestamibi and $^{123}$I-β-methyl-iodo-phenyl pentadecanoic acid", Eur JnI of Nucl Med, vol. 21, No. 4, (1994).
Degrado et al., "β-Methyl-15-*p*-iodophenylpentadecanoic acid metabolism and kinetics in the isolated rat heart", Eur Jnl Nucl Med (1989), 15:78-80.
Fritzberg et al., "Iodophenylsulfonamide fatty acid analogs as potential myocardial imaging agents", Int Jnl Appl Radiat Isot (1982) 33(6): 451-3.
Fujibayashi et al., "Myocardial accumulation of iodinated beta-methyl-branched fatty acid analog, [125I](p-iodophenyl)-3-(R,S)-methylpentadecanoic acid (BMIPP), and correlation to ATP concentration—II, Studies in salt-induced hypertensive rats", Nucl Med Biol (1993) 20(2): 163-6.

(Continued)

*Primary Examiner*—D L Jones
(74) *Attorney, Agent, or Firm*—Edwards Angell Palmer & Dodge LLP; Peter C. Lauro; Mark D. Russett

(57) ABSTRACT

The present invention relates to novel modified fatty acid analogs, where a positron or gamma-emitting label is placed at a position on a fatty acid backbone and an organic substituent is substituted at the 2,3; 3,4; 4,5; 5,6 and other sequence positions of a fatty acid backbone. These novel fatty acid analogs are designed to enter the tissues of interest by the same long chain fatty acid carrier mechanism as natural fatty acids, however, functional substituents in the 2,3; 3,4; 4,5; 5,6 and other sequence positions, block the catabolic pathway, thus trapping these analogs in a virtually unmodified form in the tissues of interest.

22 Claims, 15 Drawing Sheets

OTHER PUBLICATIONS

Fujibayashi et al., "Basic Studies on I-123-beta-methyl-p-iodophenylpentadecanoic Acid (BMIPP) for Myocardial Functional Diagnosis: Effect of Beta-oxidation Inhibitor".

Hasegawa et al., "Detection of viable myocardium with p-iodophenyl-9-(R,S)-methylpentadecanoic acid in ischemic rat myocardium", Jnl of Nucl Cardiology, (2002) vol. 9, 5:463-70.

Hashimoto et al., "Prediction of left ventricular functional recovery in patients with acute myocardial infarction using single photon emission computed tomography with thallium-201 and iodine-123-beta-methyl-p-iodophenyl-pentadecanoic acid", Jnl Cardiology, (1995) 26(2): 59-68. PubMed English Abstract , 2-pages.

Isobe et al., "The characteristics of myocardial fatty acid metabolism in patients with left ventricular hypertrophy", Kaku Igaku, (1999) 36(7): 725-33, PubMed English Abstract, 2-pages.

Isobe et al., "Usefulness of 201TI/123I-BMIPP myocardial SPECT to evaluate myocardial viability and area at risk in acute myocardial infarction—comparison with 201TI/99mTc-PYP dual SPECT" , Kaku Igaku, (1997) 34(4): 213-20, PubMed English Abstract. 1 page.

Ito et al., "Relation between thallium-201/iodine 123-BMIPP subtraction and fluorine 18 deoxyglucose polar maps in patients with hypertrophic cardiomyopathy", Jnl Nucl Cardiology, (2000), vol. 7, 1;16-22.

Kawamoto et al., "Value of fatty acid imaging using 123I-beta-methyl iodophenyl pentadecanoic acid (BMIPP) to assess viability of infarcted myocardium", Kaku Igaku, (1991), 28(9): 1081-9, PubMed English Abstract, 1 pages.

Kawamura et al., "Evaluation of Branched Chain Fatty Acid, BMIPP [β-methyl-ω-(p-iodophenyl)-pentadecanoic acid] for the Myocardial Imaging—basic experiment", Kaku Igaku (1992) 29(4); 453-61.

Kihara et al., "Clinical study on myocardial imaging with beta-methyl-p-(123I)-iodophenyl-pentadecanoic acid in patients with mitochondrial myopathy", Kaku Igaku, (1992), 29(4):453-61, PubMed English Abstract, 1 pages.

Kim et al., "Detection of impaired fatty acid metabolism in right ventricular hypertrophy: Assessment by I-123 β-methyl iodophenyl pentadecanoic acid (BMIPP) myocardial single-photon emission computed tomography", Annals of Nucl Med, (1997) vol. 11, 3, 207-212.

Knapp et al., "Iodine-123-labelled fatty acids for myocardial single-photon emission tomography: current status and future perspectives", Eur Jnl of Nucl Med, (1995) vol., 22, No. 4, 361-381.

Knapp et al., "New radioiodinated methyl-branched fatty acids for cardiac studies", Eur Jnl of Nucl Med (1986), 12:S39-S44.

Kobayashi et al., "Fatty acid metabolic and perfusion abnormalities in hypertrophied myocardium assessed by dual tracer tomography using thallium-201 and iodine-123-beta-methylpentadecanoic acid", Jnl Cardiology, (1994), 24(1): 35-43, PubMed English Abstract, 2 pages.

Machulla et al., "Biochemical Concept and Synthesis of a Radioiodinated Phenylfatty Acid for in Vivo Metabolic Studies of the Myocardium", Eur Jnl Nucl Med, (1980), 5, 171-173.

Mori et al., "Relationship between ventricular arrythmias and myocardial fatty acid metabolism in patients with coronary heart disease: evaluation using iodine-123 beta-methyl-p-iodophenyl-pentadecanoic acid", Jnl of Cardiology, (1999), 34(2):61-9, PubMed English, Abstract, 2 pages.

Nishimura et al., "Prognosis of hypertrophic cardiomyopathy: Assessment by $^{123}$I-BMIPP (β-methyl-p($^{123}$I)-iodophenyl pentadecanoic acid) myocardial single photon emission computed tomography", Annals of Nucl Med, vol. 10, No. 1, (1996) 71-78.

Nishimura et al., Fatty acid myocardial imaging using $^{123}$I-β-methyl-iodophenyl pentadecanoic acid (BMIPP): comparison of myocardial perfusion and fatty acid utilization in canine myocardial infarction (Occlusion and reperfusion model), Eur Jnl Nucl Med (1989) 15:341-345.

Nishimura et al., "Clinical results with β-methyl-p($^{123}$I)iodophenylpentadecanoic acid, single-photon emission computed tomography in cardiac disease", Jnl of Nucl Cardiology, (1994) vol. 1, No. 2;S65-S71.

Schelbert, H.R., "Positron-emission tomography: assessment of myocardial blood flow and metabolism", Circulation (1985), vol. 72 (suppl IV), IV-122-133.

Schlosser et al., "Fluor-olefine durch Fluormethylenierung von Carbonylverbindugen", Synthesis, 1:75-76.

Schon, et al., "C-11 labeled palmitic acid for the noninvasive evaluation of regional myocardial fatty acid metabolism with positron computed tomography. II. Kinetics of C-11 palmitic acid in acutely ischemic myocardium", 1982, Am Heart Jnl 103:548-561.

Shiotani et al., "Myocardial SPECT with iodine-123-labeled beta-methyl-branched fatty acid in patients with angina pextoris", Kaku Igaku, (1994), 31(11):1343-9, PubMed English Abstract, 1 page.

Shogase et al., "A role of nuclear medicine in diagnosing cardiac disease—clinical use of 123I-BMIPP and 123I-MIBG", Rinsho Byori (2000), 48(2):113-20, PubMed English Abstract, 1 page.

Takahashi et al., "Clinical usefulness of myocardial iodine-123-15-(p-iodophenyl)-3(R,S)-methyl-pentadecanoic acid distribution abnormality in patients with mitochondrial encephalomyopathy based on normal data file in bull's-eye polar map", Jnl. of Cardiology, (1998), 31(1):1-10, PubMed English Abstract, 1 page.

Tamaki et al., "Myocardial imaging using PET and SPECT", Nippon Rinsho (1998), 56(10):2550-5, PubMed English Abstract, 1 page.

Tamaki et al., "Radionuclide assessment of myocardial fatty acid metabolism by PET and SPECT", Jnl of Nucl Cardiology (1995) 2:256-66.

Taniguchi et al., "Separate evaluation of beta-methyl fatty acid uptake and perfusion in rat myocardium", Kaku Igaku, (1989) 26(12):1523-30, PubMed English Abstract, 1 page.

Westera et al., "A Comparison Between Terminally Radioiodinated Hexadecenoic Acid (*I-HA) and $^{201}$TI-Thallium Chloride in the Dog Heart", Eur Jnl Nucl Med, (1980), 5, 339-343.

Corbett. J.R., "Fatty Acids for Myocardial Imaging", [Cardiovascular Nuclear Medicine, Part 1], Seminars in Nuclear Medicine, vol. XXIX, No. 3 (1999) pp. 237-258.

Jonas et al. "Simultaneous Evaluation of Fatty Acid Metabolism and Myocardial Flow in an Explanted Heart" The Journal of Nuclear Medicine 37(12): 1990-1994 (1996).

Eisenhut et al. "Trapping and Metabolism of Radioiodinated PHIPA 3-10 in the Rat Myocardium" The Journal of Nuclear Medicine 38(12): 1864-1869 (1997).

Matsuura et al. "Metabolism of Deuterium-labeled Jasmonic Acid and OPC 8:0 in the potatoe plant (*Solanum tuberosum* L.)" Bioscience, biotechnology and Biochemistry 67( ): 1903-1907 (2003).

Abendschein D.R. et al "Metabolism of beta-methyl[1-11C]heptadecanoic acid in canine myocardium" Int. J. Rad. Appl. Instrum. B (1987) 14(6): 579-85.

Ambrose, K.R. et al. "Evaluation of the metabolism in rat hearts of two new radioiodinated 3-methyl-branched fatty acid myocardial imaging agents" Eur. J. Nucl. Med. (1987) 12(10): 486-91.

Ambrose, K.R. et al. "Effect of 3-methyl-branching on the metabolism in rat hearts of radioiodinated iodovinyl long chain fatty acids" Eur. J. Nucl. Med. (1987) 13(7): 374-9.

Antar, M.A. "Radiopharmaceuticals for studying cardiac metabolism" Int. J. Rad. Appl. Instrum. B. (1990)17(1): 103-28.

Bianco, J.A. et al. "Effect of glucose and insulin infusion on the myocardial extraction of a radioiodinated methyl-substituted fatty acid" 1986, Eur. J. Nucl. Med. 12: 120-4.

Brown, M. et al. "Delineation of myocardial oxygen utilization with carbon-11-labeled acetate" Circulation (1987) 76(3): 687-96.

Caldwell, J.H. et al. "Iodophenylpentadecanoic acid-myocardial blood flow relationship during maximal exercise with coronary occlusion." 1990. J. Nucl. Med. 31: 99-105.

Chien, K.R. et al. "In vivo esterification of a synthetic 125-I labeled fatty acid into cardiac glycerolipids" 1983. Am. J. Physiol. 245: H693-697.

DeGeeter, F. et al. "Relationship between blood flow and fatty acid metabolism in subacute myocardial infarction: a study by means of 99m-Tc-Setamibi and 123I-beta-methyl-iodophenyl pentadecanoic acid" Eur. J. Nucl. Med. (1994) 21(4): 283-91.

DeGrado, T.R. et al. "Quantitative analysis of myocardial kinetics of 15-p-[iodine-125]iodiphenylpentadecanoic acid" J. Nucl. Med. (1989) 30(7): 1211-8.

DeGrado, T.R. et al. "beta-Methyl- 15-p-iodophenylpentadecanoic acid metabolism and kinetics in the isolated rat heart" Eur. J. Nucl. Med. (1989) 15(2): 78-80.

Demaison, L. et al. "Myocardial metabolism of radioiodinated methyl-branched fatty acids" J. Nucl. Med. (1988) 29(7): 1230-6.

Dormehl, I.C. et al. "Planar myocardial imaging in the baboon model with iodine-123-15-(iodophenyl)pentadecanoic acid (IPPA) and iodine-123-15-(p-iodophenyl)-3-R,S-methylpentadecanoic acid (BMIPP) using time-activity curves for evaluation of metabolism" Nucl. Med. Biol. (1995) 22(7): 837-47.

Elmaleh, D.R. et al *inventor is an author* "Myocardial extraction of 1-[11C] betamethylheptadecanoic acid" J. Nucl. Med. (1994) 35 (3): 496-503.

Elmaleh, D.R. et al *this is the inventor* "Comparison of 11 C and 14C-labeled fatty acids and their beta-methyl analogs" Int. J. Nucl. Med. Biol. (1983) 10(4): 181-7.

Elmaleh, D.R. et al. "Myocardial imaging with 9-[Te-123m]telluraheptadecanoic acid" J. Nucl. Med. 22: 994-9.

Fagret, D. et al. "Kinetics of iodomethylated hexadecanoic acid metabolism in the rat myocardium: influence of the number and position of methyl radicals" Int. J. Nucl. Med. Biol. (1985) 12(5): 363-7.

Fagret, D., et al. "Iodomethylated fatty acid metabolism in mice and dogs" Eur. J. Nucl. Med. (1988) 14(12): 624-7.

Fink, G.D. et al. "Metabolism of beta-methyl-heptadecanoic acid in the perfused rat heart and liver" J. Nucl. Med. (1990) 31(11): 1823-30.

Fox, K.A. et al. "Efflux of metabolized and nonmetabolized fatty acid from canine myocardium. Implications for quantifying myocardial metabolism tomographically" (1975) Circ. Res. 57: 232-243.

Freundlieb, C. et al. "Myocardial imaging and metabolic studies with [17-123I]iodoheptadecanoic acid" J. Nucl. Med. 1980 21 11 : 1043-50.

Fujibayashi, Y. et al. "Myocardial accumulation of iodinated beta-methyl-branched fatty acid analog, [125I](p-iodophenyl)-3-(R,S)-methylpentadecanoic acid (BMIPP), and correlation to ATP concentration-II. Studies in salt-induced hypertensive rats" Nucl. Med. Biol. (1993) 20(2): 163-6.

Fujibayashi, Y. et al. "Basic studies on I-123-beta-methyl-p-iodophenylpentadecanoic acid (BMIPP) for myocardial functional diagnosis: effect of beta-oxidation inhibitor".

Fujiwara, S. et al. "Fatty acid imaging with 123I-15-)p-iodophenyl)-9-R,S-methylpentadecanoic acid in acute coronary syndrome" J. Nucl. Med. (1999) 40(12): 1999-2006.

Goldstein, R.A. et al. "External assessment of myocardial metabolism with C-11 palmitate in vivo". 1980. J. Nucl. Med. 21: 342-348.

Goodman, M.M. et al. "Effect of 3-methyl branching on the myocardial retentio of radioiodinated 19-iodo-18-nonadecenoic acid analogues" Int. J. Rad. Appi. Instrum. B. (1989) 16(8): 813-9.

Goodman, M.M. et al. "Design, synthesis, and evaluation of omega-iodovinyl- and omega-iodoalkyl-substituted methyl-branched long chain fatty acids" J. Med. Chem. (1985) 28(6): 807-15.

Goodman, M.M. et al. "Synthesis and evaluation of radioiodinated terminal p-iodophenyl-substituted alpha-and beta-methyl-branched fatty acids" J. Med. Chem. (1984) 27(3): 390-7.

Grover-McKay, M. et al. "Identification of impaired metabolic reserve by atrial pacing in patients with significant coronary artery stenosis" 1986. Circulation 74:281-292.

Hasegawa, S. et al. "Detection of viable myocardium with p-iodophenyl-9-(R,S)-methyleentadecanoic acid in ischemic rat myocardium" J. Nucl. Cardiol. (2002) 9(5): 463-70.

Hashimoto, A. et al. "Prediction of left ventricular functional recovery in patients with acute myocardial infarction using single photon emission computed tomography with thallium-201 and iodine 123-beta-methyl-p-iodophenyl-pentadecanoic acid" J. Cardiol. (1995) 26(2): 59-68, (English abstract).

Hashimoto, J. et al. "Scintigraphic evaluation of myocardial ischaemia using a new fatty acid analogue: iodine-123-labelled 15-(p-iodophenyl)-9-(R,S)-methylpentadecanoic acid (9MPA)" Eur J Nucl. Med. (1999) 26(8): 887-93.

Hock, A. et al. "Myocardial imaging and metabolic studies with [17-123I]iodoheptadecanoic acid in patients with idiolathic congestive cardiomyopathy" J. Nucl. Med. (1983) 24(1): 22-8.

Hoffman, E.J. et al. "Positron emission tomography: principles and quantitation". In: Phelps, M., Mazziotta, J., Schelbert, H., eds. Positron emission tomography and autoradiography: principles and applications for the brain and heart. New York: Raven Press; 1986: 237-286.

Hoffman, E.J. et al. "Quantitation in positron emission computed tomography: 4. Effect of accidental coincidences" 1981. J. Comput. Assist. Tomogr. 5: 391-400.

Hoffman, E.J. et al. "Transaxial tomographic imaging of canine myocardium with 11 C-palmitic acid". 1977. J. Nucl. Med. 18:57-61.

Hull, F.E. et al. "beta-hydroxy fatty acid production during fatty acid oxidation by heart mitochondria" Recent Adv. Stud. Cardiac Struct. Metab. (1975) 7: 13-21.

Humbert, T. et al. "Intramyocardial fate of 15-p-iodophenyl-beta-methylpentadecanoic acid (IMPPA): is it a good tracer of fatty acid myocardial uptake?" Mol. Cell. Biochem. (1989) 88(1-2): 195-200.

Isobe, N. et al. "The characteristics of myocardial fatty acid metabolism in patients with left ventricular hypertrophy" Kaku Igaku (1999) 36(7): 725-33, (English abstract).

Isobe, N. et al. "Usefulness of 201Tl/123I-BMIPP myocardial SPECT to evaluate myocardial viability and area at risk in acute myocardial infarction-comparison with 201Tl/99mTc-PYP dual SPECT" Kaku Igaku (1997) 34(4): 213-20, (English abstract).

Ito, Y. et al. "Relation between thallium-201/iodine 123-BMIPP substraction and fluorine 18 deoxyglucose polar maps in patients with hypertrophic cardiomyopathy" J. Nucl. Cardiol. (2000) 7(1): 16-22.

Jadvar, H. et al. "SPECT and PET in the evaluation of coronary artery disease" Radiographics (1999) 19(4): 915-26.

Jaffe, A.S. et al. "Enhancement of metabolism of jeopardized myocardium by nifedipine". 1987. Int. J. Cardiol. 15:77-89.

Jaszczak, R.J. "SPECT: state-of-the-art scanners and reconstruction strategies". In: Diksic, M., Reba, R.C., eds. Radiopharmaceuticals and brain pathology studied with PET and SPECT. Boca Raton: CRC Press; 1991: 93-118.

Jones, G.S. et al. "Synthesis and biologic evaluation of 1-[11C]-3,3-dimethylheptadecanoic acid" J. Nucl. Med. (1988) 29(1): 68-72.

Jones, G.S. et al. *inventor is an author* "Synthesis and biodistribution of a new 99mtechnetium fatty acid" Nucl. Med. Biol. (1994) 21(1): 117-23.

Kawamoto, M. et al. "Value of fatty acid imaging using 123I-beta-methyl-iodophenyl pentadecanoic acid (BMIPP) to assess viability of infarcted myocardium" Kaku Igaku (1991) 28(9): 1081-9, (English abstract).

Kawamura, Y. et al. "Evaluation of branched chain fatty acid, BMIPP [beta-methyl-omega-(piodophenyl)-pentadecanoic acid] for myocardial imaging-basic experiments" Kaku Igaku (1988) 25(11): 1221-7.

Keriel, C.M. et al. "The intramyocardial fate of [1-14C]palmitate, iodopalmitate, and iodophenylpentadecanoate in isolated rat hearts. A contribution to the choice of an iodinated fatty acid as a tracer of myocardial metabolism" J. Mol. Cell. Cardiol. (1990) 22(12): 1379-92.

Kihara, K. et al. "Clinical study on myocardial imaging with beta-methyl-p-123I)-phenylpentadecanoic acid in patients with mitachoalrnyowthy" Kaku Igaku (1992) 29(4): 453-61, (English abstract).

Kim, Y. et al. "Detection of impaired fatty acid metabolism in right ventricular hypertrophy: assessment by I-123 beta-methyl iodophenyl pentadecanoic acid (BMIPP) myocardial single-photon emission computed tomography" Ann. Nucl. Med. (1997) 11(3): 207-12.

Klein, M.S. et al. "External assessment of myocardial metabolism with [1-11C] palmitate in rabbit hearts" 1979. Am. J. Physiol. 237: H51-H58.

Knabb, R.M. et al. "The temporal pattern of recovery of myocardial perfusion and metabolism delineated by positron emission tomography after coronary thrombolysis". 1987 J. Nucl. Med. 28:1563-1570.

Knapp, F.F. et al. "Pharmacokinetics of radioiodinated fatty acid myocardial imaging agents in animal models and human studies" Q. J. Nucl. Med. (1996) 40(3): 252-69.

Knapp, F.F. et al. "Iodine-123-labeled fatty acids for myocardial single-photon emission tomography: current status and future perspectives" Eur. J. Nucl. Med. (1995) 22(4): 361-81.

Knapp, F.F. et al. "New Radioiodinated methyl-branched fatty acids for cardiac studies" Eur. J. Nucl. Med. (1986) 12 Suppl: S39-44.

Kobayashi, H. et al. "Fatty acid metabolic and perfusion abnormalities in hypertrophied myocardium assessed by dual tracer tomography using thallium-201 and iodine-123-beta-methylpentadecanoic acid" J. Cardiol. (1994) 24(1): 35-43, (English abstract).

Kropp, J. et al. "Pharmacokinetics and metabolism of the methyl-branched fatty acid (BMIPP) in animals and humans" J. Nucl. Med. (1999) 40(9): 1484-91.

Kulkarni, P.V. et al. "Radioiodinated tracers for myocardial imaging" Semin. Nucl. Med. (1990) 20(2): 119-29.

Kurata, C., et al. "Influence of blood substrate levels on myocardial kinetics of idine-123-BMIPP" J. Nucl. Med. (1997) 38(7): 1079-84.

Lin, Q. et al. "Effects of configuration on the myocardial uptake of radioiodinated 3(R)-BMIPP and 3(S)-BMIPP in rats" J. Nucl. Med. (1997) 38(9): 1434-41.

Links, J.M. "Physics and instrumentation of positron emission tomography". In: Frost, J.J., Wagner, H.N., eds. Quantitative imaging- neuroreceptors: neurotransmitters, and enzymes. New York: Raven Press; 1990: 37-50.

Livni, E. et al. *inventor is listed as 2nd author* "Radioiodinated beta-methyl phenyl fatty acids as potential tracers for myocardial imaging and metabolism" Eur. Heart J. (1985): 6 Suppl. B: 85-9.

Livni, E. et al *inventor is an author* "Beta-methyl[1-11C]heptadecanoic acid: a new myocardial metabolic tracer for positron emission tomography" J. Nucl. Med. (1982) 23(2): 169-75.

Livni, E. et al *inventor is an author* "(3H/14C) beta-methylheptadecanoic acid subcellular distribution and lipid incorporation in mouse heart" Lipids (1990) 25(4): 238-40.

Machulla, H.J et al. "Biochemical concept and synthesis of a radioiodinated phenyl fatty acid to in vivo metabolic studies of the myocardium" 1980. Eur. J. Nucl. Med. 5: 171-173.

Machulla, H.J et al. "Comparative evaluation of fatty acids labeled with C-11, Cl-34m, Br-77, and I-123 for metabolic studies of the myocardium: concise communication" 1978. J. Nucl. Med. 19: 298-302.

Miller, D.D. et al. "New Radionuclides for cardiac imaging" Prog. Cardiovasc. Dis. (1986) 28(6): 419-34.

Mori, H. et al. Relationship between ventricular arrhythmias and myocardial fatty acid metabolism in patients with coronary heart disease: evaluation using iodine-123 beta-methyl-p-iodophenyl-pentadecanoic acid J. Cardiol. (1999) 34(2): 61-9, (English abstract).

Myars, D.W. et al. "Substrate use in ischemic reperfused canine myocardium quantitative considerations". 1987 Am. J. Physiol. 253:107-114.

Nakajima, K. et al. "Myocardial fatty acid imaging with 123I-labelled 9-methyl-branched pentadecanoic acid (9MPA) using SPET" Nucl. Med. Commun. (1998) 19(9): 839-47.

Nishimura, T et al. "Assessment of myocardial viability by using newly developed myocardial SPECT imaging" Jpn. Circ. J. (1992) 56(6): 603-7.

Nishimura, T et al. "beta-methyl-p(123I)-iodophenyl pentadecanoic acid single-photon emission computer tomography in cardiomyopathy" Int. J. Card Imaging (1999) 15(1): 41-8.

Nishimura, T et al. "Prognosis of hypertrophic cardiomyopathy: assessment by 123I-BMIPP (beta-methyl-p-(123I)iodophenyl pentadecanoic acid) myocardial single photon emission computed tomography" Ann. Nuc. Med. (1996) 10(1): 71-8.

Nishimura, T. et al. "Newly developed myocardial imaging by using single photon emission computer tomography (SPECT)" Jpn. Circ. J. (1990) 54(3): 328-32.

Nishimura, T. et al. Fatty acid myocardial imaging using 123I-beta-methyliodophenylpentadecanoic acid (BMIPP): comparison of myocardial perfusion and fatty acid utilization in canine myocardial infarction (occlusion and reperfusion model) Eur. J. Nucl. Med. (1989) 15(7): 341-5.

Nishimura, T. et al. Fatty acid myocardial imaging using 123I-beta-methyl iodophenyl pentadecanoic acid (BMIPP): comparison of myocardial blood perfusion and fatty acid metabolism in canine myocardial infarction (occlusion and reperfusion model) Kaku Igaku (1988) 25(12): 1403-15.

Nishimura, T. et al. "Clinical results with beta-methyl-p-(123I)iodophenylpentadecanoic acid, single-photon emission computed tomography in cardiac disease" J. Nucl. Cardiol. (1994) 1(2 Pt.2): S65-71.

Otto, C.A. et al. "Radioiodinated fatty acids for myocardial imaging: effects on chain length" J. Nucl. Med. (1981) 22(7): 613-8.

Otto, C.A. et al. "Subcelllar distribution of [125I]iodoaryl beta-methyl fatty acids" Int. J. Nucl. Med Biol. (1985) 12(3): 223-6.

Otto, CA. et al. "Radioiodinated branched-chain fatty acids: substrates for beta oxidation? Concise communication" J. Nucl. Med. (1984) 25(1): 75-80.

Phelps, M.E. et al. "Effect of positron range on spatial resolution". 1975. J Nucl Med 16: 649-652.

Poe, N.D. "Rationale and radiopharmaceuticals for myocardial imaging" Semin. Nucl. Med. (1977) 7(1): 7-14.

Raichle, M.E. et al. "Measurement of regional substrate utilization rates by emission tomography" 1978. *Science* 199: 986-987.

Ray, J. et al. "Long-chain fatty acids increase basal metabolism and depoloarize mitochondria in cardiac muscle cells" Am. J. Physiol. Heart Circ. Physiol. (2002) 282(4): H1495-501.

Reske, S.N. et al. Assessment of regional myocardial uptake and metabolism of omega-(p-1231-phenyl) pentadecanoic acid with serial single photon emission tomography Nuklearmedizin (1982) 21(6): 249-53.

Reske, S.N. et al. "Experimental basis of metabolic imaging of the myocardium with radioiodinated aromatic free fatty acids" Am. J. Physiol. Imaging (1986) 1(4): 214-29.

Reske, S.N. et al. "15-(p-(I-123)phenyl)) pentadecanoic acid as a tracer of lipid metabolism. Comparison with I-C-14 palmitic acid in murine tissues" 1984. *J. Nucl. Med.* 25: 1335-1342.

Rosamond, T.L. et al. "Metabolic fate of radiolabeled palmitate in ischemic canine myocardium: implications for positron emission tomography". 1987. *J. Nucl. Med.* 28:1322-1329.

Sato, H. et al. "Prediction of functional recovery after revascularization in coronary artery disease using (18) F-FDG and (123)I-BMIPP SPECT" Chest (2000) 117(I):65-72.

Schelbert, H.R. "Positron emission tomography: Assessment of myocardial blood flow and metabolism". 1985 *Circulation* 72: TV 122-133.

Schelbert, H.R. "PET contributions to understanding normal and abnormal cardiac perfusion and metabolism" Ann. Biomed. Eng. (2000) 28(8): 922-9.

Schelbert, H.R. et al. "Imaging metabolism and biochemistry—a new look at the heart". 1983. Am. Heart J. 105:522-526.

Schelbert, H.R. et al. "C-I 1 palmitate for the noninvasive evaluation of regional myocardial fatty acid metabolism with positron-computed tomography. IV. In vivo evaluation of acute demand-induced ischemia in dogs". 1983. *Am. Heart J.* 106:736-50.

Schelbert, H.R. et al. "C-I 1 palmitate for the noninvasive evaluation of regional myocardial fatty acid metabolism with positron computed tomography. III. In vivo demonstration of the effects of the substrate availability on myocardial metabolism". 1983. *Am. Heart J.* 105:492-504.

Schelbert, H.R. et al. "C-I 1 palmitate for the noninvasive evaluation of regional myocardial fatty acid metabolism with positron-computed tomography. IV. In vivo evaluation of acute demand-induced ischemia in dogs" 1983. Am. Heart J. 106: 736-50.

Schelbert. H.R. et al. "Effects of substrate availability on myocardial C-11 palmitate kinetics by PET in normal subjects and patients with ventricular dysfunction". 1986 Am. Heart J. 111:1055-1064.

Schlösser, M. et al. "Fluor-olefine durch Fluormethylenierung von Carbonylverbindungen" 1969. Synthesis 1: 75-76.

Schon, H.R. et al. "C-11 labeled palmitic acid for the noninvasive evaluation of regional myocardial fatty acid metabolism with positron computed tomography. II. Kinetics of C-11 palmitic acid in acutely ischemic myocardium". 1982. Am. Heart J. 103:548-561.

Schon, H.R. et al. "C-11 labeled palmitic acid for the noninvasive evaluation of regional myocardial fatty acid metabolism with positron computed tomography. I. Kinetics of C-11 palmitic acid in normal myocardium". 1982. *Am. Heart J.* 103:532-547.

Shiotani, H. et al. "Myocardial SPECT with iodine-123-labeled beta-methyl branched fatty acid in patients with angina pectoris" Kaku Igaku (1994) 31(11): 1343-9, (English abstract).

Shogase, T. et al. "A role of nuclear medicine in diagnosing cardiac disease-clinical use of 123I-BMIPP and 123I MIBG" Rinsho Byori (2000) 48(2): 113-20, (English abstract).

Sloof, G.W. et al. "Evaluation of heart-to-organ ratios of 123I-BMIPP and the dimethyl-substituted 123I-DMIPP fatty acid analogue in humans" 1997. Nucl. Med. Commun. 18(11): 1065-70.

Sobel, B.E. "Positron tomography and myocardial metabolism: An overview". 1985 Circulation 72: IV22-30.

Sobel, B.E. "Diagnostic promise of positron tomography". 1982. Am. Heart J. 103: 673-681.

Sorenson, J.A.et al. Physics in nuclear medicine, 2nd ed. Philadelphia: W.B. Saunders; 1987. Chapters 19-20, and 22.

Stork, G. et al. "Total Syntheses of (−)-Histrionicotoxin and (−)-Histrionicotoxin 235A" 1990. J. Am. Chem. Soc. 112: 5875-5876.

Stork, G. et al. "A Stereoselective Synthesis of (Z)-1-Iodo-l-Alkenes" 1989. Tetrahedron Lett. 30: 2173-2174.

Suzuki, A. et al. "Comparison of resting beta-methyl-iodophenyl pentadecanoic acid (BMIPP) and thallium-201 tomography using quantitative polar maps in patients with ustable angina" Jpn. Circ. J. (1997) 61(2): 133-8.

Takahashi, N. et al. "Clinical usefulness of myocardial iodine-123-15-(p-iodophenyl)-3(R,S)-methyl-pentadecanoic acid distribution abnormality in patients with mitochondrial encephalomyopathy based on normal data file in bulls-eye polar map" J. Cardiol. (1998) 31(1): 1-10, (English abstract).

Tamaki, N. et al. "Myocardial imaging using PET and SPECT" Nippon Rinsho (1998) 56(10): 2550-5, (English abstract).

Tamaki, N. et al. "Radionuclide assessment of myocardial fatty acid metabolism by PET and SPECT" J. Nucl. Cardiol. (1995) 2(3): 256-66.

Tamaki, N. et al. "Regional metabolic abnormality in relation to perfusion and wall motion in patients with myocardial infarction: assessment with emission tomography using an iodinated branched fatty acid analog" J. Nucl. Med. (1992) 33(5): 659-67.

Taniguchi, M. et al. "Separate evaluation of beta-methyl fatty acid uptake and perfusion in rat myocardium" Kaku Igaku (1989) 26(12): 1523-30, (English abstract).

Ter-Pogossian, M.M. et al. "Regional assessment of myocardial metabolic integrity in vivo by positron-emission tomography with 11C-labeled palmitate". 1980. *Circulation* 61:242-255.

Thrall, J.H. et al. "Development of nonionic gamma-emitting radiopharmaceuticals for myocardial imaging" J. Nucl.Med. (1978) 19(8): 969-71.

Visser, F.C. et al. "Metabolic fate of radioiodinated heptadecanoic acid in the normal canine heart" Circulation (1985) 72(3): 565-71.

Weiss, E.S. et al. "Quantification of infarction in cross sections of canine myocardium in vivo with positron emission transaxial tomography and 11C-palmitate". 1977. *Circulation* 55: 66-73.

Weiss, E.S. et al. "External detection and visualization of myocardial ischemia with 11C-substrate in vitro and in vivo". 1969. Circulation 19:25-32.

Westera, G. et al. "A comparison between terminally radioiodinated hexadecanoic acid (I-HA) and 201—Tl-thallium chloride in the dog heart. Implications for the use of I-HA for myocardial imaging" Eur. J. Nucl. Med. (1980) 5(4): 339-43.

Wieler, H. et al. Standardized noninvasive assessment of myocadial free fatty acid kinetics by means of 15-(p-iodo- phenyl) pentadecanoic acid (123I-pPPA) scintigraphy: II. Clinical Results Nucl. Med. Commun. (1992) 13(3): 168-85.

Yamamichi, Y. et al. "Metabolism of iodine-123-BMIPP in perfused rat hearts" J. Nucl. Med. (1995) 36(6): 1043-50.

Yamamoto, K. et al *inventor is an author* "Dual tracer autoradiographic study of beta-methyl-(1-14C) heptadecanoic acid and 15-p-(131I)-iodophenyl-beta-methylpentadecanoic acid in normotensive and hypertensive rats" J. Nucl. Med. 1986 27 7 : 1178-83.

Yazaki, Y. et al. "Assessment of myocardial fatty acid metabolic abnormalities in patients with idiopathic dilated cardiomyopathy using 123I BMIPP SPECT: correlation with clinicopathological findings and clinical course" Heart (1999) 81(2): 153-9.

Gilbert Stork and Kang Zhao, "A stereoselective synthesis of (Z)-1-IODO-I alkenes." Department of Chemistry, Columbia University New York, 10027 Tetrahedron Letters, vol. 30, No. 17, pp. 2173-2174, 1989.

Leo A. Paquette and Simon Bailey, "Evaluation of D-Ribose as an Enantiopure Bilding Block for Construction of the C-Ring of Taxol abd Its Congeners." Evan Chemical Laboratories, The Ohio State University, Columbus OH 43210 Jul. 25, 1995 J. Org. Chem. 1995, 60, pp. 7849-7856.

William D. Wulff and Timothy S. Powers "Stereochemical Control in Intramolecular Diels-Alder Reactions with Carbene Complexes as Ester Synthons." Searle Chemistry Laboratory, Department of Chemistry, University of Chicago, Chicago Illinois 60637, Oct. 20, 1992 J. Org. Chem. 1993, 58, 2381-2393.

Daryl G. Cox et al. "Surprising Stereochemical Control of Wittig Olefination Involving Reaction of Fluorine-Containing Phosphoranium Salt and Aldehydes." Department of Chemistry, University of Iowa, Iowa City, Iowa 52242. Oct. 22, 1984 J. Am. Chem. Soc. 1985, 107, 2811-2812.

M.M. Goodman, et al. "New Myocardial Imaging Agents: Synthesis of 15-(p-lodephenyl)-3(R,S)-methylpentadecanoic Acid by Decmposition of a 3,3 (1,5-Pentanediyl)triazene Precursor." Nuceaar Medicine Group, Health and Safety Research Division, Oak ridge National Laboratory, Oak Ridge, Tennessee 37830. J. Org. Chem. 1984, 49, 2322-2325.

Andre B. Charette, et al. "Improved Procedure for the Synthesis of Enantiometrically Enriched Cyclopropylmethanol Derivatives." Department de Chimie, University of Montreal, Quebec, Canada H3C 3J7. J. Org. Chem. 1995, 60, 1081-1083.

Helen E. Savaki, "Sokoloff s 14C-deoxyglucose method." Department of Basic Sciences, Faculty of Medicine, University of Crete, Heraklion, Crete, Greece; and Institute of Applied and Computational Mathematics, FO.R.T.H., Heraklion, Crete, Greece. Brain Research Bulletin, vol. 50, Nos. 5/6, pp. 405-407, 1999.

Robert C. Marshall, et al. "Estimating glucose metabolism using glucose analogs and two tracer kinetic models in isolated rabbit heart." Am. J. Physiol. 275 (Heart Cir. Physiol. 44): H668-H679, 1998.

Leonard M. Freeman, et al., "Cardiovascular Nuclear Medicine, Part 1." University of Minn., Seminars in Nuclear Medicine, vol. XXIX, No. 3 Jul. 1999; pp. 237-258.

Elmaleh Dr. et al., "The Synthesis and Evaluation of Radioiodinated 14-(iodophenyl)- 3-(R,S) methyltetradecanoic Acid." Nuclear Medicine Communications 6, 287-297 (1985).

H. Wieler et al., "Standardized non-invasive assessment of myocardial free fatty acid kinetics by means of 15-(para-iodophenyl) pentadecanoic acid ($^{123}$I-pPPA)scintigraphy:1. Method." Nuclear Medicine Communications 11, 865-878 (1990).

Van Der Wall EE, et al., "Dynamic Myocardial Scintigraphy with $^{123}$I-Labeled Free Fatty Acids in Patients with Myocardial Infraction." Eur. J. Nucl. Med. (1981) 6:383-389.

Toshihiro Takahashi et al., "Biological Evaluation of 5-Methyl-branched-chain c"-[$^{18}$F] Fluorofatty Acid: A Potential Myocardial Imaging Tracer for Positron Emission Tomography." Nuclear Medicine & Biology, vol. 23, pp. 303-308, 1996.

Norman D. Poe, et al. "Experimental Basis for Myocardial Imaging with $^{123}$I-Labeled Headecenoic Acid." J. Nucl. Med. 17: 1077-1082, 1976. vol. 17, No. 12.

E. E. Van Der Wall, "Myocardial Imaging with Radiolabelled Free Fatty Acids: A critical Review" European Heart Journal (1985) 6 (Supplement B) 29-38.

Norman D. Poe M.D., et al., "Myocardial imagining with $^{123}$I-Hexadecenoic Acid." vol. 124, No. 2, Radiology 124:419-424, Aug. 1977.

Van Der Waal EE, et al., "I-123 Labeled Hexadecenoic Acid in Comparison with Thallium-201 for Myocardial Imaging in Coronary Heart Disease." Eur. J. Nucl. Med. 5, 401-405 (1980).

Anna-Liisa Kairento, et al., "Comparative Evaluation of [$^{123}$I]14-p-Iodophenyl-Beta-Methyltetradecanoic Acid and Thallium-20I in the Detection of Infracted Areas in the Dog Heart Using SPECT". Nucl. Med. Biol. vol. 15, No. 3, pp. 333-338, 1988.

Masahide Kawamoto, MD et. Al., "Significance of myocardial uptake of iodine 12-labeled beta-methyl iodophenyl pentadecanoic acid: Comparison with kinetics of carbon 11-labeled palmitate in positron emission tomography." Journal of Nuclear Cardiology vol. 1, No. 6: pp. 522-528 (1994).

Hideki Kobayashi et al., "Evaluation of Myocardial Perfusion and Fatty Acid uptake Using a Single Injection of Iodine- 123-BMIPP in Patients with Acute Coronary Syndromes." The journal of Nuclear Medicine, vol. 39, No. 7, Jul. 1998 pp. 1117-1122.

D. Douglas Miller et. al., "Fatty Acid Analogue Accumulation: A Marker of Myocyte Viability in Ischemic-Reperfused Myocardium." Circulation Research vol. 63, No. 4, Oct. 1988 pp. 681-692.

Fritzberg, A.R. et al. "Iodophenylsulfonamide fatty acid analogs as potential myocardial imaging agents" Int. J. Appl. Radiat. Isot. (1982) 33(6): 451-3.

Sokoloff, L. et al. "The [14C]-deoxyglucose method for the measurement of local cerebral glucose utilization: Theory, procedure, and normal values in the conscious and anesthetized albino rat" 1977. J. Neurochem. 28: 879-916.

* cited by examiner

Synthesis of [$^{18}$F]-9-Fluoro-3,4-Cyclopropylheptadecanoic Acid

Aliphatic-halide

A = $(CH_2)_y$, O, S
y = 1, 2, 3, 4
cis and trans; R,R and S,S
m = 0, 1, 2, 3, 4, etc.
n = 14 - 8
p = 0 - 6
R = $CH_3$
X = $^{18}F$ or $^{123}I$ examples:

$A = (CH_2)_x, O, S$ $x = 1, 2, 3, 4$ cis and trans; R,R and S,S $m = 0, 1, 2, 3, 4,$ etc.

$n = 14 - 8$ $R = {}^{18}F$-phenyl or ${}^{123}I$-phenyl trans, S,S cis, S,S trans, R,R cis, R,R Synthesis of Endo- [18F]Fluoro- or [123I]iodo-3,4-Cyclopropylheptadecanoic Acid Endo-halovinyl $X = {}^{18}F$ or $^{123}I$, $Y = H$
$X = H$, $Y = {}^{18}F$ or $^{123}I$
$A = (CH_2)_z$, O, S
$z = 1, 2, 3, 4$
cis and trans; R,R and S,S
$m = 0, 1, 2, 3, 4$, etc
$n = 14 - 8$
$p = 0 - 6$
$R = CH_3$, aryl, heterocyclic Synthesis of Exo- [$^{18}$F]Fluoro- or [$^{123}$I]iodo-3,4-Cyclopropylheptadecanoic Acid Exo-halovinyl $A = (CH_2)_y, O, S$ $y = 1, 2, 3, 4$ cis and trans; R,R and S,S $m = 0, 1, 2, 3, 4,$ etc.

$n = 14 - 8$ $p = 0 - 6$ $R = CH_3$, aryl, heterocyclic $X = {}^{18}F$ or ${}^{123}I$ Ring is 4 or 5 membered with all structural variations from FIG.2, 9, 11, and 13

$D = CH_2$ or $CH_2CH_2$ $E = CH_2$ or $CH_2CH_2$ $m = 0, 1, 2, 3, 4$, etc.

$n = 14 - 8$ $R = CH_3$, aryl, heterocyclic

METHOD FOR MONITORING BLOOD FLOW AND METABOLIC UPTAKE IN TISSUE WITH RADIOLABELED ALKANOIC ACID

REFERENCE TO RELATED APPLICATIONS/INCORPORATION BY REFERENCE

This application is a divisional application of U.S. application Ser. No. 10/827,054 filed Apr. 19, 2004, pending, which claims priority to U.S. provisional application Ser. No. 60/463,574, filed Apr. 17, 2003. The entire contents of the aforementioned patent applications are incorporated herein by this reference.

This application claims priority to U.S. application Ser. No. 60/463,574, filed on Apr. 17, 2003.

Each of the applications and patents cited in this text, as well as each document or reference cited in each of the applications and patents (including during the prosecution of each issued patent; "application cited documents"), and each of the U.S. and foreign applications or patents corresponding to and/or claiming priority from any of these applications and patents, and each of the documents cited or referenced in each of the application cited documents, are hereby expressly incorporated herein by reference. More generally, documents or references are cited in this text, either in a Reference List before the claims, or in the text itself; and, each of these documents or references ("herein-cited references"), as well as each document or reference cited in each of the herein-cited references (including any manufacturer's specifications, instructions, etc.), is hereby expressly incorporated herein by reference. Documents incorporated by reference into this text may be employed in the practice of the invention. This application makes reference to U.S. Pat. No. 4,524,059, issued on Jun. 18, 1985, the contents of which are incorporated herein by reference.

FIELD OF THE INVENTION

The present invention relates to novel radiolabeled fatty acid analogs having a cyclic organic substituent, where a positron or gamma-emitting label is placed at a position on a fatty acid backbone and an organic substituent is substituted at the 2,3; 3,4; 4,5; 5,6 and other sequence positions of a fatty acid backbone. These novel fatty acid analogs are designed to enter the tissues of interest by the same long chain fatty acid carrier mechanism as natural fatty acids, however, functional substituents in the 2,3; 3,4; 4,5; 5,6 and other sequence positions, block the catabolic pathway, thus trapping these analogs in a virtually-unmodified form in the tissues of interest.

BACKGROUND OF THE INVENTION

Many imaging modalities have been developed for non-invasive evaluation of heart disease. Radiotracers that can assess myocardial perfusion and heart metabolism are useful for clinical evaluation of ischemic heart disease and cardiomyopathies. Fatty acids (FAs) are the principal substrate for the production of adenosine triphosphate (ATP) in the myocardium under aerobic conditions. Nearly 70% of myocardial energy results from metabolism of fat in the basal state, with the remainder of the myocardial energy requirements supplied by glucose (15%), lactate and pyruvate (12%) and amino acids (5%). Therefore, FAs and modified fatty acids (MFAs) have been proposed for imaging the heart.

Uptake of free FAs by the myocardium occurs at an extraction percentage of 40% to 60% of blood content, which is proportional to perfusion. Transported to the heart as nonesterified FAs, as triglycerides in very low-density lipoprotein particles or in chylomicrons, or bound to serum albumin, they pass along concentration gradients to the interstitium. Under these conditions, FAs supply as much as 70% of oxidatively metabolized substrate. The extraction of free FAs by the myocyte is regulated by several variables including FA chain length, the availability of other metabolic substrates, circulating levels of hormones, cardiac workload, and the presence or absence of ischemia.

MFAs behave like native FAs up to the β-oxidation step in the mitochondria, where it is sequestered for a long period of time (Livni, E. et al. 1990 *Lipids* 25: 238-40). Highly simplified, the fate of an FA may be described as follows: FA passes from capillary blood into the interstitial space. It may "back-diffuse" to the vascular space or pass through the interstitial space, where it may become activated as acyl-coenzymeA (CoA). The activated FA can then be esterified to form triglycerides, incorporated into phospholipids or carried into the mitochondria and oxidized. The activation of FA to acyl-CoA requires energy and is believed to be essentially irreversible in vivo. Since acyl-CoA cannot escape through the cell membrane, it becomes trapped in the cell. However, the formation of triglycerides is not irreversible and these can be broken down into the constituent FA and glycerol, adding to the FA pool.

As described above, there is an intimate relationship between FA metabolism and myocardial integrity. As a result of their high rate of utilization, labeled FAs in conjunction with suitable detection techniques can provide a means of quantifying in vivo regional myocardial metabolism. Two approaches can be employed to quantify the utilization of substrates in vivo. The first involves the use of radiolabeled, positron emitting physiologic substrates. This approach has been used to assess glucose and FA metabolism in the heart with carbon 11 ($^{11}$C) palmitate (PA) in rabbit (Raichle, M. E. et al. (1978) *Science* 199: 986-987). It has been demonstrated that after brief intervals of ischemia, PA extraction fell markedly, even when alterations in cardiac function were reversible (Klein M. S. et al (1979) *Am. J. Physiol.* 237: H51-H58; Goldstein R. A. et al (1980) *J. Nucl. Med.* 21: 342-348; Weiss, E. S. et al. (1969) *Circulation* 19: 25-32; Fox, K. A. et al. (1975) *Circ. Res.* 57: 232-243; Hoffman, E. J. et al. (1977) *J. Nucl. Med.* 18: 57-61; Ter-Pogossian, M. M. et al. (1980) *Circulation* 61: 242-255; Weiss E. S. et al. (1977) *Circulation* 55:66-73; Schon, H. R. et al. (1982) *Am. Heart J.* 103: 532-547; Schon, H. R. et al. (1982) *Am. Heart J.* 103:548-561; Schelbert, H. R. et al. (1983) *Am. Heart J.* 105:492-504; Schelbert, H. R. et al (1983) *Am. Heart J.* 106: 736-50; Sobel, B. E. (1982) *Am. Heart J.* 103:673-681; Schelbert, H. R. et al. (1983) *Am. Heart J.* 105:522-526; Schelbert, H. R. (1985) *Circulation* 72: TV122-133; Sobel, B. E. (1985) *Circulation* 72:IV22-30; Rosamond, T. L. et al (1987) *J. Nucl. Med.* 28: 1322-1329; Grover-McKay, M. et al (1986) *Circulation* 74: 281-292; Schelbert, H. R. et al (1986) *Am. Heart J.* 111: 1055-1064; Jaffe, A. S. et al (1987) *Int. J. Cardiol.* 15: 77-89; Knabb, R. M. et al (1987) *J. Nucl. Med.* 28:1563-1570; Myars, D. W. et al (1987) *Am. J. Physiol.* 253: 107-114). In addition, zones of persistently decreased flow also showed decreased PA extraction (Schelbert, H. R. (1985) Circulation 72: TV122-133).

Other studies using $^{11}$C-PA provide the experimental basis for studying regional myocardial FA distribution. The application of physiologic radiolabeled FAs to in vivo quantification of regional myocardial metabolic rates suffers from several drawbacks. First, the use of $^{11}$C-FAs labeled with $^{11}$C on the carboxyl group is subject to loss of labeling during the first round of β-oxidation. Studies employing direct intracoronary administration of $^{11}CO_2$ and direct myocardial monitoring demonstrate the evolution of $^{11}CO_2$ within 30 seconds and a 50% clearance within 2-8 minutes. Secondly, the rapid washout of the radiolabel due to β-oxidation and short sequential imaging periods imposes limitations on counting statistics. Third, in the myocardial cell, FAs are distributed among different pools: free FAs, triglycerides, phospholipids, diglycerides, and monoglycerides. It is unclear whether the rate of FA oxidation is proportional to the rate of triglyceride hydrolysis. After the initial clearance of radioactivity from the blood, there is a rise in activity due to the release of radiolabeled metabolites from the liver. This makes the completion of labeled FA detection necessary before the rise occurs. Other studies in dogs using $^{11}C$-PA showed that during ischemia, quantitation is limited due to the complexity of its metabolic fate (Schelbert et al., 1983 Am. Heart J. 106: 736-50). $^{11}C$ acetate has been proposed as an alternative due to its simpler metabolic fate.

The second approach involves the use of "analog tracers" that enter a known metabolic pathway. However, because of their unique chemical structure, metabolism of these tracers stop at a certain stage, leaving the radiolabel trapped in the cell in a known form. This concept has been applied to the study of glucose metabolism using glucose analogs such as 1-[$^{11}C$]-2-deoxyglucose (2DG) and 2-[$^{18}F$]-fluorodeoxyglucose (2FDG). The principle of metabolic trapping has been used successfully with 2FDG to measure in vivo regional glucose metabolic rates in humans. Investigations of the use of 2FDG for measuring myocardial glucose metabolism have been conducted. Similarly, FAs have also been widely used to measure metabolic activity in the myocardium. A major drawback to the use of FAs is the quick washout rates, as alluded above. FAs tend to wash out very quickly due to β-oxidation, depending on the position of the radionuclide. Subsequently, the radiolabeled FA or metabolites can then accumulate in tissues other than the region of interest, primarily liver and lung. In radiohalogenated aliphatic fatty acids, such accumulation occurs frequently with $^{123}I$, which migrates and is stored in the thyroid gland, and $^{18}F$, which is stored in bone.

Evans and coworkers radiolabeled straight-chain FAs by saturation of the double carbon bond of oleic acid with $^{131}I$ and found that although photoscans of the canine heart were produced, the low specific activity of the final product precluded its clinical use (Evans, J. et al (1965) Circ. Res. 16: 1-10; reviewed in Corbett, J. R., (1999) Semin. Nucl. Med. 29(3): 1999-2006). Since then, there have been many MFAs developed for cardiac imaging. Poe and coworkers showed that [$^{123}I$]-hexadecanoic acid (IHXA) and [$^{123}I$]-heptadecanoic acid (IHDA) were indicators of myocardial perfusion in experimental canine models and demonstrated clearance rates similar to that of $^{11}C$-PA (Poe, N. et al, (1976) J. Nucl. Med. 16; 17-21; Poe, N. et al, (1977) Radiology 124: 419-424). All subjects with prior myocardial infarcts showed decreased regional tracer uptake. Machulla et al reported that the ω-terminal labeled FAs were more efficiently extracted than analogs labeled in the α-position, and that IHDA had the highest uptake (Machulla, H. et al (1978) J. Nucl. Med. 19: 298-302).

Although IHDA and IHXA have potential as myocardial perfusion agents, their ability to access myocardial metabolism in patients has been questioned (Freundlieb, C. et al, (1980) J. Nucl. Med. 21(11): 1043-50; Visser, F. C. et al, (1985) Circulation 72(3): 565-71). The clinical utility of radiolabeled iodoalkyl FAs appears limited by: 1) the rapid appearance of free radioiodine, requiring special correction procedures to differentiate between myocardial and blood pool activity; 2) short elimination half-lives, making them unattractive agents for single photon imaging; and 3) data suggesting that the elimination rate may not reflect β-oxidation but rather de-iodination and back-diffusion of the tracer across the membrane. Further, protocols and algorithms developed for planar imaging are not applicable to single photon imaging (SPECT), effectively eliminating it as a potential imaging modality for the measurement of metabolic parameters with these radiotracers. Imaging difficulties associated with de-iodination of IHDA and IHXA ultimately resulted in the development of the branched FAs.

The molecular structure of FAs can be modified to attenuate myocardial metabolism, prolong cardiac retention, and avoid washout effects. To prevent rapid de-iodination of alkyl FAs and promote stabilization of the iodine radiolabel, 15-(p-iodophenyl) pentadecanoic acid (IPPA) was developed as an alternative (Machulla, H. et al (1980) Eur. J. Nucl. Med. 5: 171-173). The $^{123}I$-label attached to a terminal phenyl ring in either the ortho or para position is stabilized against de-iodination. [$^{123}I$]-IPPA has kinetics similar to the physiological substrate $^{11}C$-PA in perfused rat hearts (Reske, S. et al, (1984) J. Nucl. Med. 25: 1335-1342). The uptake of IPPA is related to perfusion, and IPPA generally follows the normal metabolic pathway for β-oxidation (Caldwell, J. et al, (1990) J. Nucl. Med. 31: 99-105). Iodobenzoic acid and its metabolite iodohippurate are the products of IPPA oxidation, which are rapidly excreted by the kidneys with the iodine moiety still attached, preventing buildup of free radioiodine.

Studies using myocardial biopsy specimens have shown rapid extraction by normal myocardium, with biexponential clearance, including a fast component $t_{1/2}$ of 3.5 minutes (flow), a slow component $t_{1/2}$=130 minutes (metabolism), and a blood clearance $t_{1/2}$=5 minutes (elimination) (Chien, K. et al (1983) Am. J. Physiol. 245: H693-H697). Compared with alkyl straight-chain FAs, IPPA has the advantages of rapid myocardial uptake, iodine stabilization, and rapid clearance of metabolites from the body. While IPPA was a significant improvement over the straight chain FAs, providing excellent image quality, and permitting SPECT image acquisition and quantification with estimates of metabolic rates, the rate of IPPA metabolism and clearance was still relatively fast for SPECT imaging. Thus, an effort was made to develop radiolabeled FA analogs with attenuated oxidative metabolism.

Methyl branching was introduced to slow myocardial clearance and improve quantitative image accuracy (Livni, E. et al. 1982 J. Nucl Med. 23: 169-75; Elmaleh, D. R. et al. 1981. J. Nucl. Med. 22: 994-9; Elmaleh, D. R. et al. 1983 Int. J. Nucl. Med. Biol. 10:181-7; Goodman, M. M. et al. 1984 J. Org. Chem. 49: 2322-5; Livni, E. et al. 1985. Eur. Heart J. 6 (Suppl B): 85-9; Bianco, J. A. et al. Eur. J. Nucl. Med. 12: 1204). The addition of methyl group(s) at the 3-carbon position blocks β-oxidation by preventing formation of the 3-carboxy-intermediate (β-ketoacyl-ScoA) via the dehydrogenation of the 5-L-hydroxy ScoA intermediate. Two iodine-labeled MFAs that provide prolonged myocardial retention are 15-(p-iodophenyl)-3-(R,S')-methyl-pentadecanoic acid (BMIPP) and 15-(p-iodophenyl)-3,3-dimethyl-pentadecanoic acid (DMPP). The kinetics and subcellular distribution of these methyl-branched FAs have been evaluated, with DMIPP demonstrating the greatest myocardial retention times, with no significant metabolism (Knapp, F. et al, (1986) Eur. J. Nucl. Med. 12: S39-S44; Ambrose, K. et al, (1987) Eur. J. Nucl. Med. 12: 486-491). However, DMIPP demonstrates very slow myocardial clearance (6-7 hours), limiting its usefulness for certain applications. Additionally, DMIPP has been detected in exogenous tissues, such as the liver (Sloof et al, (1997) *Nucl. Med. Commun.* 18(11): 1065-70). BMIPP also accumulates in the liver, but to a lesser extent than DMIPP.

BMIPP is currently the most widely used radiolabeled MBA for cardiac imaging. BMIPP has prolonged myocardial retention (30-45 minutes) and undergoes β-oxidation in the myocyte after the initial α-oxidation and oxidative decarboxylation, producing α-hydroxy-BMIPP as an intermediate (Yamamichi, Y. et al, (1995) *J. Nucl. Med.* 36: 1042-1050). After loss of propionic acid, further degradation proceeds through successive cycles of β-oxidation to the end product, (p-iodophenyl)-acetic acid. Additionally, it has been shown that initial distribution of BMIPP in the first several minutes after injection is comparable to that of perfusion tracers like $^{201}$Thallium and $^{99m}$technetium compounds. Thus, it can be argued that the use of BMIPP alone imaged early and late after injection is all that is required to evaluate myocardial viability with a high degree of accuracy. Likewise, numerous groups have accomplished work on FAs as potential markers for blood flow and their collective data determined that a single injection of certain FAs produces images that are similar to those produced by $^{201}$Tl, $^{11}$C-PA, or potassium (van der Wall, E. E. et al, (1980) *Eur. J. Nucl. Med.* 5(5): 401-5; Kairento, A. L. et al, (1988) *Int. J. Rad. Appl. Instrum.* B.15 (3): 333-8; Kobayashi, H. et al, (1997) *J. Nucl Med.* 39(7): 1117-22; Kawamoto, M. et al, (1994) *J. Nucl. Cardiol.* 1(6): 522-8). Thus, a single injection limits the amount of radioactivity exposure to the patient, as well as being cost-effective. While BMIPP is a widely used FA for both flow and metabolism, there is a need in the art for MFAs that have longer myocardial retention without appreciable metabolism and migration of the radiolabel to other unwanted areas. BMIPP and its metabolites have been detected at significant levels in lung tissue (Sloof et al, (1997) *Nucl. Med. Commun.* 18(11): 1065-70).

While there are a plurality of MFAs that are suitable for imaging, many either undergo significant β-oxidation, resulting in production of radiolabeled metabolites that can accumulate in other tissues, or fail to be efficiently transported into the myocardium, resulting in back-diffusion and re-esterification into the triglyceride pool. Thus, there is a need in the art for a radiolabeled MFA analog that is transported to the tissue of interest by endogenous, physiological means, but fails to undergo β-oxidation due to the presence of branched organic substituents. This would allow the MFA to be retained in a virtually unmodified form for a sufficient amount of time in the tissue of interest (i.e. cardiac tissue) to be detected by conventional means. Further, there is a need in the art for a radiolabeled MFA that shares the aforementioned characteristics and is retained without significant migration to unwanted areas of the organism.

SUMMARY OF THE INVENTION

Alterations in FA uptake are considered to be sensitive markers of ischemia and myocardial damage. Radiolabeled FAs that initially display myocardial blood flow and eventually show adequate myocardial retention associated with metabolic activity are attractive candidates for clinical evaluation of regional discrepancies in heart blood flow and FA metabolism, which occur in ischemic heart disease and cardiomyopathies.

Therefore, the present invention relates to novel radiolabeled FA analogs having a cyclic organic substituent, where a positron or gamma-emitting label is placed at a position on an FA backbone and an organic substituent is substituted at the 2,3; 3,4; 4,5; 5,6 and other sequence positions of an FA backbone. These novel FA analogs are designed to enter the tissues of interest by the same long chain FA carrier mechanism as natural FAs, however, functional substituents in the 2,3; 3,4; 4,5; 5,6 and other sequence positions, block the catabolic pathway, thus trapping these analogs in the tissues of interest.

Accordingly, in one aspect of the present invention, a radioactively labeled analog of a fatty acid that is taken up by mammalian tissue is provided, comprising the formula:

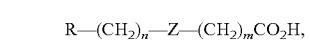

R—(CH$_2$)$_n$—Z—(CH$_2$)$_m$CO$_2$H, wherein n is 8-22, m is 0-10, R is a CH$_3$, aryl or a heterocyclic group, and Z is a cyclic or heterocyclic organic substituent which causes said analog to be metabolically trapped in said tissue.

The term "aryl" in the context of this application may comprise, but is not limited to, a 5-, 6- or 7-membered ring. Further, the term "cyclic" can refer to cyclic alkanes such as cyclopropyl, cyclobutyl, and cyclopentyl, but is not so limited. Similarly, "heterocyclic" can refer to any 3 to 5-membered ring structure that can comprise, for example, nitrogen, sulfur, or oxygen atoms.

In another aspect, a radioactively labeled analog of a fatty acid that is taken up by mammalian tissue is provided, comprising the formula:

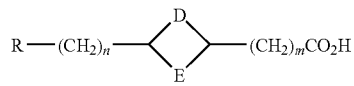

wherein D is CH$_2$ or CH$_2$CH$_2$, E is CH$_2$ or CH$_2$CH$_2$, m is 0-10, n is 8-14 and R is a CH$_3$, aryl or a heterocyclic group, wherein cyclic organic substituent —CDCE— causes said analog to be metabolically trapped in said tissue.

Another aspect of the present invention provides a radioactively labeled analog of a fatty acid, comprising the formula:

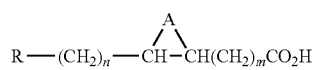

wherein A can be (CH$_2$)$_x$, O, or S; X is 1, 2, 3, and 4; cis and trans isomers R,R and S,S and their racemic forms; m is 0-10; n is 14-8; R is $^{18}$F-phenyl, or $^{123}$I-phenyl, and wherein the cyclic or heterocyclic organic substituent —CH-A-CH— causes said analog to be metabolically trapped in said tissue.

In another aspect of the present invention, a radioactively labeled analog of a fatty acid that is taken up by mammalian tissue is provided, comprising the formula:

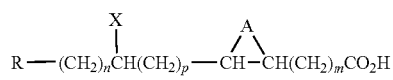

wherein A is (CH$_2$)$_y$, O, or S; y is 1, 2, 3, 4; cis and trans isomers R,R, and S,S and their racemic forms; m is 0-10; n is 14-8; p is 0-6; R is CH$_3$; and X is a radioactive label.

The present invention also provides a radioactively-labeled analog of a fatty acid that is taken up by mammalian tissue, comprising the formula:

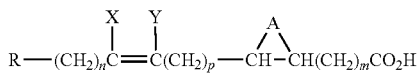

wherein X can be H, $^{18}$F, $^{123}$I, $^{131}$I, $^{34m}$Cl, $^{75}$Br, $^{76}$Br, $^{77}$Br, alkyl and heteroalkyls thereof; Y can be H, $^{18}$F, $^{123}$I, $^{131}$I, $^{34m}$Cl, $^{75}$Br, $^{76}$Br, $^{77}$Br, alkyl and heteroalkyls thereof; A is $(CH_2)_z$, O or S; Z is 1-4, m is 0-10, n is 8-14, p is 0-6, R is $CH_3$, aryl or heterocyclic, and wherein the cyclic or heterocyclic organic substituent —CH-A-CH— causes said analog to be metabolically trapped in said tissue.

Another aspect of the present invention provides a radioactively labeled analog of a fatty acid that is taken up by mammalian tissue, comprising the formula:

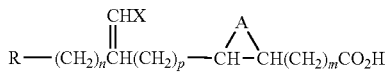

wherein A is $(CH_2)_z$, O or S, y is 1-4, m is 1-10, n is 8-14, p is 0-6, R is $CH_3$, aryl or heterocyclic, X can be $^{18}$F, $^{123}$I, $^{131}$I, $^{34m}$Cl, $^{75}$Br, $^{76}$Br or $^{77}$Br; and wherein the cyclic or heterocyclic organic substituent —CH-A-CH— causes said analog to be metabolically trapped in said tissue.

Preferably, the novel fatty acid has a cyclic organic substituent labeled with $^{18}$F, $^{123}$I, $^{131}$I, $^{34m}$Cl, $^{75}$Br $^{76}$Br and $^{77}$Br.

In another embodiment, the novel fatty acid having a cyclic organic substituent is saturated.

Another embodiment of the present invention describes the novel fatty acid having a cyclic organic substituent that contains one or more double bonds.

In one embodiment, the organic substituent is a 3-to-5 membered cyclic structure.

Another aspect of the present invention provides a method of measuring blood flow in a subject, comprising the following steps:
  a) localizing a detectable amount of a FA composition of the invention to a tissue of interest;
  b) detecting a signal from said FA composition in a tissue of interest within about 1 minutes and about 5 minutes after administration;
  c) imaging a tissue of interest and;
  d) determining the rate of blood flow in a tissue of interest.

In another aspect, a method for measuring metabolism in a subject comprises the following steps:
  a) localizing a detectable amount of a FA composition of the invention to a tissue of interest;
  b) detecting a signal from said FA composition in a tissue of interest within about 30 minutes and about 120 minutes after administration;
  c) imaging a tissue of interest and;
  d) determining the rate of metabolism in a tissue of interest.

Another aspect of the present invention provides a method for retaining a fatty acid composition of the invention in a tissue of interest, comprising the steps of:
  a. localizing a detectable amount of the composition to the tissue;
  b. retaining the composition, or a metabolic derivative thereof, in the tissue by reducing transport and back-diffusion of the composition; and
  c. detecting the composition or the metabolic derivative in the tissue.

The present invention further provides a method for retaining a fatty acid composition of the invention in a tissue of interest, comprising the steps of:
  a. localizing a detectable amount of the composition to the tissue;
  b. retaining the composition, or a metabolic derivative thereof, in the tissue by reducing dehydrogenation of the composition; and
  c. detecting the composition or the metabolic derivative in the tissue.

Another aspect provides a method for retaining a fatty acid composition of the invention in a tissue of interest, comprising the steps of:
  a. localizing a detectable amount of the composition to the tissue;
  b. retaining the composition, or a metabolic derivative thereof, in the tissue by reducing hydroxylation of the composition; and
  c. detecting the composition or the metabolic derivative in the tissue.

The present invention further provides a method for retaining a fatty acid composition of the invention in a tissue of interest, comprising the steps of:
  a. localizing a detectable amount of the composition to the tissue;
  b. retaining the composition, or a metabolic derivative thereof, in the tissue by reducing ketoacyl formation of the composition; and
  c. detecting the composition or the metabolic derivative in the tissue.

Yet another aspect of the present invention provides a method for retaining a fatty acid composition of the invention in a tissue of interest, comprising the steps of:
  a. localizing a detectable amount of the composition to the tissue;
  b. retaining the composition, or a metabolic derivative thereof, in the tissue by reducing ketoacetyl elimination of the composition; and
  c. detecting the composition or the metabolic derivative in the tissue.

In one embodiment, the tissue of interest is heart tissue.
In another embodiment, the tissue of interest is liver tissue.
The present invention preferably describes tumor tissue as the tissue of interest.
In one embodiment, the tissue is diseased.
In another embodiment, the tissue is healthy.
Preferably, the tissue can be subjected to exercise-induced stress or pharmacologically induced stress.

Another aspect of the present invention provides a method of synthesizing a fatty acid composition of the invention, comprising the steps of:
  a) synthesizing a mono-protected primary alcohol from a starting compound;
  b) adding a cyclic or heterocyclic organic substituent to the mono-protected primary alcohol to form a cyclic mono-protected primary alcohol; and
  c) treating the cyclic mono-protected primary alcohol to form the fatty acid analog.

One embodiment of the present invention describes the starting compound comprising a carbon backbone that is saturated.

In another embodiment, the starting compound comprises a carbon backbone that unsaturated.

Another embodiment describes the starting compound comprising a terminal phenyl group.

In another embodiment, the starting compound is a cyclic primary alcohol.

One embodiment of the present invention describes a cyclic alkane as the cyclic organic substituent.

Another embodiment describes the heterocyclic organic substituent as a 3-5-membered heterocyclic ring structure.

In another embodiment, the method further comprises adding a radioactive label that is bonded to a carbon atom of the analog.

The present invention further provides a kit for administration of a radioactively labeled analog of a fatty acid, comprising an analog of a fatty acid synthesized according to the methods of the invention, a radioactive isotope, a pharmaceutically acceptable carrier, and optionally instructions for preparing the radioactively labeled analog or use thereof.

Preferably, the radioactive isotope is selected from the group consisting of $^{18}F$, $^{123}I$, $^{131}I$, $^{34m}Cl$, $^{75}Br$, $^{76}Br$ and $^{77}Br$.

Throughout this specification and claims, the word "comprise" or variations such as "comprises" or "comprising" will be understood to imply the inclusion of a stated integer or group of integers but not the exclusion of any other integer or group of integers.

These and other embodiments are disclosed or are obvious from and encompassed by, the following Detailed Description.

BRIEF DESCRIPTION OF THE DRAWINGS

The following Detailed Description, given by way of example, but not intended to limit the invention to specific embodiments described, may be understood in conjunction with the accompanying Figures, incorporated herein by reference.

DETAILED DESCRIPTION OF THE INVENTION

In accordance with the instant invention, novel radiolabeled fatty acid compositions having a cyclic organic substituent can be administered to an animal, including a human, to determine both blood flow to the organ and metabolism by an organ of the body of the animal. In the present application, the term "modified fatty acid" can be regarded as a synthetic or naturally occurring fatty acid that has been synthetically modified. Also within the context of this application, the term "organic substituent" refers to organic chemical structures bonded to the fatty acid that is effective in decreasing the in vivo rate of β-oxidation of the fatty acid in tissues of interest.

Figure 2:
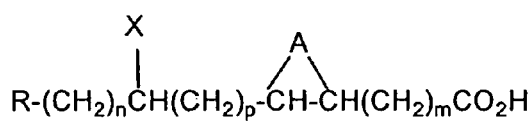
FIG. 2 depicts the general formula of a saturated fatty acid comprising a substituted radiolabel directly on the fatty acid backbone. This figure of a fatty acid variant comprises a generalized structure similar to the compound in FIG. 1.

The novel FAs described herein are radiolabeled and are modified with an organic substituent at 2,3; 3,4; 4,5; 5,6 and other sequence positions. The term "2,3" refers to the carbon bond between the carbon atoms located at position C2 and C3 (counting from the carboxyl carbon atom). As such, the related term "3,4" refers to the carbon atoms at positions C3 and C4. Likewise, the term "2,3" could also be interpreted by the skilled artisan to correspond to the term "beta-gamma" in reference to the carbon atoms, or "βγ". The related term "3,4" therefore, could be interpreted to correspond to the term "gamma-delta" in reference to the carbon atoms, or "γδ". The carboxyl end, of the molecule will hereinafter be referred to as the "right" end of the molecule, while the opposite end will be referred to as the "left" end of the molecule. Compounds can have the general formula, also depicted in FIGS. 2 and 4:

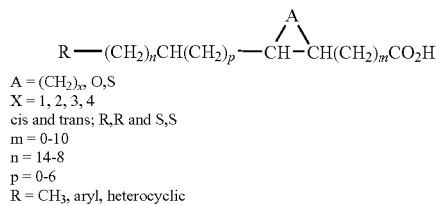

A = $(CH_2)_x$, O,S
X = 1, 2, 3, 4
cis and trans; R,R and S,S
m = 0-10
n = 14-8
p = 0-6
R = $CH_3$, aryl, heterocyclic In all of the preceding embodiments, the organic substituent may be saturated or unsaturated. The organic substituent may also comprise at least one heteroatom, advantageously N, O or S, most advantageously O or S, Nitrogen can also be used and it is well within the skill of the artisan to determine proper substitution of the nitrogen atom, as well as determining the appropriate biodistribution of the resultant analog. The carbon backbone of the fatty acid may also be substituted with at least one heteroatom herein defined.

It is further understood that A can be a $C_1$-$C_6$ alkyl, alkenyl or alkynyl, wherein one or more of the C atoms, advantageously 1, 2 or 3 C atoms, are substituted by a heteroatom, advantageously N, O or S, most advantageously O or S. It is well within the scope of one skilled in the art to determine proper placement of the nitrogen atom, in addition to determining the appropriate biodistribution of the resultant analog.

Further, "aryl" as herein defined may comprise, but is not limited to, a 5-, 6- or 7-membered ring. Further, "heteroatom" as herein defined may comprise, but is not limited to, 1, 2 or 3 heteroatoms.

The chain length of the FA also affects the tissue by which it is primarily taken up. Generally, a chain length of 12-20 carbon atoms, inclusive, is optimal for selective uptake by myocardial tissue, while the liver will selectively take up a chain length of 5-11 carbon atoms, inclusive. The carbon chain of the analog can be saturated or unsaturated. A preferred embodiment of the invention is a FA backbone that is saturated and has a cyclic organic substituent.

In another embodiment of the present invention, the FA backbone contains one or more vinyl groups, resulting in unsaturation of one or more carbon-carbon bonds. Preferably, the vinyl group or groups are placed on the opposite side of the carboxyl group, or to the left of the substituent designated by the letter 'A' in the general formula shown above. In another preferred embodiment, the vinyl groups are appended to the FA backbone such that the vinylic substituent is branched from the FA chain. More preferably, 1-6 carbon atoms separate the vinyl group(s) from the substituent designated by 'A'. Generalized drawings of these preferred embodiments are provided in FIGS. 6 and 8.

Activation of FAs is an energy-dependent step necessary for their transport into and sequestration within tissues of interest. Preferred embodiments of the instant invention are related to manipulation of the FA metabolism pathway, also referred to herein as "β-oxidation". This process begins with acyl-coenzyme A (CoA) synthase, which activates cytosolic free FAs by decarboxylation of the terminal COOH at the outer mitochondrial membrane in the presence of adenosine triphosphate (ATP). This forms an acyl-adenylate mixed anhydride, which reacts with CoA to form fatty acyl-CoA and AMP (adenosine monophosphate). One skilled in the art will know that different isoforms of acyl-CoA synthase are specific for FAs of varying chain lengths. In the context of this application, the term "CoA" is used synonymously with "ScoA".

Failure to activate FAs to acyl-CoA often results in "back-diffusion" into the vascular space and as a result, these back-diffused FAs are not metabolized. However, once activated, FAs can be "transported" across the inner mitochondrial membranes and undergo stepwise β-oxidation. Transport across the inner mitochondrial membrane is also referred to in the context of this application as "metabolic trapping" or "metabolic retention" of FAs. Activated fatty acyl-CoA cannot be directly transported across the inner mitochondrial membranes and the acyl chain must be transferred to carnitine by an acyl-carnitine/carnitine transporter. This facilitated diffusion through the inner mitochondrial membrane is the rate-limiting step for the oxidation of FAs. During high cardiac workloads or during myocardial ischemia, esterified FAs are diverted into storage pools as cytosolic triglycerides and membrane phospholipids. It is contemplated that activation of the novel analogs described by the invention and transport into the metabolizing tissue of interest occurs normally, but subsequent steps relating to disassembly of the analog are blocked.

Inside the mitochondrial matrix, FAs are metabolized in four steps. 1) Formation of a trans-2,3-double bond occurs through acyl-CoA dehydrogenase from a fatty acyl-CoA precursor to form trans-$\Delta^2$-enoyl-CoA. 2) The trans double bond is then hydrated by enoyl-CoA hydratase to form 3-L-hydroxyacyl-CoA, which is subsequently 3) dehydrogenated by 3-L-hydroxylacyl-CoA dehydrogenase to form β-ketoacyl-CoA. 4) Cleavage of the 2,3 carbon-carbon bond is facilitated through β-ketoacyl-CoA thiolase to form acetyl-CoA and a new acyl-CoA that is two carbons shorter than its starting molecule. This process is repeated for each remaining two-carbon fragment.

The present invention relates to FAs having a cyclic organic substituent that cause attenuation of the β-oxidation pathway by potentially preventing or blocking the metabolic sequence of one or several ways. For example, the intermediate is not a substrate for one of the enzymes required during the β-oxidation pathway or the intermediate cannot undergo a metabolic hydrogenation, dehydrogenation or hydroxylation step. An early trapping step that is related to flow and initial uptake may be advantageous for acquiring blood flow related images. Metabolic trapping or retention that occurs after one or several metabolic steps can represent the metabolic integrity of the target tissue. "Reducing" the formation of metabolic derivatives of the FAs of the invention can mean total or partial prevention or elimination of metabolic reactions such as, but not limited to, transport and back-diffusion, hydrogenation, dehydrogenation, hydroxylation, ketoacyl formation, and ketoacetyl elimination. As such, one aspect of the present invention reduces formation of β-ketoacyl-CoA (step 3). Yet another aspect reduces formation of a trans-$\Delta^2$-enoyl-CoA derivative (step 1). Still another aspect of the invention reduces formation of the products of subsequent β-oxidation steps, depending on the organic substituents and their placement on the FA backbone. The position of the organic substituent on the FA backbone can determine the extent of which the molecule undergoes β-oxidation and metabolism.

Modifications of the FA, such as the presence of unsaturated cis-double bonds, can also cause attenuation of FA metabolism. A cis-3,4-double bond is not a substrate for enoyl-CoA hydratase and requires enoyl-CoA isomerase, which mediates conversion of the cis double bond to the more stable, ester-conjugated trans form. Once this isomerization event occurs, metabolism occurs normally until the fifth round of β-oxidation, where the presence of another double bond at an even-numbered carbon atom results in formation of 2,4-dienoyl-CoA. This molecule is a poor substrate for enoyl-CoA hydratase and requires another enzyme, NADPH-dependent 2,4-dienoyl-CoA reductase. The resultant molecule, trans-2-enoyl-CoA, is further isomerized to yield trans-3-enoyl-CoA by 3,2-enoyl-CoA isomerase. Likewise, addition of other organic substituents, such as branched methyl or phenyl groups, take advantage of β-oxidation pathway attenuation, which can result in longer retention times in the metabolizing tissue of interest.

An embodiment of the present invention is substitution of an organic substituent or substituents on the FA chain backbone. This organic substituent can be placed at 2,3; 3,4; 4,5; 5,6 and other sequence positions, yielding the addition of the substituent at positions that are branched from the FA backbone. The position of the organic substituent on the FA backbone may determine the extent of which the molecule undergoes β-oxidation and metabolism. In a preferred embodiment, an organic substituent bonded at the 3,4 position causes the analog to be metabolically trapped in tissues of interest by substitution of CoA for the carboxyl carbon atom of the FA analog. The next two steps of metabolism of the resulting fatty acyl-CoA molecule, formation of trans-$\Delta^2$-enoyl-CoA and 3-L-hydroxyacyl-CoA derivatives, occur normally with 3,4-substitution. However, the resulting 3-L-hydroxyacyl-CoA derivative is not a substrate for 3-L-hydroxyacyl-CoA dehydrogenase due to the presence of the organic substituent and thus, β-ketoacyl CoA formation is prevented. In another preferred embodiment, an organic substituent bonded at the 2,3 position causes the analog to be metabolically trapped in tissues of interest by substitution of CoA for the carboxyl carbon atom of the FA analog. However, the first metabolic step, which involves dehydrogenation of the analog to ostensibly form a trans-$\Delta^2$-enoyl-CoA derivative, does not occur, thus preventing any further metabolism of the analog. It is contemplated that these specific embodiments can be used advantageously to measure blood flow.

Similarly, if an organic substituent is in position 4,5 and in other subsequent positions on the FA backbone (i.e. 5,6; 6,7; etc), one or more steps in β-oxidation may be completed and then be subsequently blocked. Yet another preferred embodiment of the invention contemplates appending an organic substituent at positions further on the FA backbone from the carboxyl-terminal end, such as but not limited to the 4,5; 5,6; 6,7 positions and so on. It will be apparent to those skilled in the art that the position of the organic substituent on the FA backbone will determine the extent of which the molecule undergoes β-oxidation. In this embodiment, metabolic activity of the instant invention can be advantageously measured due to its progression through the β-oxidation pathway.

Any organic substituent of the analog should be small enough to permit the formation of the first chemical intermediate involved in the fatty acid β-oxidation process; too large a substituent can alter the uptake and behavior of an analog to an undesirable extent. The chemical nature, as well as the size, of any substituent can affect the properties of the analog. Generally, an analog having a substituent which does not render the analog excessively polar, e.g., an unsubstituted alkyl group, is taken up primarily by the heart, while an analog containing a polarizing group, e.g., an alcohol or an ether, will be taken up primarily by the liver.

Figure 10:
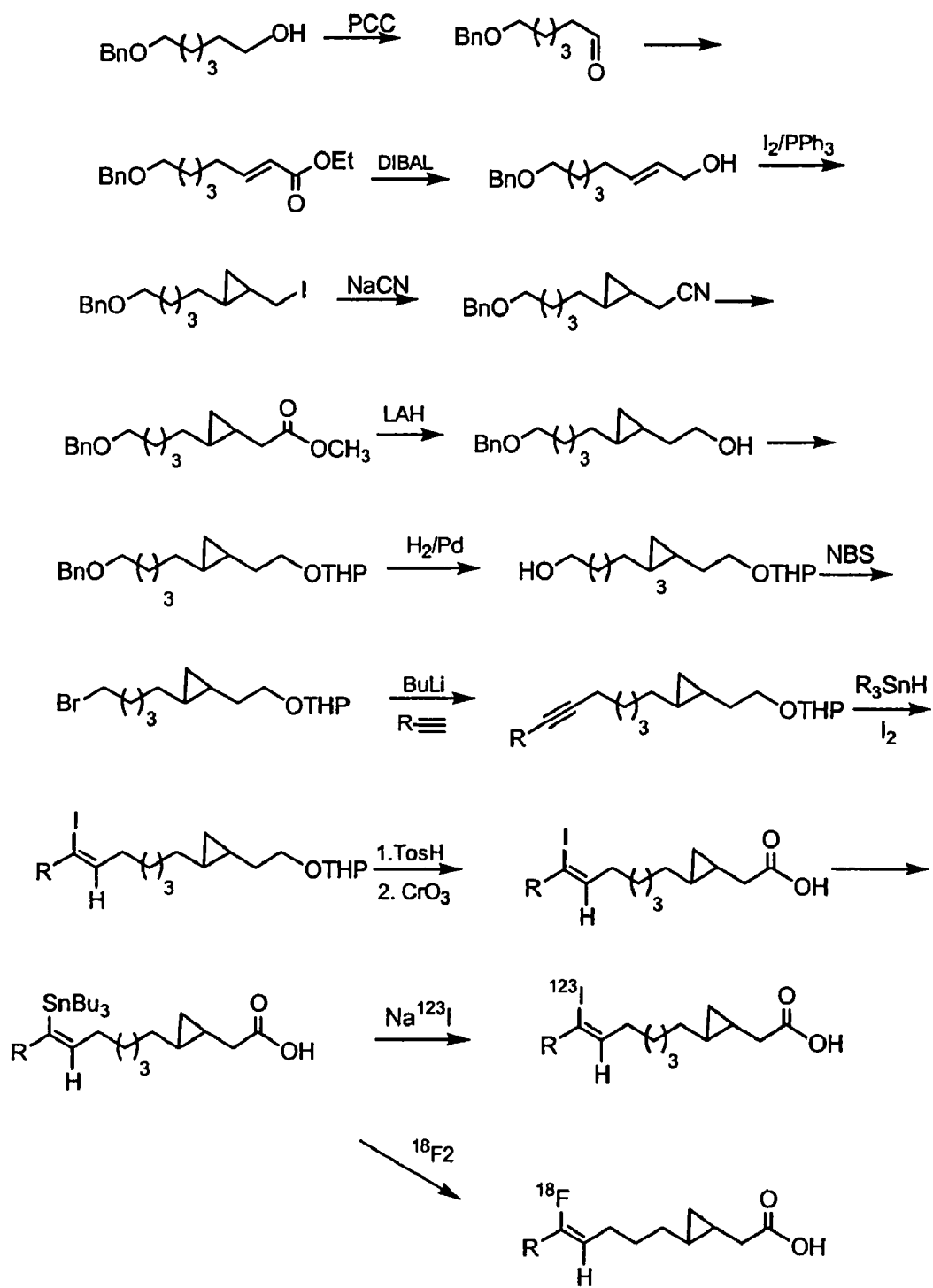
FIG. 10 is a schematic overview of the synthesis of endo-[$^{18}F$] fluoro- or [$^{123}I$]iodo-3,4-cyclopropylheptadecanoic acid.
Figure 11:
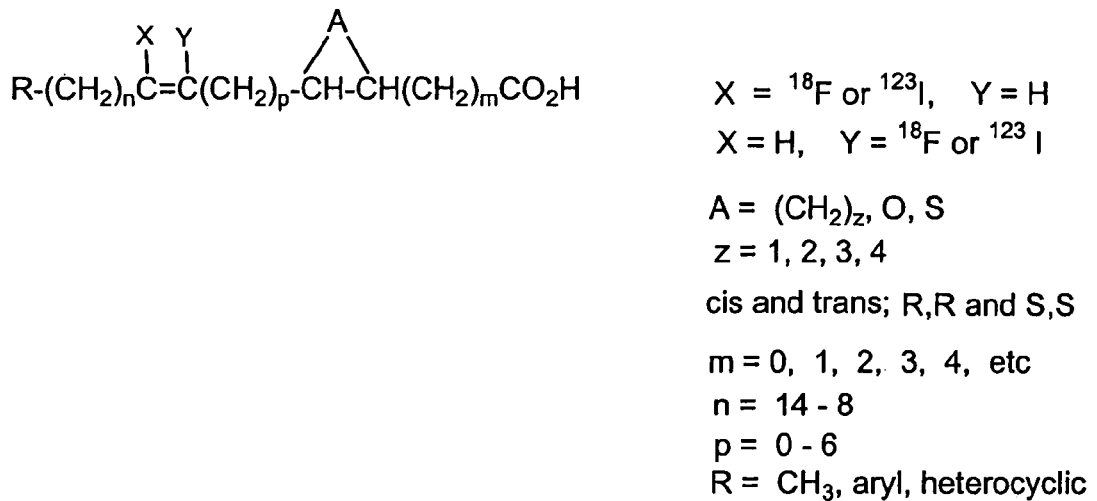
FIG. 11 depicts the general formula of a fatty acid comprising an endo-vinyl group. This endo-vinyl group can comprise a substituted radiolabel at substituents 'X' or 'Y'.

In yet another aspect of the present invention, the functional group designated by 'A' in the general formula provided above can comprise branched alkyl groups, dimethyl groups, cyclic alkanes such as cyclopropyl, cyclobutyl, cyclopentyl, or any 3 to 5-membered heterocyclic ring structure. The heterocyclic rings can contain nitrogen, sulfur or oxygen atoms. A preferred embodiment of the instant invention is a cyclopropyl ring substituent. Other preferred embodiments of the invention contemplate cyclobutyl and, cyclopentyl ring substituents, such as those described in the general diagram of FIG. 10.

Yet another object of the present invention contemplates that the organic substituent may be appended onto the FA backbone in either cis or trans form. A method of cyclopropanation (Simmons-Smith reaction) is described in the Examples section of this application and the improved procedure originates from Charette et al, *J. Org. Chem.* (1995) 60: 1081. The components of the reaction can be present as cis or trans isomer, depending on the FA precursor used for the addition of the cyclopropyl moiety. The cis diastereomer is preferentially synthesized by using 3 equivalents of the pre-formed complex of $Zn(CH_2I)_2 \cdot DME$ in $CH_2Cl_2$ (see Example 1 for details on this complex) and incubation for 3 hours at below $-10°$ C., whereas the cis isomer is made by using the cis olefin and the pre-formed complex and incubating the mixture for 2 hours at below $-10°$ C. One skilled in the art will understand that the cyclopropyl group on the FA backbone has two chiral centers and thus the molecule exists in two enantiomeric forms: R, R or S, S. An embodiment of the present invention encompasses each diastereomer and their respective enantiomers, as well as any racemic mixtures or meso compounds thereof.

The novel fatty acids according to the present invention can be radiolabeled with a positron or gamma-emitting label that is well known in the art. Preferred embodiments of the invention comprise $^{18}F$, $^{123}I$, $^{131}I$, $^{34m}Cl$, $^{75}Br$, $^{76}Br$ or $^{77}Br$. One of ordinary skill in the art will recognize that different radionuclides display different pharmacokinetic properties, such as elimination, clearance from and/or accumulation in biological tissues, and half-life ($t_{1/2}$). Radionuclides are typically synthesized by a cyclotron, which accelerates subatomic particles from an ion source along a circular orbit. Particle acceleration inside a chamber is controlled by two alternating electromagnetic fields. These accelerated particles can gain energy and collide with a target at close to the speed of light. Bombardment of particles against the target result in unstable, radioactive isotopes, which are then attached to biologically relevant molecules such as those exemplified by the instant invention. Alternatively, commercially available radionuclides are widely used and may be appended onto biologically relevant molecules by chemical synthesis techniques well known in the art. Typically, the half-lives of radiotracers used in imaging are relatively short, and thus many cyclotrons are key features of radiotracer detection apparatuses, such as PET and SPECT scanners, or gamma cameras. One skilled in the art will understand the principles of radioisotopic decay and this concept will not be discussed further in this application.

A preferred embodiment of the present invention is addition of a positron or gamma-emitting radiolabel at a position on the FA backbone that prevents significant loss of the radiolabel during FA metabolism and migration to other tissues. One of sufficient skill in the art will appreciate that radiolabeling at the terminal carboxyl group is not recommended, since this carboxyl group is removed by specific enzymes during the early metabolic stages of the FA into the tissues of interest. In one aspect of the invention, the radiolabel is added to the 9-carbon position of the FA backbone. In another aspect of the invention, the radiolabel is added to a terminal phenyl group on the FA backbone located on the opposing side from the carboxylic acid group. In yet another aspect of the invention, one or more carbon-carbon bonds on the FA backbone is unsaturated, resulting in a vinyl group and the radiolabel is appended directly to the vinyl group. In still another aspect of the invention, a radiolabeled vinyl group is appended onto the FA backbone and is branched from the FA backbone.

The radiolabeled FAs having a cyclic organic substituent can be synthesized by traditional organic chemical syntheses well known in the art. Similarly, the instant invention may be purified and analyzed by a variety of methods, including column purification, thin-layer chromatography (TLC), reverse-phase chromatography, high-performance liquid chromatography (HPLC), gas chromatography (GC), infrared spectroscopy (IR), nuclear magnetic resonance (NMR) including variations such as correlation spectroscopy (COSY), nuclear Overhauser effect spectroscopy (NOESY), and rotating frame nuclear Overhauser effect spectroscopy (ROESY), and Fourier Transform, other analytical techniques such as mass spectrometry (MS) and variations thereof, including electrospray, chemical ionization, matrix assisted laser desorption ionization, time-of-flight, fast atom bombardment/liquid secondary ionization, among many other techniques.

The pharmaceutical compositions comprising the present invention, novel radiolabeled FAs that have cyclic organic substituents, may be in a variety of conventional depot forms. These include, for example, solid, semi-solid and liquid dosage forms, such as tablets, pills, powders, liquid solutions or suspensions, liposomes, capsules, suppositories, injectable and infusible solutions. Such dosage forms may include pharmaceutically acceptable carriers and adjuvants, which are well known to those skilled in the art. These carriers and adjuvants include, for example, RIBI, ISCOM, ion exchangers, alumina, aluminum stearate, lecithin, serum proteins, such as human serum albumin, buffer substances, such as phosphates, glycine, sorbic acid, potassium sorbate, partial glyceride mixtures of saturated vegetable fatty acids, water, salts or electrolytes such as protamine sulfate, disodium hydrogen phosphate, sodium chloride, zinc salts, colloidal silica, magnesium trisilicate, polyvinyl pyrrolidone, cellulose-based substances, and polyethylene glycol. Adjuvants for topical or gel base forms may be selected from the group consisting of sodium carboxymethylcellulose, polyacrylates, polyoxyethylene-polyoxypropylene-block polymers, polyethylene glycol, and wood wax alcohols. The preferred form of the instant invention is an injectable form. Thus, this form may be subject to other treatments during preparation to improve their tolerance in subjects.

As stated above, the animal of interest, preferably a human can be injected with the radiolabeled FAs having a cyclic organic substituent. Any pharmaceutically acceptable dosage route, including parenteral, intravenous, intramuscular, intralesional or subcutaneous injection, may be used to administer the novel FA compositions of the instant invention. For example, the composition may be administered to the subject in any pharmaceutically acceptable dosage form including those which may be administered to a patient intravenously as bolus or by continued infusion over a period of hours, days, weeks, or months, intramuscularly—including paravertebrally and periarticularly—subcutaneously, intracutaneously, intra-articularly, intrasynovially, intrathecally, intralesionally, periostally, or by oral or topical routes. Preferably, the compositions of the invention are in the form of a unit dose and will usually be administered intravenously by bolus injection.

The purified FA can be contained in solutions such as saline, at concentrations suitable for intravenous delivery. These FAs can be complexed with albumin, a serum protein that binds to non-esterified FAs in the bloodstream. Typically albumin is added at a concentration of 2-10%, more preferably between 4-6%. Alternatively, these FAs can be emulsified in non-ionic detergents such as but not limited to, polyoxyethylene sorbitan monolaurate derivatives (Tween), Nonidet P-40, β-D-octylglucoside, ursodeoxycholic acid (UDCA), or Triton X-100, and resuspended in solutions containing or lacking albumin prior to injection. The dosages of radiolabeled cyclic substituted FA must be determined for each subject prior to administration, and the typical dosage ranges can be between 0.1-25 mCi, more preferably between 1-5 mCi.

In yet another aspect, the pharmaceutical compositions comprising the FAs according to the present invention may also be administered to any animal, including, but not limited to, horses, cattle, monkeys, birds, pet animals, such as dogs, cats, birds, ferrets, hamsters, rodents, squirrels, birds, and rabbits. The preferred embodiment of the invention is to monitor diseases or disease states associated with blood flow, FA metabolism or for imaging an organ of interest in a human.

The present invention further comprises methods to measure and/or identify changes in blood flow and metabolism in tissues of interest in response to disease states, exercise, pharmacological agents, or for diagnostic imaging.

In one embodiment of the instant invention, a method of measuring blood flow in a subject comprises the following steps:
 a) localizing a detectable amount of the FA composition of the invention, to a tissue of interest;
 b) detecting a signal from said radiolabeled FA composition in a tissue of interest within about 1 minute and about 5 minutes after administration;
 c) imaging a tissue of interest and;
 d) determining the rate of blood flow in a tissue of interest.

The present invention further provides a method of measuring metabolism in a subject comprising the following steps:
 a) localizing a detectable amount of the FA composition of the invention, to a tissue of interest and;
 b) detecting a signal from said radiolabeled FA composition in a tissue of interest within about 30 minutes and about 120 minutes after administration;
 c) imaging a tissue of interest and;
 d) determining the rate of metabolism in a tissue of interest.

Another embodiment of the present invention provides a method for retaining a fatty acid composition of the invention in a tissue of interest, comprising the steps of:
 a) localizing a detectable amount of the composition to the tissue;
 b) retaining the composition, or a metabolic derivative thereof, in the tissue by reducing transport and back-diffusion of the composition; and
 c) detecting the composition or the metabolic derivative in the tissue.

In another embodiment of the present invention, a method for retaining a fatty acid composition of the invention in a tissue of interest, comprising the steps of:
 a) localizing a detectable amount of the composition to the tissue;
 b) retaining the composition, or a metabolic derivative thereof, in the tissue by reducing dehydrogenation of the composition; and
 c) detecting the composition or the metabolic derivative in the tissue.

The present invention further provides a method for retaining a fatty acid composition of the invention in a tissue of interest, comprising the steps of:
 a) localizing a detectable amount of the composition to the tissue;
 b) retaining the composition, or a metabolic derivative thereof, in the tissue by reducing hydroxylation of the composition; and
 c) detecting the composition or the metabolic derivative in the tissue.

Another embodiment of the present invention provides a method for retaining a fatty acid composition of the invention in a tissue of interest, comprising the steps of:
 a) localizing a detectable amount of the composition to the tissue;
 b) retaining the composition, or a metabolic derivative thereof, in the tissue by reducing ketoacyl formation of the composition; and
 c) detecting the composition or the metabolic derivative in the tissue.

Yet another embodiment of the present invention provides a method for retaining a fatty acid composition of the invention in a tissue of interest, comprising the steps of:
 a) localizing a detectable amount of the composition to the tissue;
 b) retaining the composition, or a metabolic derivative thereof, in the tissue by reducing ketoacetyl elimination of the composition; and c) detecting the composition or the metabolic derivative in the tissue.

Numerous methods by which one may use the present invention in imaging, measurements of blood flow, and FA metabolism are contemplated, used singularly, or in combination with other imaging modalities. For example, cardiac imaging modalities generally measure two parameters: blood flow (perfusion) and myocardial viability (metabolism). These measurements are useful in numerous cardiac diseases. Animal models of measuring blood flow often use microspheres (Miller, D. D., et al. (1988) *Circ. Res.* 63: 681-692), however their use is precluded in humans, as microspheres can block circulation. Traditional methods of observing myocardial perfusion and metabolism have utilized two different tracers each separately used to measure either blood flow or metabolism. Widely used markers for blood flow are exemplified by $^{201}$Thallium ($^{201}$Tl), $^{99m}$Technetium ($^{99m}$Tc), $^{13}$N-Ammonia, and $^{82}$Rubidium. However, unlike $^{201}$Tl, $^{99m}$Tc, $^{13}$N-Ammonia, and $^{82}$Rubidium, the uses of which are only limited to measurements of perfusion, certain FA tracers are able to measure both flow and metabolism (Poe, N. D. et al. (1977) *Radiology* 124: 419-424; van der Wall, E. E. et al. (1980) *Eur. J. Nucl. Med.* 5: 401-405; Kairento, A. L. et al. (1988) *Nucl. Med. Biol.* 15: 333-338; Kawamoto, M. et al. (1994) *J. Nucl. Cardiol.* 1: 522-8; Kobayashi, H. et al. (1997) *J. Nucl. Med.* 39: 1117-1122; Miller, D. D., et al. (1988) *Circ. Res.* 63: 681-692).

Similarly, the instant invention can be used in a variety of methods to answer a specific diagnostic question. By way of example, methods can include administration of the invention under conditions of rest and/or stress induced by exercise, disease states, or pharmacological agents. Likewise, the radiolabeled FAs having a cyclic organic substituent can also be used in sequential imaging experiments, depending on the radioisotope used. Blood flow to an organ of an animal can be determined within 1 second to about 10 minutes, preferably between about 1 minute and about 5 minutes after the radiolabeled cyclic substituted FA is administered to the animal. Metabolism by the organ of interest can be determined within a time period between about 10 minutes to about 24 hours, preferably between about 30 minutes and about 120 minutes after administration of the radiolabeled FA into the bloodstream of the animal.

Nuclear cardiac imaging using the present invention can be used to detect a wide variety of cardiac derangements. One of sufficient skill in the art will recognize that cyclic substituted, radiolabeled FAs can be used singularly as a marker for blood flow and for cardiac metabolism, or may be used in combination with another tracer. Such tracers include, but are not limited to $^{13}$N-Ammonia, $^{57}$Co-Cyanocobalamin, $^{59}$Fe-Ferrous Citrate, $^{18}$F-Fluorodeoxyglucose, $^{67}$Ga-Gallium Citrate, $^{111}$In-Indium Oxyquinoline, $^{111}$In-Indium Pentetate, $^{111}$In-Indium Pentetreotide, $^{111}$In-Indium Satumomab Pendetide, Radioiodinated Iobenguane, $^{123}$I-Iodohippurate Sodium, $^{131}$I-Iodohippurate Sodium, $^{123}$I-Iofetamine, $^{125}$I-Iothalamate Sodium, $^{81}$Krypton, $^{11}$C-Methionine, Radioiodinated-Albumin, $^{82}$Rubidium, Sodium $^{51}$Chromate, Sodium $^{18}$Fluoride, Sodium $^{123}$Iodide, Sodium $^{131}$Iodide, Sodium $^{99m}$-Pertechnetate, $^{99m}$Tc-Albumin, $^{99m}$Tc-Albumin (Aggregated), $^{99m}$Tc-Albumin (Colloidal), $^{99m}$Tc Arcitumomab, $^{99m}$Tc-Bicisate, $^{99m}$Tc-Disofenin, $^{99m}$Tc-Exametazime, $^{99m}$Tc-Gluceptate, $^{99m}$Tc-Lidofenin, $^{99m}$Tc-Mebrofenin, $^{99m}$Tc-Medronate, $^{99m}$Tc Mertiatide, $^{99m}$Tc-Nofetumomab Merpentan, $^{99m}$Tc-Oxidronate, $^{99m}$Tc-Pentetate, $^{99m}$Tc-Pyrophosphate, $^{99m}$Tc-(Pyro- and trimeta-) Phosphates, $^{99m}$Tc Sestamibi, $^{99m}$Tc Succimer, $^{99m}$Tc-Sulfur (Colloidal), $^{99m}$Tc-Teboroxime, $^{99m}$Tc-Tetrofosrnin, $^{201}$Thallousi Chloride, $^{127}$Xenon, $^{133}$Xenon. It will be apparent that not all of the aforementioned tracers are suitable for cardiac imaging and that use of the instant invention is not necessarily limited to those related to cardiovascular disease.

The tissues of interest can be any tissues that utilize FAs as a source of energy. The tissues can be, but are not limited to, cardiac tissue, brain, liver, bone, spleen, lung, blood, kidney, gastrointestinal, muscle, and adrenal tissue. A preferred embodiment of the present invention is cardiac tissue. Another preferred embodiment can also encompass liver tissue.

Cardiac diseases or disease states that can be monitored using radiolabeled FAs having cyclic organic substituents include, but are not limited to, acute myocardial infarction, unstable angina, chronic ischemic heart disease, coronary artery disease, myocarditis, dilated, hypertrophic, and restrictive cardiomyopathies, congenital heart diseases, hypertensive heart disease, post-transplant heart disease, allograft vasculopathies, valvular heart disease, and pharmacologically induced conditions such as doxorubicin cardiotoxicity. It is contemplated that methods of use of radiolabeled FAs exemplified by the present invention will be modified according to the particular disease examined.

The instant invention can also be used in numerous non-cardiac disease states described herein, such as: abscess and infection; biliary tract blockage; blood volume studies; blood vessel diseases; blood vessel diseases of the brain; bone diseases; bone marrow diseases; brain diseases and tumors; cancer and neoplasms; colorectal disease; diabetes; disorders of iron metabolism and absorption; heart disease; heart muscle damage such as infarction and ischemia; impaired flow of cetebrospinal fluid in brain; kidney diseases; liver diseases; lung diseases; parathyroid diseases and/or parathyroid cancer; pernicious anemia and/or improper absorption of vitamin $B_{12}$ from intestines; fed blood cell diseases; salivary gland diseases; spleen diseases; stomach disorders and intestinal bleeding; tear duct blockage, thyroid diseases and/or thyroid cancer, urinary bladder diseases. A preferred embodiment of the present invention is its use in detecting cardiac myopathies by measuring blood flow and FA metabolism. It is understood that diagnosis of the aforementioned diseases will often require the use of other radiotracers, also described above. It is apparent that use of the instant invention is not only limited to detection of diseased states, but also for diagnostic imaging in healthy subjects.

One of ordinary skill in the art will appreciate the numerous methods of detecting cardiac imaging agents exemplified by the present invention, as well as understand that different radionuclides will require different detection techniques. Positron Emission Tomography (PET) and Single Photon Emission Computed Tomography (SPECT) are imaging techniques in which a radionuclide is synthetically introduced into a molecule of potential biological significance, such as a radiolabeled FA indicated by the instant invention. The subsequent uptake of the radiotracer is measured over time and used to obtain information about the physiological process of interest. While PET and SPECT rely on similar principles to produce their images, important differences in instrumentation, radiochemistry, and experimental applications are dictated by inherent differences in their respective physics of photon emission.

Unstable nuclides that possess an excess number of protons may take one of two approaches in an effort to reduce their net nuclear positivity. In one radioactive decay scheme, a proton is converted to a neutron and a particle called a positron is emitted (Hoffman, E. J., and Phelps, M. E. New York: Raven Press; 1986: 237-286; Sorenson, J. A., and Phelps, M. E. Philadelphia: W.B. Saunders; 1987). Of identical mass but opposite charge, positrons are the antimatter equivalent of electrons. When ejected from the nucleus, a positron collides with an electron, resulting in the annihilation of both particles and the release of energy. Two γ photons are produced, each of equivalent energy and opposite trajectory (generally 180° apart).

The unique spatial signature of back-to-back photon paths is exploited by PET scanners in locating the source of an annihilation event, a method known as coincidence detection (Hoffman, E. J., and Phelps, M. E. New York: Raven Press; 1986: 237-286; Links, J. M. New York: Raven Press; 1990: 37-50). PET (and SPECT) scanners employ scintillation detectors made of dense crystalline materials (e.g., bismuth germanium oxide, sodium iodide, or cesium fluoride), that capture the high-energy photons and convert them to visible light. This brief flash of light is converted into an electrical pulse by an adjacent photomultiplier tube (PMT). The crystal and PMT together make up a radiation detector. A PET camera is constructed such that opposing detectors are electronically connected. Thus, when separate scintillation events in paired detectors coincide, an annihilation event is presumed to have occurred at some point along an imaginary line between the two. This information is used to reconstruct images using the principles of computed tomography. Conversely, single events are ignored. Although it is conceivable that two unrelated photons from spatially separate annihilation events might reach opposing detectors in unison, these accidental coincidences are much less frequent than true ones. Nevertheless, random coincidences constitute a source of background noise in PET images (Hoffman E J et al. *J Comput Assist Tomogr* (1981); 5:391-400; Hoffman, E. J., and Phelps, M. E. New York: Raven Press; (1986): 237-286; Links, J. M. New York: Raven Press; (1990): 37-50).

The skilled artisan will recognize the intrinsic limitations of PET derive from the nature of positron decay and the principle of coincidence detection. Specifically, PET recognizes the site of positron annihilation, which does not necessarily coincide with the site of radioactive decay. Annihilation often occurs some distance away from the positron's origin. The distance separating these two events, decay and annihilation, depends on the average kinetic energy of the positron as it leaves the nucleus, and varies according to the specific isotope involved (Phelps M E, et al. *J Nucl Med* (1975); 16: 649-652). In addition, if the positron is not entirely at rest at annihilation, photons will be emitted at an angle slightly different than 180°. Taken together, remote positron annihilation and photon non-colinearity place a theoretical limit on PET's achievable spatial resolution (Links J M. New York: Raven Press; (1990): 37-50).

In another embodiment of the present invention, isotopes that decay by electron capture and/or γ emissions can be directly detected by SPECT. Certain proton-rich radionuclides, such as $^{123}$I and $^{99m}$Tc, may instead capture an orbiting electron, once again transforming a proton to a neutron (Sorenson J A, and Phelps M E. Philadelphia: W.B. Saunders; 1987). The resulting daughter nucleus often remains residually excited. This meta-stable arrangement subsequently dissipates, thereby achieving a ground state and producing a single γ photon in the process. Because γ photons are emitted directly from the site of decay, no comparable theoretical limit on spatial resolution exists for SPECT. However, instead of coincidence detection, SPECT utilizes a technique known as collimation (Jaszczak R J. Boca Raton: CRC Press; (1991): 93-118). A collimator may be thought of as a lead block containing many tiny holes that is interposed between the subject and the radiation detector. Given knowledge of the orientation of a collimator's holes, the original path of a detected photon is linearly extrapolated and the image is reconstructed by computer-assisted tomography.

It is contemplated that use of the instant invention will require processing and analysis of data obtained from imaging modalities such as but not limited to PET or SPECT. The following mathematical algorithms can determine the rate of uptake of novel radiolabeled FA analogs having a cyclic organic substituent. Other mathematical models can also be similarly employed and/or modified to determine the rate of blood flow and metabolic activity (Sokoloff, L. et al (1977) *J. Neurochem.* 28: 879-916; Elmaleh, D. R. et al. (1994) *J. Nucl. Med.* 35: 496-503; Marshall, R. C. et al. (1998) *Am. J. Physiol.* 275: H668-H679; Wieler, H. et al. (1990) *Nuc. Med. Commun.* 11: 865-878). The collected early and late images in tissues of interest can be manipulated to obtain values that may indicate abnormalities.

Mathematical modeling can be used to assess the rate of uptake of FA analogs of the present invention. There is a reproducible relationship between the net extraction fractions of native FA and FA analog. Assuming the uptake and metabolism of native FA is in a steady state, the rate of metabolism, defined as R for purposes of this application, can be deduced from the Fick equation:

$$R = E_n * F * Ca \text{ (mol/min/g)}$$

where
$E_n$=net extraction fraction
F=blood flow (ml/min/g), which can be estimated from the early images.
Ca=arterial concentration of FA (mol/nl).

The assumption is such that at steady state, the rate at which FA leaves the tissue through oxidation must be equal to the rate at which FA is entering the tissue from the blood. The net extraction of a substance metabolized by the heart in a steady state can be determined from the arterial or arterialized blood and venous blood concentrations of FAs.

A relationship between the net extraction of FA analog and FA, $E_n$(FA analog), can be used to calculate the rate of FA metabolism, R. We can write this relationship as $$L = E_n / E_n (FA \text{ analog})$$

L here plays the same role as the "lumped constant" in Sokoloff's model for deoxyglucose metabolism (Sokoloff, L. et al (1977) *J. Neurochem.* 28: 879-916). The difference between the two models is that L may not be constant. 'L' can vary with blood flow, free fatty acid concentration, FFA composition, or other physiological parameters. The behavior of L is best understood by performing a series of experiments to determine the relationship between $E_n$ and $E_n$[FA analog] in different physiological states.

Basic modeling assumptions are such that 1) fatty acid uptake and metabolism is in a steady state. In other words, all the FA pools and reaction products have constant concentrations. This assumes that the net rate at which FA is removed from the blood equals the rate of FA catabolism. (2) Labeled FA analog is generally present in trace amounts, so that its presence does not alter the FA steady state. The various transport and chemical reaction rates for FA analog can then be expected to depend linearly on the concentrations of the FA analogs. This modeling approach accounts for capillary-tissue exchange as well as for intracellular metabolism of the administered FA analog. Intracellular metabolism of native fatty acids is assumed to create gradients, which regulate the access of FA analog to the intracellular space. Coupled to these metabolically induced gradients are the effects of blood flow and capillary transport properties. In this approach, flow and transport mechanisms are included in capillary tissue exchange while the metabolic processes are included in intracellular metabolic parameters.

In general, the transport of any substance between capillary and tissue depends on two factors: (i) Intrinsic capillary transport rate for a freely diffusing substance (or the permeability surface area product; for carrier mediated transport, it is a function of "apparent" Michaelis-Menten parameters that describe the transport process). In a "microscopic" modeling approach, a protein-substrate complex would characterize each barrier, but here they are lumped together into a single "apparent" rate parameter (k). (ii) Local blood flow per ml of tissue. Blood flow and transport rate can be thought to describe two competing processes, one carrying molecules through the capillary wall, the other carrying them out the venous end of the capillary. These two rates are combined to give extraction fraction E, the fraction of molecules entering a capillary bed, which pass through the wall of the capillary at least once. As used here, E is the one-way (unidirectional) extraction fraction, not the net extraction fraction.

It is assumed that an FA analog cannot undergo β-oxidation, and hence, is either trapped in mitochondria or incorporated in the triglyceride pool. The triglyceride pool turns over very slowly. With respect to FA analog, the concentration of FA analog in myocardial tissue, following IV injection, can reach a plateau after ten to fifteen minutes. The simplest model consistent with the measured tissue curves and the biochemical data is one in which tissue is described by two compartments, a precursor FFA pool and a metabolically trapped pool, both driven in response to the FA analog concentration in the blood plasma.

Because FA analogs cannot undergo β-oxidation and because the turnover rate for the triclyceride pool is slow, the plateau of the tissue curve can reflect both components. Measurements with FA analogs can only determine the rate at which FA analog passes through the committed step to acyl-CoA. Accordingly, the steady state rate for incorporation into triglyceride plus β-oxidation can be measured. This situation is analogous to the result that would be obtained if Fick-type atrial/ventricular measurements with a native fatty acid such as palmitate could be made.

Based on the considerations outlined above, an operational equation capable of describing the PET measurements in terms of the blood flow is described, F being the unidirectional extraction fraction, E as the net extraction fraction, $E_n$, and the rate K, with which FA analog is cleared from the "precursor pool". The rate constant K is the sum of two rates, $K_2$ the rate of back-diffusion, and $K_3$, the rate of activation of FA analog to the CoA form. Neglecting tracer in blood, the operational equation is given as $$C(t)=F*[(E-E_n)*\mathrm{Exp}(-K*t)+E_n](*)Ca(t)$$

Where C(t) is the tissue concentration at time t,

Ca(t) is the plasma concentration at time t and (*) represents the mathematical operation of convolution.

For the model of this invention, $E_n=E*K3/K2+K3$. This expression has a simple interpretation-i.e., E is the probability a FA analog molecule will leave the blood on a single capillary transit, K3/(K2+K3) is the probability that a FA analog molecule entering the tissue will be metabolically trapped. No assumptions were made in the derivation of the operational equation limiting the value of E, other than it be in the range (0.1). It should also be noted that the operational equation is formally similar to that of Sokoloff.

Under the assumption that a steady state was established with respect to the consumption of FA analog, where the plasma FA content was the concentration of FA analog, then the analog's metabolic rate would be $F*E_n$[FA analog]. Therefore, the quantity $F*E_n$ can be interpreted as the analog utilization rate to a unit quantity of FA analog in steady state.

Analysis of the operational equation of the method shows that as t (or, the plateau concentration is given by $F*E_n*f$ of the plasma concentration curve). Thus, the tissue concentration at the plateau is directly proportional to the metabolism of the analog.

A better understanding of the instant invention and of its many advantages will be facilitated via the following examples, which further describe the invention and given by way of illustration. The examples that follow are not to be construed as limiting the scope of the invention in any manner. In light of the present disclosure, numerous embodiments within the scope of the claims will be apparent to those of ordinary skill in the art.

EXAMPLES

Example 1

Synthesis of $^{18}$F-labeled
3,4-cyclopropyl-heptadecanoic acid ([$^{18}$F]-FCPHA)

Synthesis of [$^{18}$F]-FCPHA was performed using the following method. PCC (pyridinium chlorochromate; 24.8 g, 115.2 mmol) was slowly added in portions to a solution of 6-benzyloxy-1-hexanol (20 g, 96 mmol) in 200 ml of methylene chloride at room temperature (25° C., RT). The black mixture was stirred for 2 hours, and filtered through 50 g of silica gel. The solvent was removed and the crude oil was separated chromatographically on silica gel using a mixture of hexane:ethyl acetate at a ratio of 90:10. This yielded the aldehyde equivalent, 6-benzyloxy-1-hexanal, at a scale of 14 g (70%).

Under a nitrogen atmosphere, octyl bromide (12 g, 115 mmol) in anhydrous ether (60 mL) was added to magnesium metal (2.8 g, 116 mmol) in 10 ml of ether at a rate as to maintain gentle reflux. After addition, the reaction mixture was stirred for 1 hour and then 6-benzyloxyhexanal (12 g, 58 mmol) in 20 ml of ether was added dropwise to the reaction mixture at RT. The mixture was stirred for 4 hours and poured over ice water. Acidification was achieved with 10% hydrochloric acid (HCl), then extracted with ether. The combined extracts were washed with brine, dried, and the solvent removed. Chromatography of the crude oil on silica gel using hexane:ethyl acetate at a ratio of 80:20 yielded 16.5 g, or 89%, of the alcohol. The chemical shift of the compound, detected by $^1$H-NMR, was as follows: $^1$H NMR (CDCl$_3$) δ 0.89 (t, 3H, CH$_3$), 1.2-1.7 (m, 22H, CH$_2$), 3.45 (m, 2H, CH$_2$O), 3.55 (m, 1H, CH—O), 4.55 (s, 2H, CH$_2$—O), 7.35 (m, 5H, benzyl).

The resulting compound, 1-benzyloxy-6-tetradecanol (16 g), was hydrogenated overnight using 100 mg of 10% palladium on activated carbon (Degussa A G; Frankfurt, Germany) in 100 ml of methanol to yield 1,6-tetradecandiol (11.1 g, 4.85 mmol). This diol compound, in 100 ml of methylene:pyridine (9:1), was treated with trityl chloride (13.5 g, 4.85 mmol). The mixture was stirred for 4 hours, then washed with ice-cold 10% HCl until the aqueous phase was acidic. Washing in brine then followed this until the aqueous phase was neutral. Solvent removal and chromatography on silica gel in hexane:ethylacetate (80:20) of the oil gave 20.1 g (87%) of the trityl alcohol. The chemical shift of the compound, detected by $^1$H-NMR, was as follows: $^1$H-NMR (CDCl$_3$) δ 0.89 (t, 3H, CH$_3$), 1.2-1.7 (m, 22H, CH$_2$), 3.05 (m, 2H, CH$_2$O), 3.55 (m, 1H, CH—O), 3.55 (m, 1H, CH—O), 7.2-7.5 (m, 15H, benzyl).

The resulting compound, 1-trityl-6-tetradecanol (20 g, 42.3 mmol), was slowly mixed with 60% sodium hydride (2 g, 50 mmol) and benzyl bromide (7.2 g, 42.3 mmol) in dry dimethylformamide (DMF; 100 ml) in a water bath set at RT. The mixture was stirred for 4 hours at RT and poured into ice water, then extracted with ether. Chromatography of the crude oil on silica gel using hexane:ethyl acetate (90:10) yielded 19 g (34 mmol), or 80% of the diether compound, 6-benzyloxy-1-trityl-tetradecane diether. This diether compound was mixed with 100 mg of p-toluene sulfonic acid in methanol (100 L) at RT for 4 hours. Sodium bicarbonate (100 mg) was added and the solvent removed by rotary evaporation. The oil was separated by chromatography on silica gel in hexane:ethyl acetate (80:20) yielded 7.5 g, or 90% of the alcohol. The chemical shift of the resulting compound, 6-benzyloxy-1-tetradecanol, is as follows: $^1$H-NMR (CDCl$_3$) 8-0.89 (t, 3H, CH$_3$), 1.2-1.7 (m, 22H, CH$_2$), 3.38 (m, 2H, CH$_2$O), 3.55 (m, 1H, CH—O), 4.7 (s, 2H, CH$_2$—O), 7.35 (m, 5H, benzyl).

PCC (9.7 g, 45 mmol) was added in portions to a solution containing 6-benzyloxy-1-tetradecanol (7.5 g, 30 mmol) in methylene chloride (100 ml) at RT. The black mixture was stirred for 2 hours, then filtered through a bed of silica gel using hexane:ethyl acetate (90:10). The corresponding aldehyde, 6-benzyloxy-tetradecanal, was produced at a yield of 6.1 g (81%). This aldehyde compound was mixed with carbethoxymethylene triphenylphosphorane (10 g, 29 mmol) in 100 ml of methylene chloride at RT. The mixture was allowed to stir overnight, after which the solvent was removed and replaced with hexane. Solid precipitates were removed by filtration. Following chromatography on silica gel using hexane:ethyl acetate at a ratio of 90:10, the corresponding ester was detected at 8.4 g scale (90%). The chemical shift of the ester, 8-benzyloxyhexadec-2-enoate ethyl ester, is as follows: $^1$H-NMR (CDCl$_3$) δ 0.89 (m, 6H, CH$_3$), 1.2-1.5 (m, 20H, CH$_2$), 2.2 (m, 2H, CH$_2$—C=), 3.35 (m, 2H, CH$_2$O), 4.2 (q, 2H, MeCH$_2$—O), 4.55 (dd, 2H, CH$_2$—O), 5.8 (d, 1H, CH=C), 6.95 (d,t 1H, CH=C), 7.35 (m, 5H, benzyl).

DIBAL (diisobutylaluminum hydride; 8 ml, 44 mmol) in 40 ml hexane, was added dropwise to the ester compound 8-benzyloxyhexadec-2-enoate ethyl ester (8.4 g, 22 mmol) in 40 ml methylene chloride at −78° C. The mixture was allowed to reach 0° C. and 5 ml of ethyl acetate was added dropwise, followed by ice. The resultant slurry was acidified with 10% HCl, followed by ether extraction. The combined ether extracts were washed with brine, dried, and the solvent was removed. Separation of the crude oil by silica gel chromatography using hexane:ethyl acetate (80:20) yielded 6.7 g, or 90% of the unsaturated primary alcohol.

Addition of the cyclopropyl moiety was performed essentially as described by Charette and coworkers (Charette et al, J. Org. Chem. 1995 60: 1681). A 100-ml round bottom flask containing 40 ml of dry methylene chloride was cooled to −25° C. and placed under a nitrogen atmosphere. To this flask, 3.8 ml of diethyl zinc, followed by 3.9 ml of 1,2-dimethoxyethane (DME), was added. Diiodomethane (6 ml) was added dropwise to the solution, while maintaining the reaction temperature between −25° C. and −10° C. This solution was then added by double-ended needle, to a solution containing 8-benzyloxyhexadec-2-enol (2 g, 5.8 mmol), dioxaborolane (made from (+)N,N,N',N'-tetramethyl-L-tartaramide and butylboronic acid), and 300 mg of 4 Å molecular sieves in methylene chloride (40 ml) under nitrogen at −40° C. and −30° C. The reaction mixture was stirred for 2 hours at −25° C., then allowed to warm to 0° C. Saturated ammonium chloride in an 80 ml volume was added to the mixture, then stirred at RT for 16 hours. Solid matter was removed by filtration and the layers were separated. The aqueous layer was extracted with methylene chloride, while organic layers were pooled, washed with water, and dried. The crude oil was separated by silica gel chromatography in hexane:ethyl:acetate (90:10), yielding 1.9 g (90%) of the cyclopropyl alcohol.

This reaction was repeated twice. The chemical shift of the molecule, 8-benzyloxy-2,3-cyclopropylhexadecanol, is as follows: $^1$H-NMR (CDCl$_3$) δ 0.3 (m, 2H, ring CH$_2$), 0.5 (m, 1H, CH), 0.75 (m, 1H, CH), 0.89 (t, 3H, CH$_3$), 1.2-1.6 (m, 22H, CH$_2$), 3.35 (m, 1H, CHO), 3.45 (m, 2H, CH$_2$—O), 4.55 (s, 2H, CH$_2$-0), 7.35 (m, 5H, benzyl). Addition of dioxaborolane in this reaction will form the S,S isomer as the predominant species. The reaction can be performed without dioxaborolane to yield the racemic (R,R; S,S) mixture.

Iodine (6 g, 24 nmol) was added in portions to a solution containing 8-benzyloxy-2,3-cyclopropylhexadecanol (5.7 g, 15.8 mmol) and triphenylphosphine (6.2 g, 23.7 mmol) in 100 ml of dimethylformamide. The dark red mixture was combined with 100 ml of 10% sodium thiosulfate and extracted with ether. The combined extract was washed with water, brine, and the solvent was subsequently removed. Silica gel chromatography in hexane:ethyl acetate (95:5) yielded 4.5 g (60%) of the alkyl iodide. This alkyl iodide, 8-benzyloxy-1-iodo-2,3-cyclopropylhexadecane (4.5 g, 9.6 mmol), and sodium cyanide (0.95 g, 19.2 mmol) in 60 ml of dimethyl sulfoxide (DMSO), was heated to 80° C. for 2 hours. The mixture was poured into 100 ml of water, followed by ether extraction. The combined extract was washed with water, dried, and solvent removed. The crude oil was separated by silica gel chromatography in hexane:ethyl:acetate (80:20) and yielded 3.0 g (87%) of the corresponding nitrile compound. Chemical analysis by $^1$H-NMR resulted in: $^1$H NMR (CDCl$_3$) δ 0.3 (m, 2H, ring CH$_2$), 2.4 (m, 2H, CH$_2$—CN), 3.35 (m, 1H, CHO), 4.55 (s, 2H, CH$_2$—O), 7.35 (m, 5H, benzyl).

A mixture containing the above-described nitrile compound, 9-benzyloxy-2,3-cyclopropylhexadecane nitrile (3.0 g, 8.1 mmol), 600 mg of potassium hydroxide (KOH), and 3 drops of water in 40 ml ethylene glycol, was heated for 6 hours at 170° C. Once cooled, the mixture was diluted with 80 ml of 10% HCl, then extracted with ether. The combined extract was dried and the solvent was removed. The crude carboxylic acid was treated with diazomethane (generated from N-methyl-N'-nitro-N-nitrosoguanidine and 40% KOH in ether). The reaction mixture was stirred for 1 hour before solvent removal. Chromatography of the crude oil on silica gel with hexane:ethyl acetate (80:20) gave 1.9 g, or 60%, of the corresponding ester, 9-benzyloxy-3,4-cyclopropylheptadecanoate methyl ester (4.7 mmol). This ester was hydrogenated overnight with 25 mg of 10% palladium on activated charcoal in 50 ml of methanol. Hydrogenation yielded 1.3 g, or 89% of the hydroxy ester. Chemical analysis resulted in the following: $^1$H-NMR (CDCl$_3$) δ 0.30 (d,d, 2H, ring CH$_2$), 0.53 (m, 1H, CH), 0.75 (m, 1H, CH), 0.89 (t, 3H, CH$_3$), 1.2-1.6 (m, 22H, CH$_2$), 2.23 (m, 2H, CH$_2$—CO), 3.58 (m, 1H, CHO), 3.69 (s, 3H, CH$_3$).

The hydroxy ester, 9-hydroxy-3,4-cyclopropylheptadecanoate methyl ester (0.5 g, 1.6 mmol), and methane sulfonyl chloride (0.2 g, 1.76 mmol), and 10 mg of DMAP (4-dimethylaminopyridine) in 20 ml of methylene chloride:pyridine (90:10), was stirred for 2 hours. The mixture was washed with 10% HCl until the aqueous layer was acidified, then washed again with 10% NaHCO$_3$. Chromatographic analysis of the crude oil on silica gel, in methylene chloride:methanol (95:5) gave 0.5 g (83%) of the mesylate ester, 9-hydroxy-3,4-cyclopropylheptadecanoate methyl ester.

Figure 1:
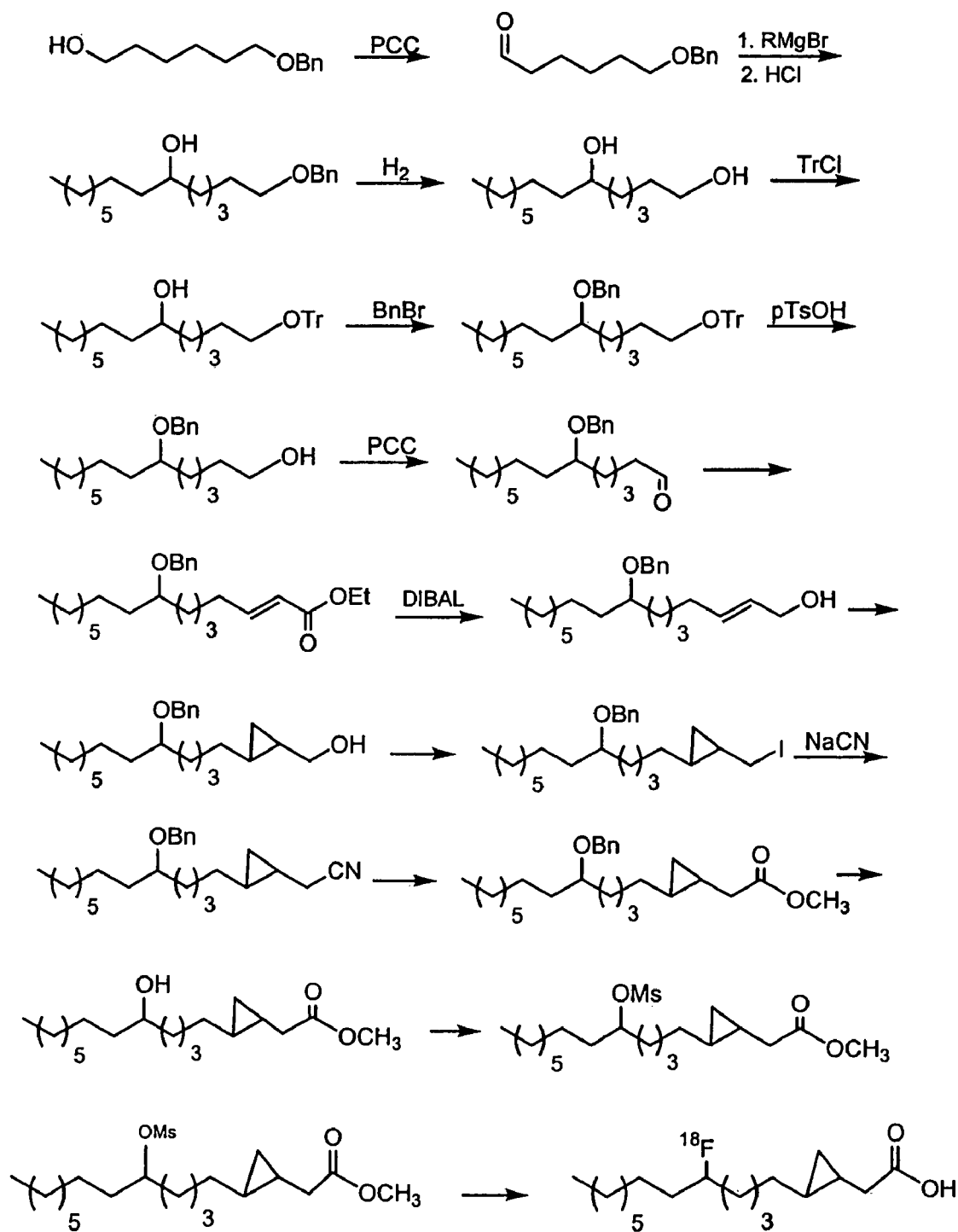
FIG. 1 is a schematic overview of the synthesis of [$^{18}F$]-9-fluoro-3,4-cyclopropyl-heptadecanoic acid.

The radiolabel $^{18}$F, contained in water (60 mCi, 1 ml), was added to a vial containing 10 mg of Kryptofix-222 (4,7,13, 16,21,24-hexaoxa-1,10-diazabicyclo[8.8.8]hexacosane; Merck, Whitehouse Station, N.J.) and 4 mg of K$_2$CO$_3$. Water was removed using a stream of nitrogen at 115° C., followed by the three rounds of addition of acetonitrile (2 ml). The mesylate ester, 9-hydroxy-3,4-cyclopropylheptadecanoate methyl ester (10 mg) in 1 ml of acetonitrile was combined with the radiolabel mixture and heated for 10 minutes in 120° C. This yielded the $^{18}$F-labeled ester at 80% yield after silica Sep-Pak purification (Waters Corporation, Milford, Mass.) in hexane:ethyl acetate (85:15). The labeled ester was placed in a vial and the solvent was removed. It was replaced with 0.1 ml of 1M lithium hydroxide (LiOH) and 0.3 ml of methanol. The reaction vial was heated to 60° C. for 20 minutes. Methanol was removed by nitrogen stream at 60° C. The solution was acidified in 10 ml of 10% HCl, and the mixture was extracted twice with 10 ml of ether. The combined ether extract was passed through a silica Sep-Pak chromatography cartridge and solvent was removed, affording 13 mCi of the final product, 9-[$^{18}$F]-fluoro-3,4-cyclopropylheptadecanoic acid. Radio thin-layer chromatography (TLC) showed 94% radiochemical purity (silica gel plate, 25:75 ethyl acetate/hexane, $R_f$=0.40) with the remaining activity as unhydrolyzed ester (silica gel plate, 15:85 ethyl acetate/hexane, $R_f$ 0.80). A schematic representation of the organic synthesis described above is shown in FIG. 1. The labeled fatty acids were formulated in 10% ethanol in saline for rat studies and 4% BSA in saline for monkey studies (sterile filtered through a 0.22 μm Millipore filter).

Example 2

Biodistribution of $^{18}$F-labeled 3,4-cyclopropyl-heptadecanoic acid([$^{18}$F]-FCPHA)

The initial myocardial behavior of [$^{18}$F]-FCPHA was essentially similar to that of normal FAs, as evidenced that this analog concentrates in the same metabolic pools and has the same subcellular distribution in the rat heart, where it is found in the mitochondria. Male Sprague-Dawley rats weighing approximately 300-350 grams, were injected without anesthesia with 40 μCi of [$^{18}$F]-FCPHA in a total volume of 200 μl. The radiolabeled FA was injected into the tail vein and the rats subsequently sacrificed at 5 minutes and 60 minutes post-injection. The organs were excised and counted in a gamma counter. Accumulation of the FA in various organs in % DPG (dose per gram) is detailed in Table 1.

TABLE 1

Accumulation of $^{18}$F-FCPHA in Rat Tissue

| Tissue | % DPG (5 min) | % DPG (60 min) |
|---|---|---|
| Heart | 1.55 ± 0.66 | 1.43 ± 0.14 |
| Lung | 0.47 ± 0.12 | 0.33 ± 0.16 |
| Liver | 1.34 ± 0.26 | 0.87 ± 0.15 |
| Bone | 0.16 ± 0.03 | 0.70 ± 0.39 |
| Blood | 0.064 ± 0.008 | 0.080 ± 0.019 |
| Spleen | 0.55 ± 0.30 | 0.34 ± 0.085 |
| Kidney | 0.41 ± 0.097 | 0.34 ± 0.08 |
| Adrenal | 0.22 ± 0.061 | 0.30 ± 0.16 |
| Stomach | 0.12 ± 0.067 | 0.15 ± 0.038 |
| Gastrointestinal Tract | 0.19 ± 0.040 | 0.24 ± 0.039 |
| Testes | 0.020 ± 0.003 | 0.011 ± 0.004 |
| Brain | 0.06 ± 0.01 | 0.05 ± 0.02 |
| Muscle | 0.25 ± 0.009 | 0.097 ± 0.075 |

Bone accumulation of the fluorinated FA measured de-fluorination of the compound and its subsequent accumulation. To confirm imaging resolution, the following ratios were determined at 5 and 60 minutes post-injection (Table 2).

TABLE 2

Imaging Resolution of $^{18}$F-FCPHA

| Tissue Ratio | Ratio at 5 minutes | Ratio at 60 minutes |
|---|---|---|
| Heart-to-blood | 25.8 | 20.4 |
| Heart-to-lung | 3.3 | 4.6 |

Table 3 shows the biodistribution of the β-methyl analog, [$^{18}$F]FBMHA, at 5 and 60 minutes after intravenous administration in rats (5 per time point). At 5 minutes after injection, accumulation of radioactivity in the heart was 2.56% dose per gram, with nearly an equal amount of radioactivity in the kidneys. Tracer activity in the blood at 5 minutes was 1.02% DPG, and remained relatively high (0.58% DPG) after 60 minutes. Most of the radioactivity accumulated in the liver. The heart-to-blood ratio of 2.6 at 5 minutes did not significantly change after 60' minutes. There was bone accumulation of 0.52% DPG at 5 minutes, which increased to 2.36% DPG at 60 minutes, indicating extensive defluorination. Biodistribution of [$^{18}$F]FBMHA in rats was repeated using a 4% Tween-80/saline formulation and similar results were obtained.

TABLE 3

Tissue distribution of [$^{18}$F]FBMHA in Sprague-Dawley rats

| Organ | 5 minutes | 60 minutes |
|---|---|---|
| Blood | 1.02 ± 0.22 | 0.58 ± 0.27 |
| Heart | 2.56 ± 0.76 | 1.69 ± 0.13 |
| Lung | 1.25 ± 0.18 | 0.58 ± 0.17 |
| Liver | 8.88 ± 2.97 | 4.17 ± 1.49 |
| Kidney | 2.62 ± 0.86 | 1.66 ± 0.61 |
| Muscle | 0.66 ± 0.22 | 0.41 ± 0.10 |
| Bone | 0.52 ± 0.16 | 2.36 ± 0.78 |
| Brain | 0.25 ± 0.07 | 0.27 ± 0.03 |

Table 4 represents heart-to-blood ratios in rats 60 minutes after administration of labeled [$^{18}$F]FCPHA compared to other β-methyl analogs [$^{18}$F]FBMHA, [$^{11}$C]BMHA and [$^{125}$I]BMIPP.

TABLE 4

Heart to blood ratios of various β-methyl analogs

| | [$^{18}$F]FCPHA | [$^{18}$F]FBMHA | [$^{11}$C]BMHA | [$^{125}$I]BMIPP |
|---|---|---|---|---|
| Ratio | 20:1 | 3:1 | 10:1 | 3:1 |

Example 3

Comparison of the biodistribution of R,R and S,S diastereomers with racemic mixtures of $^{11}$C or $^{14}$C-labeled 3-methyl-heptadecanoic acid The following data compare the biodistribution of 1-[$^{11}$C]-3(S)-methylheptadecanoic acid (the 'S' isomer) and 1-[$^{11}$C]-3(R)-methylheptadecanoic acid (the 'R' isomer). Also compared is the racemic mixture, 1-[$^{14}$C]-3(R,S)-methylheptadecanoic acid, labeled with [14]C. Measurement of the % DPE (dose per gram) at 5 minutes and 30 minutes revealed that the 'S' isomer has higher heart uptake and higher heart-to-blood ratios, indicating that the 'S' isomer is preferable than the 'R' isomer or the racemic mixture as a potential heart imaging agent. Biodistribution was performed in six rats for each compound and time point. The 5-minute distribution data are contained in Table 5, while the 30-minute data are contained in Table 6. These unexpected results imply that during β-oxidation, enoyl-CoA hydratase is stereo-specific and only recognizes the 'S' isomer. Further, stereoisomeric purity is important for targeting the MFA to heart tissue.

TABLE 5

Biodistribution of isomers and racemic mixture of 3-methylheptadecanoic acid and at 5 minutes post-injection

| Organ | S-isomer | R-isomer | R,S racemic mixture |
|---|---|---|---|
| Blood | 0.18 ± 0.01 | 0.30 ± 0.04 | 0.23 ± 0.02 |
| Heart | 3.44 ± 0.54 | 1.40 ± 0.23 | 2.20 ± 0.95 |
| Left Ventricle | 4.05 ± 0.77 | 1.50 ± 0.50 | 2.87 ± 1.01 |
| Right Ventricle | 3.40 ± 0.82 | 0.94 ± 0.46 | 2.05 ± 0.54 |
| Heart-to-blood | 19.00 | 4.66 | 9.56 |
| Left ventricle-to-blood | 22.00 | 5.00 | 12.48 |
| Right ventricle-to-blood | 18.88 | 3.13 | 8.90 |

TABLE 6

Biodistribution of isomers and racemic mixture of 3-methylheptadecanoic acid and at 30 minutes post-injection

| Organ | S-isomer | R-isomer | R,S racemic mixture |
|---|---|---|---|
| Blood | 0.21 ± 0.04 | 0.23 ± 0.03 | 0.20 ± 0.02 |
| Heart | 3.08 ± 0.30 | 1.07 ± 0.16 | 2.10 ± 0.41 |
| Left Ventricle | 3.81 ± 0.37 | 1.33 ± 0.25 | 2.81 ± 0.35 |
| Right Ventricle | 2.82 ± 0.46 | 0.93 ± 0.35 | 2.10 ± 0.41 |
| Heart-to-blood | 14.66 | 5.95 | 10.10 |
| Left ventricle-to-blood | 18.14 | 5.78 | 12.48 |
| Right ventricle-to-blood | 18.88 | 4.00 | 10.05 |

Example 4

Figure 3:
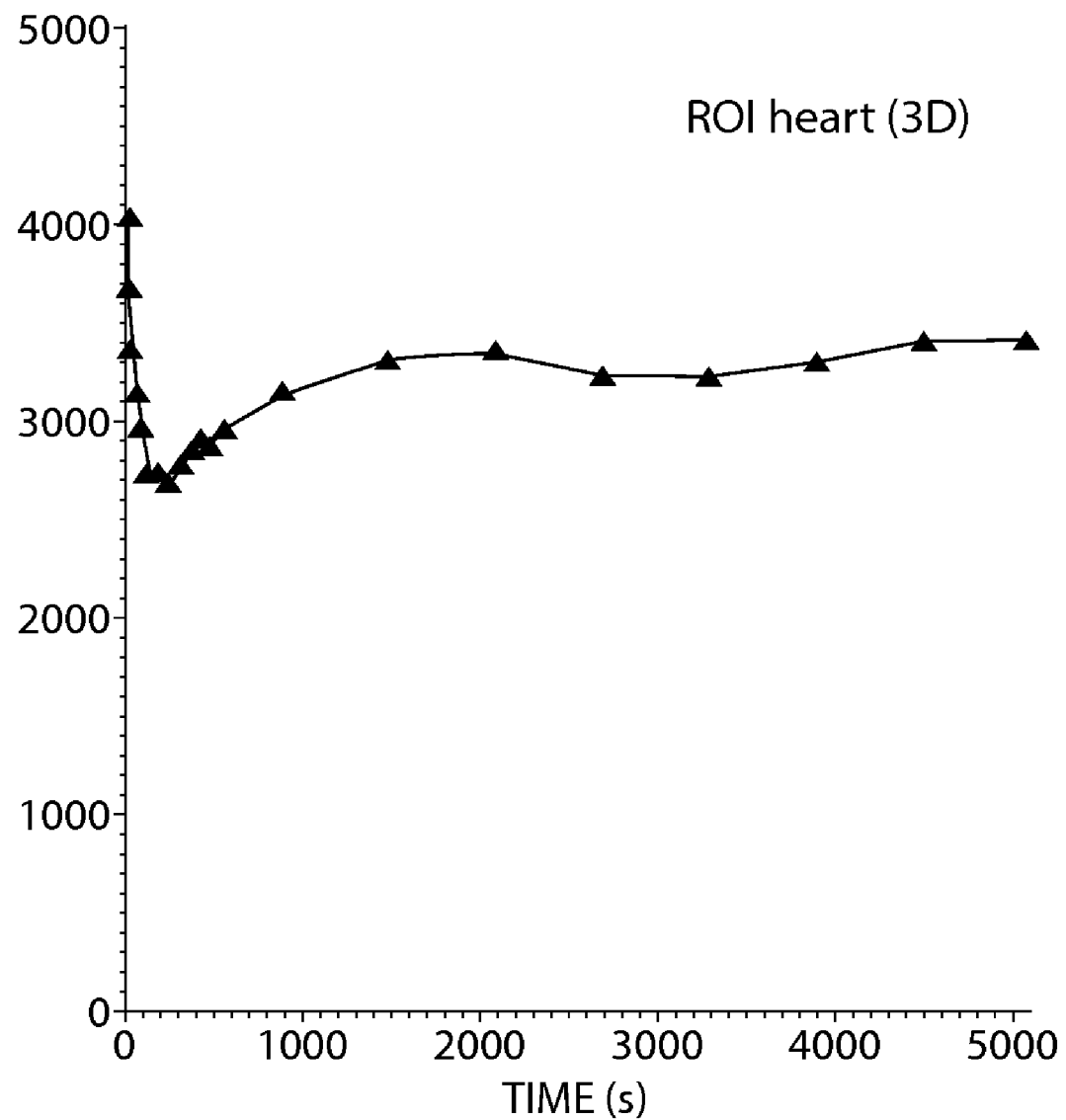
FIG. 3 depicts [$^{18}F$]-FCPHA activity in the heart of a monkey as a function of time.
Figure 4:
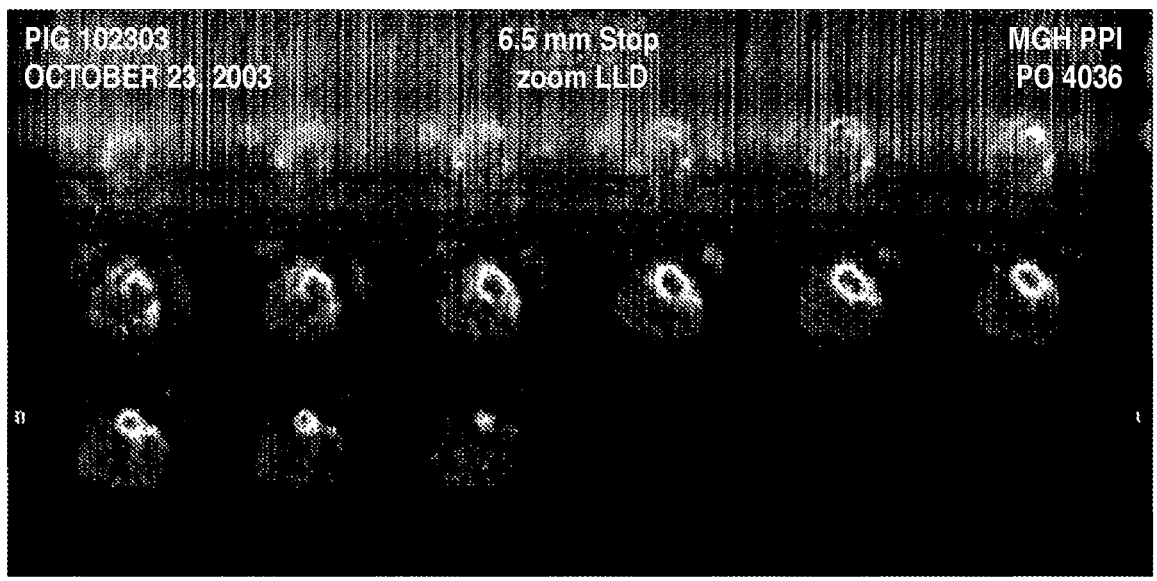
FIG. 4 shows heart images of a pig at 2-8 minutes after intravenous injection of 18 mCi of [$^{13}N$]-ammonia.
Figure 5:
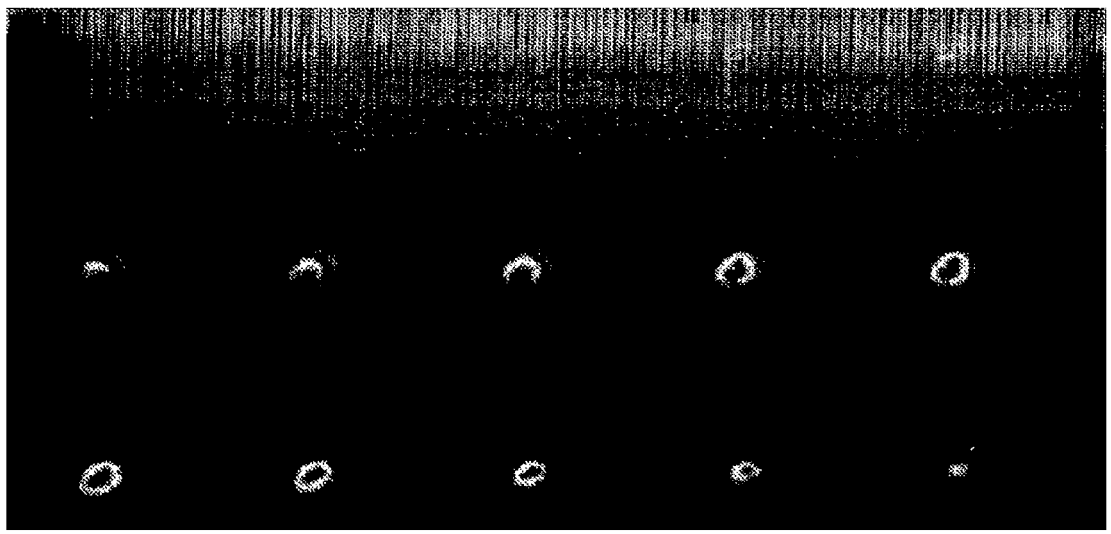
FIG. 5 shows heart images of the same pig in FIG. 5, at 2-8 minutes after intravenous injection of 19 mCi [$^{18}F$]-FCPHA.
Figure 6:
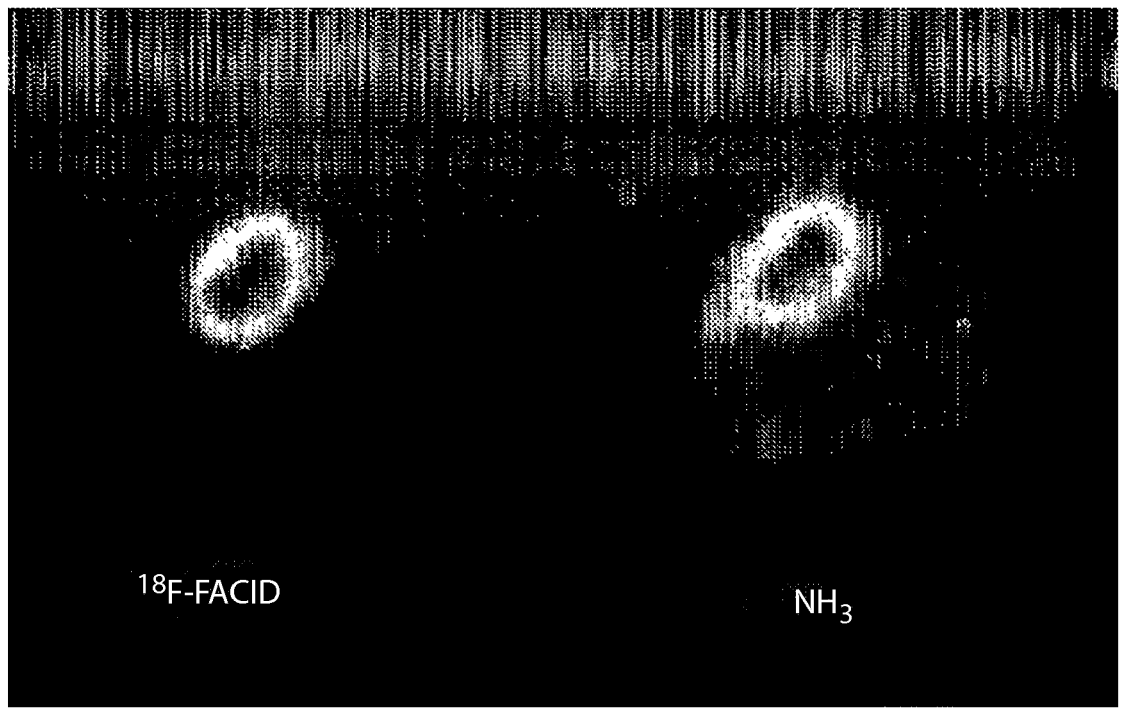
FIG. 6 is a comparison of [$^{13}N$]-ammonia (right) and [$^{18}F$] FCPHA (left) images obtained from a pig at 2-8 minutes after tracer injection.

Imaging Studies in Monkeys with [$^{18}$F]-labeled 3,4-cyclopropyl-heptadecanoic acid [$^{18}$F]-FCPHA Imaging of pig and monkey hearts after injection of [$^{18}$F] FCPHA showed an initial spike of activity corresponding to blood flow followed by a plateau after 10 minutes (FIG. 3). FIG. 4 represents heart images of a pig at 2-8 minutes post-injection of [$^{13}$N]ammonia (18 mCi), and FIG. 5 displays heart images of the same pig at 2-8 minutes after intravenous administration of [$^{18}$F]FCPHA (19 mCi). In FIG. 6, the images are a comparison of [$^{13}$N]ammonia (right) and [$^{18}$F] FCPHA (left) at 2-8 minutes in a pig. Pig images had a clearer delineation of the heart muscle with [$^{18}$F]FCPHA compared with that from [$^{13}$N]ammonia. The [$^{18}$F]FCPHA late images at 60 minutes exhibited high myocardial activity retention.

Figure 7:
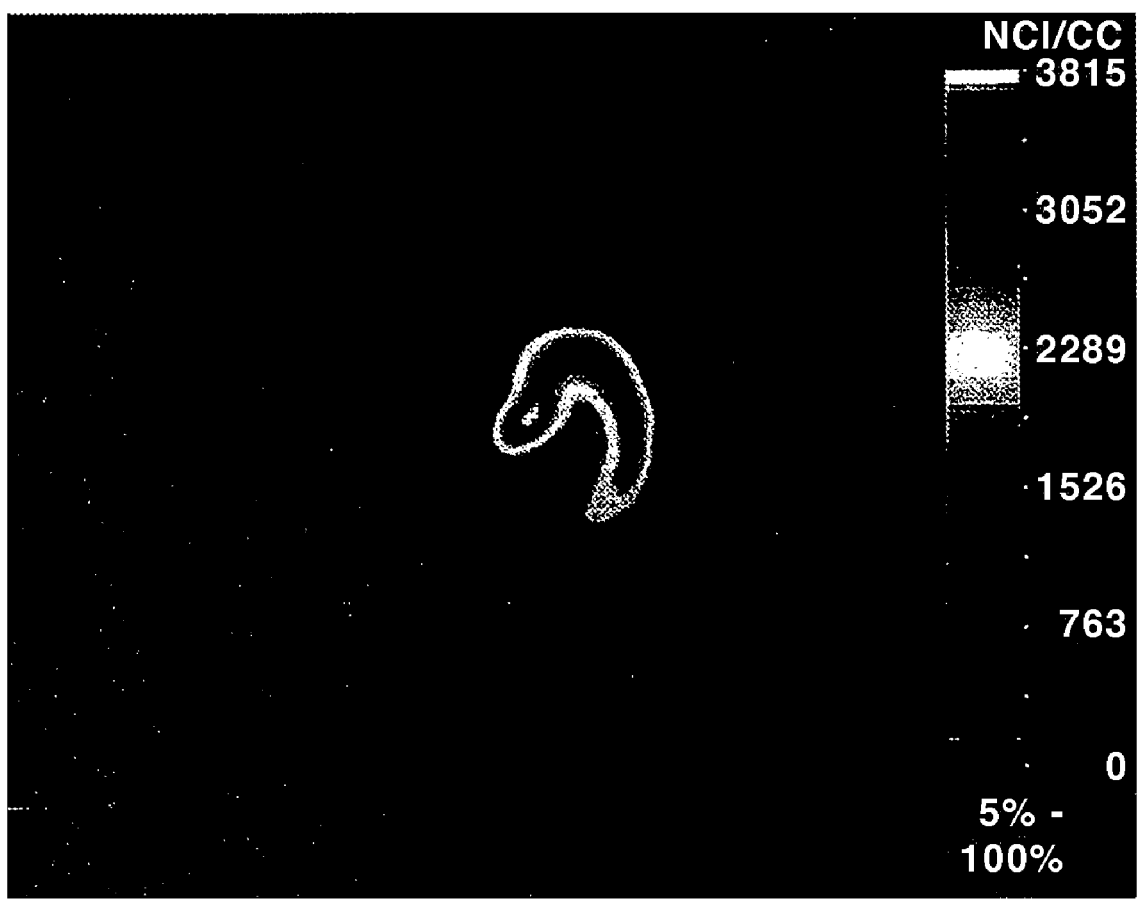
FIG. 7 is an image collected by positron emission tomography of the biodistribution of [$^{18}F$]-FCPHA in the left and right ventricles of a monkey heart.
Figure 8:
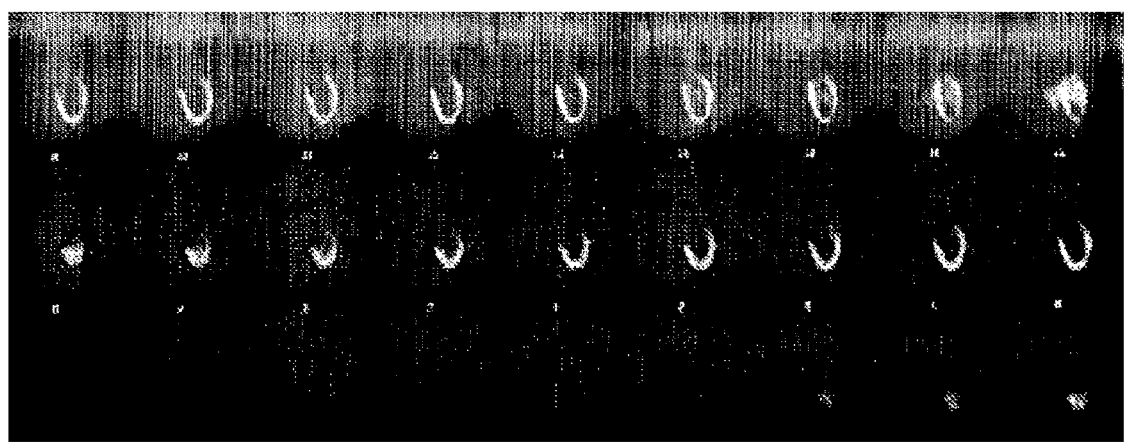
FIG. 8 shows transverse heart level slices of a monkey 60 minutes after administration of [$^{18}F$]-FCPHA.

The biodistribution of [$^{18}$F]-FCPHA was also studied in monkeys. Sixty minutes after intravenous injection of 5 mCi of [$^{18}$F]-FCPHA, the radiolabeled FA analog was visualized by positron emission tomography (PET) and clearly demonstrates myocardial trapping in both left and right ventricles (FIG. 7). FIG. 8 shows transverse heart level slices of a monkey 60 minutes after administration of [$^{18}$F]FCPHA. Blood activity showed fast clearance in both pig and monkey.

Example 5

Synthesis of terminally-labeled [$^{18}$F]-fluorophenyl-3,4-cyclopropyl-heptadecanoic acid Based on the aforementioned protocol described in Example 1, synthesis of this molecule can be achieved by using a different starting material (such as 10-phenyl-1-decanol). This starting material, 10-phenyl-1-decanol, was reacted with triphenylphosphine and dissolved in benzene. A solution of carbon tetrabromide in benzene was added slowly and the mixture was refluxed for 90 minutes. The reaction mixture was then cooled and filtered, and the residue washed three times with portions of petroleum ether. The residue was evaporated to dryness and then stirred with petroleum ether and left overnight in a freezer. The solution was then filtered, the resultant residue washed twice with petroleum ether, and the combined solution evaporated to dryness. This is predicted to yield an alkyl bromide variant of the starting product, wherein the bromine atom is substituted for the primary alcohol moiety.

Figure 9:
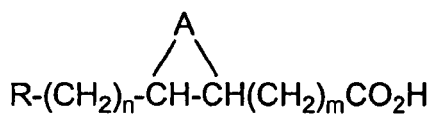
FIG. 9 depicts the general formula of a terminally labeled straight chain fatty acid comprising a substituent designated by 'A' and a phenyl moiety comprising a substituted radiolabel.
Figure 9:
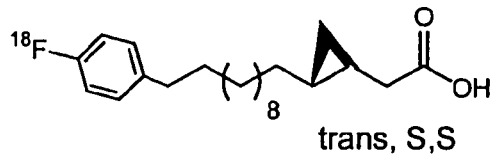
Figure 9:
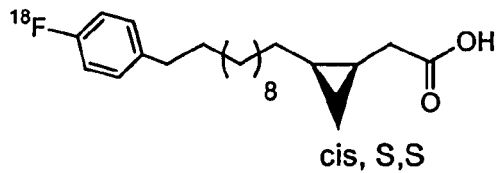
Figure 9:
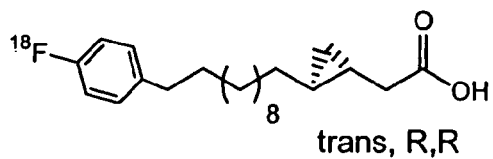
Figure 9:
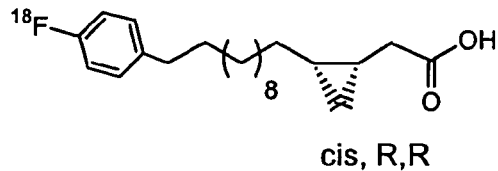

The brominated compound was subjected to Grignard synthesis as follows. The brominated compound in ether was injected into refluxed ether containing magnesium. Reflux continued for 90 minutes under an argon or nitrogen atmosphere. The reaction mixture was then cooled to room temperature, then subsequently injected into a $^7CO_2$ trap and the solution shaken for 5 minutes. The solution was transferred to a separatory funnel, washed twice with ether, and combined with 1N HCl. The solution was washed twice with water, dried using $Na_2SO_4$ and evaporated. The resulting compound was predicted to be 17-phenyl-1-heptadecanol. The following steps after the second PCC oxidation will continue as described in Example 1. This synthesis yields an analog that contains a terminal phenyl group and a cyclopropyl moiety at the 3,4-carbon position (see FIG. 9).

The $^{18}$F or $^{123}$I radiolabel can be added to the terminal phenyl moiety by other methods, such as the Schiemann reaction. For $^{18}$F labeling the benzene moiety can undergo nitration in nitric acid ($HNO_3$) and sulfric acid ($H_2SO_4$), followed by reduction with Sn and HCl. This yields a phenyl moiety labeled with an amino group (aniline). Incubation with $NaNO_2$ and HCl will convert the amino group to the diazonium ion. The diazonium salt is then subjected to fluorination with [$^{18}$F]-HBF$_4$. This yields a phenyl group mono-substituted with fluorine. For $^{123}$I labeling, the benzene substituent will undergo nitration in $HNO_3$ and $H_2SO_4$, yielding an aniline group. $NaNO_2$ and HCl, followed by iodination with potassium iodide (KI). The iodinated aryl derivative is radiolabeled by an exchange reaction with radioiodide in an acid media at high temperatures. Other methods include preparation of a corresponding tributyl-tin derivative, followed by electrophilic aromatic radioiodination.

Example 6

Synthesis of endo-[$^{18}$F]Fluoro- and [$^{123}$I]Iodo-3,4-cyclopropylheptadecanoic acid variants Syntheses of endo-vinylic radiolabeled variants of FCPHA were carried out essentially as described in Example 1, but with modifications. A solution of 6-benzyloxy-1-hexanol was treated with PCC in methylene chloride at 25° C. The black mixture was stirred for 2 h and filtered through silica gel. The solvent was removed and the crude oil was separated on silica gel using hexane/ethyl acetate (90:10).

The resulting aldehyde, 6-benzyloxy-1-hexanal, was mixed with (carbethoxymethylene) triphenylphosphorane in methylene chloride at 25° C. The mixture was stirred overnight, after which the solvent was removed and replaced with hexane. Solid matter was removed by filtration. Chromatography on silica gel, hexane/ethyl acetate (90:10) yielded the corresponding ethyl ester.

Diisobutylaluminum hydride in hexane was added dropwise to the ethyl ester in methylene chloride at −78° C. The mixture was allowed to slowly warm to 0° C. and ethyl acetate was added dropwise, followed by ice. The resultant slurry was acidified with 10% HCl and extracted with ether. The combined ether extracts were washed with brine, dried, and solvent was removed. Chromatography of the crude oil using hexane/ethyl acetate (80:20) yielded the unsaturated primary alcohol.

The unsaturated primary alcohol was subjected to cyclopropanation essentially as described in Charette and coworkers, as well as Example 1. Dry methylene chloride was cooled to −25° C. and placed under a nitrogen atmosphere. Diethyl zinc, followed by 1,2-dimethoxyethane (DME), was added. Diiodomethane was added dropwise to the solution, while maintaining the reaction temperature between −25° C. and −10° C. This solution was then added by double-ended needle, to a solution containing the unsaturated primary alcohol, dioxaborolane (made from (+)N,N,N',N'-tetramethyl-L-tartaramide and butylboronic acid), and 4 Å molecular sieves in methylene chloride under nitrogen at −40° C. and −30° C. The reaction mixture was stirred for 2 hours at −25° C., then allowed to warm to 0° C. Saturated ammonium chloride was added to the mixture, then stirred at RT for 16 hours. Solid matter was removed by filtration and the layers were separated. The aqueous layer was extracted with methylene chloride, while organic layers were pooled, washed with water, and dried. The crude oil was separated by silica gel chromatography in hexane:ethyl acetate (90:10), yielding the cyclopropyl alcohol. This reaction was repeated twice.

Iodine was added in portions to a solution containing the cyclopropyl alcohol and triphenylphosphine in dimethylformamide. The dark red mixture was combined with 10% sodium thiosulfate and extracted with ether. The combined extract was washed with water, brine, and the solvent was subsequently removed. Silica gel chromatography in hexane:ethyl:acetate (95:5) yielded the alkyl iodide. This alkyl iodide, was combined with sodium cyanide in dimethyl sulfoxide (DMSO), was heated to 80° C. for 2 hours. The mixture was poured into water, and was then followed by ether extraction. The combined extract was washed with water, dried, and solvent removed. The crude oil was separated by silica gel chromatography in hexane:ethyl acetate (80:20) and yielded the corresponding nitrile compound.

The corresponding nitrile compound was mixed with KOH and water in ethylene glycol, then heated for 6 h at 170° C. Once cooled, the mixture was diluted with 10% HCl and extracted with ether. The combined extract was dried and the solvent removed. The crude carboxylic acid was treated with diazomethane (made from N-methyl-N'-nitro-N-nitrosoguanidine and 40% KOH in ether). The reaction mixture was stirred for 1 h before solvent removal. Chromatography of the crude oil on silica gel and hexane/ethyl acetate (80:20) yielded the corresponding methyl ester.

The methyl ester was hydrogenated using lithium aluminum hydride, once again yielding a primary alcohol. The primary alcohol was substituted by addition of an alcohol-protecting group, tetrahydropyran (THP). Subsequent hydrogenation of the primary alcohol with 10% palladium on charcoal (Degussa) in methanol, followed by treatment with N-bromosuccinimide, yielded an alkyl bromide variant, wherein the bromine group was appended on the opposite end from the THP protecting group. The alkyl bromide variant was then subjected to treatment with n-butyllithium in hexane, in the presence of an alkyne, which appended the alkyne group opposite from the THP moiety. The corresponding cyclopropyl alkyne was hydrogenated with tributyl-tin hydride and iodinated with $I_2$ to yield an endo-vinyl variant.

The endo-vinyl variant molecule was treated with TosH and $CrO_3$ under acidic conditions to facilitate removal of the THP protecting group and subsequent oxidation to the carboxylic acid. The corresponding carboxylic acid was then subjected to substitution of the iodide with tributyl-tin hydride. Radiolabeled sodium iodide (Na $^{123}$I) afforded substitution of the tributyl-tin moiety with $^{123}$I, resulting in endo-[$^{123}$I]-iodo-3,4-cyclopropylheptadecanoic acid. Alternatively, the tributyl-tin substituted carboxylic acid was treated with $^{18}F_2$ to yield endo-[$^{18}$F]-fluoro-3,4-cyclopropylheptadecanoic acid. A schematic overview of the synthesis described above is provided in FIG. 10.

Example 7

Figure 12:
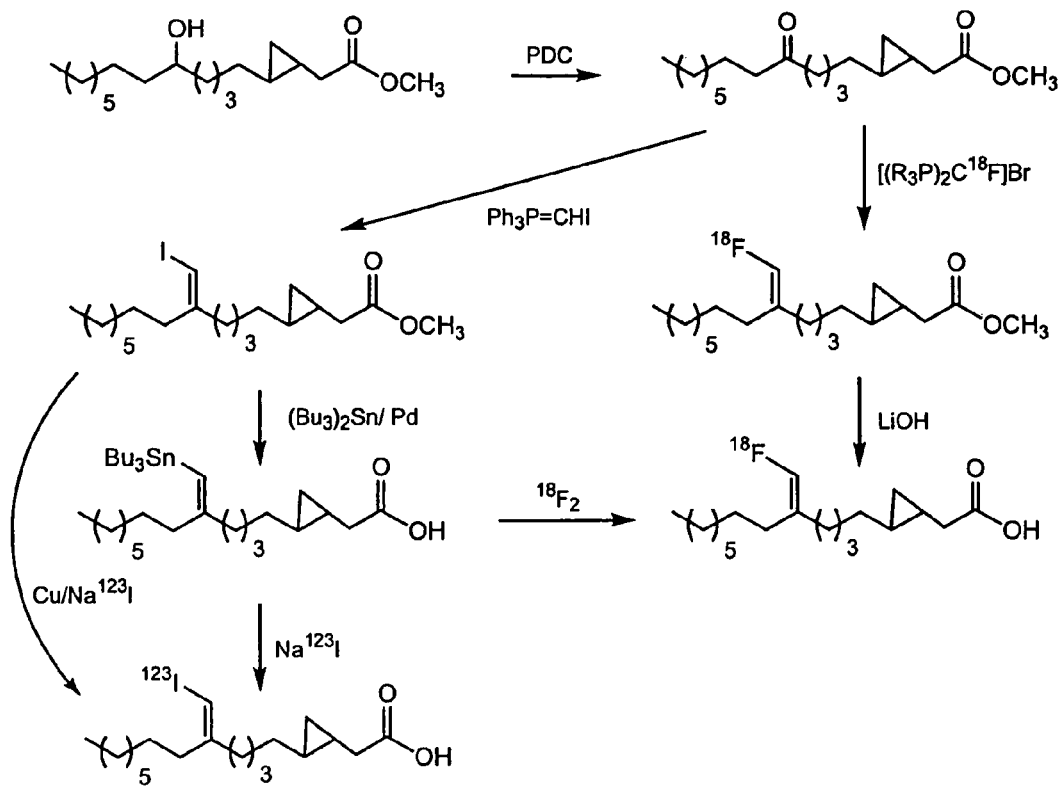
FIG. 12 is a schematic overview of the synthesis of exo-[$^{18}F$] fluoro- or [$^{123}I$]iodo-3,4-cyclopropylheptadecanoic acid.
Figure 13:
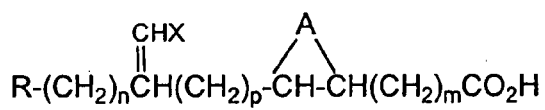
FIG. 13 depicts the general formula of a fatty acid comprising an exo-vinyl group. This exo-vinyl group can comprise a substituted radiolabel at substituents 'X' or 'Y'.

Synthesis of exo-[$^{18}$F]fluoro- and [$^{123}$I]iodo-3,4-cyclopropylheptadecanoic acid variants An overview of the partial synthesis of the exo-vinyl compounds of 3,4-cyclopropyl-heptadecanoic acid is shown in FIG. 12. Synthesis of radiolabeled exo-vinyl variants of 3,4-cyclopropyl-heptadecanoic acid was achieved essentially as described in Example 1, up until formation of 9-hydroxy-3,4-cyclopropylheptadecanoate methyl ester. This methyl ester was oxidized to its corresponding ketone with pyridinium dichromate (PDC) in methylene chloride at 25° C. The corresponding ketone can then be subjected to two different routes, depending on the radiolabeled halogen used.

Vinylic Iodination: Scheme 1

The following syntheses are based on the Horner-Witting reaction, with modifications described in Stork and Zhao, 1989. *Tetrahedron Lett.* 30: 2173-2174; and McCarthy et al. 1991. *J. Am. Chem. Soc.* 113: 7439-7440 (see also FIG. 12). Pre-formed iodomethyl-triphenylphosphonium iodide, consisting of triphenylphosphine and the iodinated ylide, was added slowly to a 1 M solution of sodium hexamethyldisilazane in tetrahydrofuran (THF). After stirring for one minute, the solution was cooled to −60° C. and hexamethylphosphorictriamide (HPMA) was added, followed by cooling to −78° C. The ketone compound described above was added, removed from the cold bath, and stirred for 30 minutes. Hexane was added to the mixture, followed by column chromatography and NMR analysis. This afforded substitution of the carbonyl group with the iodinated vinyl group. Subsequent treatment with tributyl-tin hydride and palladium on carbon yielded substitution of the vinylic iodine with tributyl-tin and conversion of the primary ester group to carboxylic acid. Treatment with radioiodinated sodium iodide (Na$^{123}$I) resulted in exo-[$^{123}$I]-iodo-3,4-cyclopropylheptadecanoic acid.

Vinylic Iodination: Scheme 2

Likewise, the addition of the radiolabeled iodine can be directly achieved, thereby eliminating the intervening vinylic tributyl-tin precursor molecule (FIG. 12). After substitution of the carbonyl group with the iodinated vinyl group, the molecule can then be reacted with copper and Na $^{123}$I directly, resulting in exo-[$^{123}$I]-iodo-3,4-cyclopropyl-heptadecanoic acid.

Vinylic Fluorination: Scheme 1

The vinylic tributyl-tin fatty acid derivative described in Scheme 1 of vinylic iodination can also be used to directly fluorinate the modified fatty acid by substitution of $^{18}F_2$ at the vinylic tributyl-tin moiety (FIG. 12). This yields exo-[$^{18}$F] fluoro-3,4-cyclopropyl-heptadecanoic acid.

Vinylic Fluorination: Scheme 2

An alternate synthesis of the vinylic fluorinated variant of 3,4-cyclopropyl-heptadecanoic acid can be achieved from the ketone compound described above (FIG. 12). A modified version of the mechanism is from Burton and Greenlimb 1975. *J. Org. Chem.* 40: 2796-2801; and in Schlosser and Zimmermann 1969. Synthesis 1: 75-76. Fluoromethyltriphenylphosphonium iodide was synthesized in a round-bottomed flask fitted with a water-cooled reflux condenser. The flask was charged. With triphenylphosphine and fluoroiodomethane in dry benzene. The resulting solution was refluxed for 64 hr with moderate stirring. Upon completion of the reaction, the white insoluble phosphonium salt was collected on a glass funnel, washed with hot benzene, and dried in a vacuum dessicator for 12 hr.

A separate flask was equipped with a constant-pressure addition funnel fitted with a nitrogen inlet, and a water-cooled reflux condenser topped with a T joint leading to a mineral oil bubbler. The apparatus was flushed with nitrogen, flame-dried and allowed to cool to room temperature while de-aeration with nitrogen was continued. The flask was charged with fluoromethyltriphenylphosphonium iodide, dry THF, and toluene. The nitrogen atmosphere was maintained throughout the system. The slurry of phosphonium salt and solvent was moderately stirred while cooled in a dry ice-isopropanol slush bath. During the cooling process, the addition funnel was charged with n-butyllithium in hexane. Any appreciable amount of hydrolysis of the organolithium reagent was avoided by a constant sweep of nitrogen over the addition funnel when the stopper was removed and by transferring the base via pipette under a dry nitrogen atmosphere. The base was added dropwise over a 23-minute period. After addition, the reaction mixture was stirred for 25 minutes at −78° C. At the end of the 25-minute period, the reaction mixture was withdrawn under a nitrogen atmosphere and added to ethylene bromide with the evolution of heat. The reaction was allowed to progress for another 25 minutes at −78° C.

The corresponding ketone obtained from PDC oxidation of the methyl ester 9-hydroxy-3,4-cyclopropylheptadecanoate was then added. The reaction between the ylide and the ketone proceeded for 2 h at −78° C., then allowed to warm to room temperature, where it was incubated for an additional 1.5 h. The reaction mixture was then cooled on ice. Potassium tert-butoxide was added and the mixture was stirred for 2 h at 0° C. The reaction mixture was centrifuged and decanted, and the precipitate washed with small portions of THF. The decantates were combined and washed with saturated aqueous sodium chloride until the aqueous layer was of neutral pH. The solvent was removed, the dried and filtered organic material was flash-distilled at reduced pressure, and then subjected to chromatography and NMR analysis. Base hydrolysis of the $^{18}$F-substituted ester resulted in conversion to the corresponding carboxylic acid. This yielded exo-[$^{18}$F]-fluoro-3,4-cyclopropylheptadecanoic acid.

Example 8

Synthesis of 4 or 5-membered ring substituent variations of heptadecanoic acid

Variations on heptadecanoic acid have also been synthesized, wherein the cyclopropyl substituent is replaced instead with cyclobutyl or cyclopentyl moieties. Synthesis of these compounds containing variations of the modified fatty acids described in Examples 1, 4, 5, and 6 are provided below.

Figure 14:
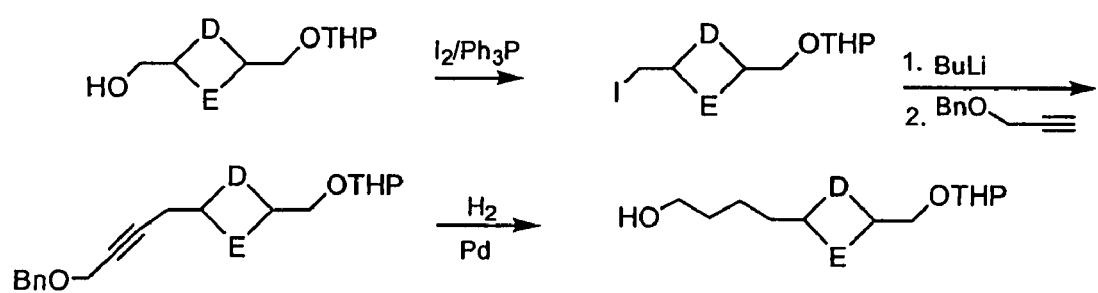
FIG. 14 shows the partial synthesis of a portion of a modified fatty acid comprising a substituent that can be a four- to five-membered ring structure.
Figure 15:
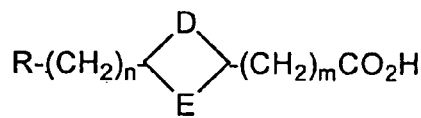
FIG. 15 shows the general formula of a modified fatty acid comprising a substituent that can be a four- to five-membered ring structure. This fatty acid variant can comprise a combination of features described in FIGS. 2, 4, 11, and 13.

Synthesis of MFAs with the cyclopropyl moiety was described in prior examples. However, instead of 6-benzyloxy-1-hexanol, which was used as starting material for many of the aforementioned MFAs, cyclic primary alcohols (cyclobutanol or cyclopentanol) can be substituted with a protective group like THP (tetrahydropyran). The mono-protected cyclic alcohol is then subjected to triphenylphosphine in the presence of $I_2$, which resulted in an alkyl iodide variant, protected at the other end by THP. Addition of a benzyloxy-alkyne of varying chain length was achieved by addition of n-butyllithium. Hydrogenation in 10% palladium on carbon resulted in a cyclobutyl or cyclopentyl-1-nonanol or heptanol, still protected at one end by THP. The chain length of the cyclic monoprotected primary alcohol depends on the length of the benzyloxy-alkyne used. These cyclic mono-protected alcohols were used in subsequent reactions, described below. FIG. 14 contains a diagram of the partial synthesis of these cyclic mono-protected alcohols.

[$^{18}$F]-9-fluoro-3,4-cyclobutyl- or [$^{18}$F]-9-fluoro-3,4-cyclopentyl-heptadecanoic acid The cyclic mono-protected nonanol was subjected to PCC oxidation, yielding the corresponding aldehyde. Under a nitrogen atmosphere, octyl bromide in dry ether was added to magnesium metal in ether at a rate as to maintain gentle reflux. After addition was complete, the reaction mixture was stirred for 1 h and the cyclic mono-protected nonanal in ether, was added dropwise to the reaction mixture at room temperature. The mixture was stirred for 4 h, then poured over ice water, acidified in 10% HCl, and extracted with ether. The combined extracts were washed wth brine, dried, and solvent removed. Chromatography on silica gel using hexane/ethyl acetate (80:20) yielded the cyclic mono-protected heptadecanol.

The cyclic mono-protected heptadecanol was then subjected to de-protection by treatment with TosH and $CrO_3$. This yielded the formation of the corresponding cyclic carboxylic acid. The cyclic carboxylic acid was combined with methane sulfonyl chloride and 4-dimethyl aminopyridine (DMAP) in methylene chloride/pyridine (90:10). The mixture was stirred for 2 h, then washed with 10% HCl until the aqueous layer was acidic and then washed with 10% $NaHCO_3$. The crude oil was chromatographed on silica gel in methylene chloride/methanol (95:5).

$^{18}$Fluorine in water was added to a vial containing Kryptofix-222 and $K_2CO_3$. Water was removed using a nitrogen stream at 115° C. followed by addition of acetonitrile. To this vial was the mesylated carboxylic acid in acetonitrile. The reaction was heated at 120° C. for 10 minutes, which gave the cyclobutyl or cyclopentyl variant of heptadecanoic acid [$^{18}$F]-labeled at the 9-carbon position, followed by silica Sep-Pak purification in hexane/ethyl acetate (85:15).

Terminally-labeled [$^{18}$F]-fluorophenyl-3,4-cyclobutyl- or cyclopentyl-heptadecanoic acid Based on the aforementioned protocol described in Example 4, synthesis of this molecule can be achieved by using a different starting material (such as 10-phenyl-1-decanol). This starting material, 10-phenyl-1-decanol, was reacted with triphenylphosphine and dissolved in benzene. A solution of carbon tetrabromide in benzene was added slowly and the mixture was refluxed for 90 minutes. The reaction mixture was then cooled and filtered, and the residue washed three times with portions of petroleum ether. The residue was evaporated to dryness and then stirred with petroleum ether and left overnight in a freezer. The solution was then filtered, the resultant residue washed twice with petroleum ether, and the combined solution evaporated to dryness. This is predicted to yield an alkyl bromide variant of the starting product, wherein the bromine atom is substituted for the primary alcohol moiety.

The brominated compound was subjected to Grignard synthesis as follows. The brominated compound in ether was injected into refluxed ether containing magnesium. Reflux continued for 90 minutes under an argon or nitrogen atmosphere. The reaction mixture was then cooled to room temperature, then subsequently injected into a trap containing a cyclobutyl- or cyclopentyl mono-protected 1-heptanol and the solution shaken for 5 minutes. The solution was transferred to a separatory funnel, washed twice with ether, and combined with 1N HCl. The solution was washed twice with water, dried using $Na_2SO_4$ and evaporated. The resulting heptadecanol compound was predicted to contain a terminal phenyl group at one end, with a cyclobutyl or cyclopentyl substituent followed by the THP protective group.

The cyclic mono-protected heptadecanol was then subjected to de-protection by treatment with TosH and $CrO_3$. This yielded the formation of the corresponding cyclic carboxylic acid. The cyclic carboxylic acid was combined with methane sulfonyl chloride and 4-dimethyl aminopyridine (DMAP) in methylene chloride/pyridine (90:10). The mixture was stirred for 2 h, then washed with 10% HCl until the aqueous layer was acidic and then washed with 10% $NaHCO_3$. The crude oil was chromatographed on silica gel in methylene chloride/methanol (95:5).

The $^{18}F$ or $^{123}I$ radiolabel can be added to the terminal phenyl moiety by other methods, such as the Schiemann reaction. For $^{18}F$ labeling the benzene moiety can undergo nitration in nitric acid ($HNO_3$) and sulfuric acid ($H_2SO_4$), followed by reduction with Sn and HCl. This yields a phenyl moiety labeled with an amino group (aniline). Incubation with $NaNO_2$ and HCl will convert the amino group to the diazonium ion. The diazonium salt is then subjected to fluorination with [$^{18}F$]-$HBF_4$. This yields a phenyl group mono-substituted with fluorine. For $^{123}I$ labeling, the benzene substituent will undergo nitration in $HNO_3$ and $H_2SO_4$, yielding an aniline group. $NaNO_2$ and HCl, followed by iodination with potassium iodide (KI). The iodinated aryl derivative is radiolabeled by an exchange reaction with radioiodide in an acid media at high temperatures. Other methods include preparation of a corresponding tributyl-tin derivative, followed by electrophilic aromatic radioiodination.

Synthesis of endo-vinylic variants of cyclobutyl or cyclopentyl-substituted heptadecanoic acid Cyclobutyl and cyclopentyl variants of the endo-vinylic modified fatty acids described in Example 5 are synthesized essentially as described, however the starting material, a cyclobutyl- or cyclopentyl THP mono-protected heptanol, was treated with N-bromosuccinimide. This yielded an alkyl bromide variant, wherein the bromine group was appended on the opposite end from the THP protecting group. The alkyl bromide variant was then subjected to treatment with n-butyllithium in hexane, in the presence of an alkyne, which appended the alkyne group opposite from the THP moiety. The corresponding cyclopropyl alkyne was hydrogenated with tributyl-tin hydride and iodinated with $I_2$ to yield an endo-vinyl variant.

The endo-vinyl variant molecule was treated with TosH and $CrO_3$ under acidic conditions to facilitate removal of the THP protecting group and subsequent oxidation to the carboxylic acid. The corresponding carboxylic acid was then subjected to substitution of the iodide with tributyl-tin hydride. Radiolabeled sodium iodide ($Na^{123}I$) afforded substitution of the tributyl-tin moiety with $^{123}I$, resulting in endo-[$^{123}I$]-iodo-3,4-cyclobutyl- or cyclopentyl-heptadecanoic acid. Alternatively, the tributyl-tin substituted carboxylic acid was treated with $^{18}F_2$ to yield endo-[$^{18}F$]-fluoro-3,4-cyclobutyl- or cyclopentyl-heptadecanoic acid.

Synthesis of exo-vinylic variants of cyclobutyl or cyclopentyl-substituted heptadecanoic acid The cyclic mono-protected nonanol was subjected to PCC oxidation, yielding the corresponding aldehyde. Under a nitrogen atmosphere, octyl bromide in dry ether was added to magnesium metal in ether at a rate as to maintain gentle reflux. After addition was complete, the reaction mixture was stirred for 1 h and the cyclic mono-protected nonanal in ether, was added dropwise to the reaction mixture at room temperature. The mixture was stirred for 4 h, then poured over ice water, acidified in 10% HCl, and extracted with ether. The combined extracts were washed wth brine, dried, and solvent removed. Chromatography on silica gel using hexane/ethyl acetate (80:20) yielded the cyclic mono-protected heptadecanol.

The cyclic mono-protected heptadecanol was then subjected to de-protection by treatment with TosH and $CrO_3$. This yielded the formation of the corresponding cyclic carboxylic acid. This cyclic carboxylic acid derivative was subjected to vinylic fluorination or iodination as described in Example 6 and modified from Burton and Greenlimb 1975 *J. Org. Chem.* 40: 2796-2801; and also from Schlösser and Zimmermann 1969 Synthesis 1: 75-76.

Although the foregoing invention has been described in some detail by way of illustration and example for purposes of clarity and understanding, it will be apparent to those skilled in the art that certain changes and modifications can be practiced. Therefore, the description and examples should not be construed as limiting the scope of the invention, which is delineated by the appended claims.

REFERENCES

Ambrose, K. R., Owen, B. A., Goodman, M. M., and Knapp, F. F. Jr.: "Evaluation of the metabolism in rat hearts of two new radioiodinated 3-methyl branched fatty acid myocardial imaging agents" 1987. *Eur. J. Nucl. Med.* 12: 486-491.

Bianco, J. A., Elmaleh, D. R., Leppo, J. A., King, M. A., Moring, A., Livni, E., Espinoza, E., Alpert, J. S., and Strauss, H. W. 1986. "Effect of glucose and insulin infusion on the myocardial extraction of a radioiodinated methyl-substituted fatty acid" *Eur. J. Nucl. Med.* 12: 120-4.

Burton, D. J., and Greenlimb, P. E.: "Fluoro Olefins. VII. Preparation of Terminal Vinyl Fluorides" 1975. *J. Org. Chem.* 40: 2796-2801.

Caldwell, J. H., Martin, G. V., Link, J. M., Krohn, K. A., and Bassingthwaighte, J. B.: "Iodophenylpentadecanoic acid-myocardial blood flow relationship during maximal exercise with coronary occlusion." 1990. *J. Nucl. Med.* 31: 99-105.

Charette, A. B., Prescott, S., and Brochu, C.: "Improved Procedure for the Synthesis of Enantiomerically Enriched Cyclopropylmethanol Derivatives" 1995. *J. Org. Chem.* 60: 1081-1083.

Chien, K. R., Han, A., White, J., and Kulkarni, P.: "In vivo esterification of a synthetic 125-I labeled fatty acid into cardiac glycerolipids" 1983. *Am. J. Physiol.* 245: H693-697.

Corbett, J. R. "Fatty Acids for Myocardial Imaging" 1999. *Semin. Nucl. Med.* 29(3): 237-258.

Elmaleh, D. R., Knapp, F. F. Jr, Yasuda, T., Coffey, J. L., Kopiwoda, S., Okada, R., and Strauss, H. W. 1981. "Myocardial imaging with 9-[Te-123m]telluraheptadecanoic acid" *J. Nucl. Med.* 22: 994-9.

Elmaleh, D. R., Livni, E., Levy, S., Varnum, D. A., Strauss, H. W., and Brownell, G. L.: "Comparison of 11C- and 14C-labeled fatty acids and their beta-methyl analogs" 1983. *Int. J. Nucl. Med. Biol.* 10: 181-7.

Elmaleh, D. R. Livni, E., Alpert, N. M., Strauss, H. W., Buxton, R., and Fischman, A. J.: "Myocardial extraction of 1-[11C] betamethylheptadecanoic acid" 1994. *J. Nucl. Med.* 35(3): 496-503

Evans, J. R., Gunton, R. W., Baker, R. G, et al: "Use of radioiodinated fatty acid for photoscans of the heart" 1965. *Circ. Res.* 16: 1-10.

Fox, K. A., Abendschein, D. R., Ambos, H. D., Sobel, B. E., and Bergmann, S. R.: "Efflux of metabolized and nonmetabolized fatty acid from canine myocardium. Implications for quantifying myocardial metabolism tomographically" (1975) *Circ. Res.* 57: 232-243.

Freundlieb, C., Hoeck, A., Vyska, K., Feinendegen, L. E., Machulla, H. J., and Stocklin, G.: "Myocardial imaging and metabolic studies with (17-123I) iodoheptadecanoic acid" 1980. *J. Nucl. Med.* 21: 1043-1050.

Goldstein, R. A., Klein, M. S., Welch, M. J., and Sobel, B. E.: "External assessment of myocardial metabolism with C-11 palmitate in vivo". 1980. *J. Nucl. Med.* 21: 342-348.

Goodman, M. M., Knapp, F. F., Elmaleh, D. P, and Strauss, H. W. 1984. "New myocardial imaging agents: synthesis of 15-(p-iodophenyl)-3-R,S-methylpentadecanic acid by the decomposition of piperidinyltriaine" *J. Org. Chem.* 49: 2322-5.

Grover-McKay, M., Schelbert, H. R., Schwaiger, M., Sochor, H., Guzy, P. M., Krivokapich, J., Child, J. S., and Phelps, M. E.: "Identification of impaired metabolic reserve by atrial pacing in patients with significant coronary artery stenosis" 1986. *Circulation* 74:281-292.

Hoffman, E. J., Phelps, M. E., Weiss, E. S., Welch, M. J., Coleman, R. E., Sobel, B. E., and Ter-Pogossian, M. M.: "Transaxial tomographic imaging of canine myocardium with 11C-palmitic acid". 1977. *J. Nucl. Med.* 18:57-61.

Hoffman, E. J., Huang, S. C., Phelps, M. E., and Kuhl, D. E. "Quantitation in positron emission computed tomography: 4. Effect of accidental coincidences" 1981. *J. Comput. Assist. Tomogr.* 5: 391-400.

Hoffman, E. J., Phelps, M. E. "Positron emission tomography: principles and quantitation". In: Phelps, M., Mazziotta, J., Schelbert, H., eds. *Positron emission tomography and autoradiography: principles and applications for the brain and heart*. New York: Raven Press; 1986: 237-286.

Jaffe, A. S., Biello, D. R., Sobel, B. E., and Geltman, E. M.: "Enhancement of metabolism of jeopardized myocardium by nifedipine". 1987. *Int. J. Cardiol.* 15:77-89.

Jaszczak, R. J. "SPECT: state-of-the-art scanners and reconstruction strategies". In: Diksic, M., Reba, R. C., eds. *Radiopharmaceuticals and brain pathology studied with PET and SPECT*. Boca Raton: CRC Press; 1991: 93-118.

Kairento, A. L., Livni, E., Harjula, A., Porkka, L., Lindroth, L., and Elmaleh, D. R.: "Comparative evaluation of [$^{123}$I] 14-p-iodophenyl-beta-methyltetradecanoic acid and thallium-201 in the detection of infarcted areas in the dog heart using SPECT" 1988. *Int. J. Rad Appl. Instrum. B.* 15(3): 333-8.

Kawamoto, M., Tamaki, N., Yonekura, Y., Magata, Y., Tadamura, E., Nohara, R., Matsumori, A., Sasayama, S., and Konishi, J.: "Significance of myocardial uptake of iodine 123-labeled beta-methyl iodophenyl pentadecanoic acid: comparison with kinetics of carbon 11-labeled palmitate in positron emission tomography" 1994. *J. Nucl. Cardiol.* 1(6): 522-8.

Klein, M. S., Goldstein, R. A., Welch, M. J., and Sobel, B. E.: "External assessment of myocardial metabolism with [1-11C] palmitate in rabbit hearts" 1979. *Am. J. Physiol.* 237: H51-H58.

Knabb, R. M., Bergmann, S. R., Fox, K. A., and Sobel, B. E.: "The temporal pattern of recovery of myocardial perfusion and metabolism delineated by positron emission tomography after coronary thrombolysis". 1987 *J. Nucl. Med.* 28:1563-1570.

Knapp, F. F Jr., Ambrose, K. R., Goodman, M. M.: "New radioiodinated methyl-branched fatty acids for cardiac imaging" 1986. *Eur. J. Nucl. Med.* 12: S39-S44.

Kobayashi, H., Kusakabe, K., Momose, M., Okawa, T., Inoue, S., Iguchi, N., and Hosoda, S.: "Evaluation of myocardial perfusion and fatty acid uptake using a single injection of iodine-123-BMIPP in patients with acute coronary syndromes" 1998. *J. Nucl. Med.* 39(7): 1117-22.

Links, J. M. "Physics and instrumentation of positron emission tomography". In: Frost, J. J., Wagner, H. N., eds. *Quantitative imaging: neuroreceptors, neurotransmitters, and enzymes*. New York: Raven Press; 1990: 37-50.

Livni, E., Elmaleh, D. R., Levy, S., Brownell, G. L., Strauss, H. W. 1982. "Beta-methyl [1-11C] heptadecanoic acid: a new myocardial metabolic tracer for positron emission tomography" *J. Nucl. Med.* 23:169-75.

Livni, E., Elmaleh, D. R., Barlai-Kovach, M. M., Goodman, M. M., Knapp, Ff. Jr, Strauss, H. W. 1985. "Radioiodinated beta-methyl phenyl fatty acids as potential tracers for myocardial imaging and metabolism" *Eur. Heart J.* 6 (Suppl B): 85-9.

Livni, E., Ito, S., Kassis, A. I., and Elmaleh, D. R. 1990. "(3H/14C) Beta-methylheptadecanoic acid subcellular distribution and lipid incorporation in mouse heart. *Lipids* 25:238-40.

Machulla, H. J, Stocklin, G., Kupfemagel, C., Freundlieb, C., Hock, A., Vyska, K., and Feinendegen, L. E.: "Comparative evaluation of fatty acids labeled with C-11, Cl-34m, Br-77, and I-123 for metabolic studies of the myocardium: concise communication" 1978. *J. Nucl. Med.* 19: 298-302.

Machulla, H. J, Marsmann, M., Dutschka, K: "Biochemical concept and synthesis of a radioiodinated phenyl fatty acid to in vivo metabolic studies of the myocardium" 1980. *Eur. J. Nucl Med.* 5: 171-173.

Marshall, R. C., Powers-Risius, P., Huesman, R. H., Reutter, B. W., Taylor, S. E., Maurer, H. E., Huesman, M. K., and Budinger, T. F.: "Estimating glucose metabolism using glucose analogs and two tracer kinetic models in isolated rabbit heart" 1998. *Am. J. Physiol.* 275: H668-H679.

McCarthy, J. R., Matthews, D. P., Stemerick, D. M., Huber, E. W., Bey, P., Lippert, B. J., Snyder, R. D., and Sunkara, P. S.: "Stereospecific Method to E and Z Terminal Fluoro Olefins and Its Application to the Synthesis of 2'-Deoxy-2'-fluoromethylene Nucleosides as Potential Inhibitors of Ribonucleoside Diphosphate Reductase" 1991. *J. Am. Chem. Soc.* 113: 7439-7440.

Miller, D. D., Gill, J. B., Livni, E., Elmaleh, D. R., Aretz, T., Boucher, C. A., and Strauss, H. W.: "Fatty Acid Analogue Accumulation: A Marker of Myocyte Viability in Ischemic-Reperfused Myocardium" 1988. *Circ. Res.* 63: 681-692.

Myars, D. W., Sobel, B. E., and Bergman, S. R.: "Substrate use in ischemic reperfused canine myocardium quantitative considerations". 1987 *Am. J. Physiol.* 253:107-114.

Phelps, M. E., Hoffman, E. J., Huang, S. C., Ter-Pogossian, M. M. "Effect of positron range on spatial resolution". 1975. *J. Nucl Med* 16: 649-652.

Poe, N. D, Robinson Jr., G. D., Graham, L. S., MacDonald, N. S.: "Experimental basis for myocardial imaging with 123-1-labeled hexadecanoic acid" 1976. *J. Nucl. Med.* 17: 1077-1082.

Poe, N. D., Robinson Jr., G. D., Zielenski, F. W., Cabeen Jr., W. R. Smith, J. W., and Gomes, A. S.: "Myocardial imaging with 123I-heptadecanoic acid" 1977. *Radiology* 124: 419-424.

Raichle, M. E., Welch, M. J., Grubb, R. L. Jr, Higgins, C. S., Ter-Pogossian, M. M., Larson, K. B.: "Measurement of regional substrate utilization rates by emission tomography" 1978. *Science* 199: 986-987.

Reske, S. N., Sauer, W., Machulla, H. J, Winkler, C.: "15-(p-(1-123)phenyl)) pentadecanoic acid as a tracer of lipid metabolism. Comparison with 1-C-14-palmitic acid in murine tissues" 1984. *J. Nucl. Med.* 25: 1335-1342.

Rosamond, T. L., Abendschein, D. R., Sobel, B. E., Bergmann, S. R., and Fox, K. A.: "Metabolic fate of radiolabeled palmitate in ischemic canine myocardium: implications for positron emission tomography". 1987. *J. Nucl. Med.* 28:1322-1329.

Schelbert, H. R., Henze, E., Keen, R., Schon, H. R., Hansen, H., Selin, C., Huang, S. C., Barrio, J. R., and Phelps, M. E.: "C-11 palmitate for the noninvasive evaluation of regional myocardial fatty acid metabolism with positron-computed tomography. IV. In vivo evaluation of acute demand-induced ischemia in dogs" 1983. *Am. Heart J.* 106: 736-50.

Schelbert. H. R., Henze, E., Sochor, H., Grossman, R. G., Huang, S. C., Barrio, J. R., Schwaiger, M., and Phelps, M. E.: "Effects of substrate availability on myocardial C-11 palmitate kinetics by PET in normal subjects and patients with ventricular dysfunction". 1986 *Am. Heart J.* 111: 1055-1064.

Schon, H. R., Schelbert, H. R., Robinson, G., Najafi, A., Huang, S. C., Hansen, H., Barrio. J., Kuhl, D. E., and Phelps, M. E.: "C-11 labeled palmitic acid for the noninvasive evaluation of regional myocardial fatty acid metabolism with positron computed tomography. I. Kinetics of C-11 palmitic acid in normal myocardium". 1982. *Am. Heart J.* 103:532-547.

Schon, H. R., Schelbert, H. R., Najafi, A., Hansen, H., Huang, H., Barrio, J., and Phelps, M. E.: "C-11 labeled palmitic acid for the noninvasive evaluation of regional myocardial fatty acid metabolism with positron computed tomography. II. Kinetics of C-11 palmitic acid in acutely ischemic myocardium". 1982. *Am. Heart J.* 103:548-561.

Schelbert, H. R., Henze, E., Schon, H. R., Keen, R., Hansen, H., Selin, C., Huang, S. C., Barrio, J. R., and Phelps, M. E.: "C-11 palmitate for the noninvasive evaluation of regional myocardial fatty acid metabolism with positron computed tomography. III. In vivo demonstration of the effects of the substrate availability on myocardial metabolism". 1983. *Am. Heart J.* 105:492-504.

Schelbert, H. R., Henze, E., Keen, R., Schon, H. R., Hansen, H., Selin, C., Huang, S. C., Barrio, J. R., Phelps, M. E.: "C-11 palmitate for the noninvasive evaluation of regional myocardial fatty acid metabolism with positron-computed tomography. IV. In vivo evaluation of acute demand-induced ischemia in dogs". 1983. *Am. Heart J.* 106:736-50.

Sobel, B. E.: "Diagnostic promise of positron tomography". 1982. *Am. Heart J.* 103: 673-681.

Schelbert, H. R., Phelps, M. E., and Shine, K. I.: "Imaging metabolism and biochemistry—a new look at the heart". 1983. *Am. Heart J.* 105:522-526.

Schelbert, H. R.: "Positron emission tomography: Assessment of myocardial blood flow and metabolism". 1985 *Circulation* 72: TV122-133.

Sobel, B. E.: "Positron tomography and myocardial metabolism: An overview". 1985 *Circulation* 72: IV22-30.

Schlösser, M., and Zimmermann, S.: "Fluor-olefine durch Fluormenthylenierung von Carbonylverbindungen" 1969. *Synthesis* 1: 75-76.

Sloof, G. W., Visser, F. C., van Lingen, A., Bax, J. J., Eersels, J., Teule, G. J., and Knapp, F. F. Jr.: "Evaluation of heart-to-organ ratios of 123I-BMIPP and the dimethyl-substituted 123I-DMIPP fatty acid analogue in humans" 1997. *Nucl. Med. Commun.* 18(11): 1065-70.

Sokoloff, L., Reivich, M., Kennedy, C., Des Rosiers, M. H., Patlak, C. S., Pettigrew, K. S., Sakurada, O., Shinohara, M.: "The [$^{14}$C]-deoxyglucose method for the measurement of local cerebral glucose utilization: Theory, procedure, and normal values in the conscious and anesthetized albino rat" 1977. *J. Neurochem.* 28: 879-916.

Sorenson, J. A., and Phelps, M. E. Physics in nuclear medicine, 2nd ed. Philadelphia: W.B. Saunders; 1987.

Stork, G., and Zhao, K.: "A Stereoselective Synthesis of (Z)-1-Iodo-1-Alkenes" 1989. *Tetrahedron Lett.* 30: 2173-2174.

Stork, G., and Zhao, K.: "Total Syntheses of (−)-Histrionicotoxin and (−)-Histrionicotoxin 235A" 1990. *J. Am. Chem. Soc.* 112: 5875-5876.

Ter-Pogossian, M. M., Klein, M. S., Markham, J., Roberts, R., and Sobel, B. E.: "Regional assessment of myocardial metabolic integrity in vivo by positron-emission tomography with 11C-labeled palmitate". 1980. *Circulation* 61:242-255.

Van der Wall, E. E., Heidendal, G. A., den Hollander, W., Westera, G., and Roos, J. P.: "I-123 labeled hexadecenoic acid in comparison with thallium-201 for myocardial imaging in coronary heart disease. A preliminary study" 1980. *Eur. J. Nucl. Med.* 5(5): 401-5.

Visser, F. C., van Eenige, M. J., Westera, G., Den Hollander, W., Duwel, C. M., van der Wall, E. E., Heidendal, G. A., and Roos, J. P.: "Metabolic fate of radioiodinated heptadecanoic acid in the normal canine heart" 1985. *Circulation* 72(3): 565-71.

Weiss, E. S., Hoffman, E. J., Phelps, M. E., Welch, M. J., Henry, P. D., Ter-Pogossian, M. M., and Sobel B E.: "External detection and visualization of myocardial ischemia with $^{11}$C-substrate in vitro and in vivo". 1969. *Circulation* 19:25-32.

Weiss, E. S., Ahmed, S. A., Welch, M. J., Williamson, J. R., Ter-Pogossian, M. M., and Sobel, B. E.: "Quantification of infarction in cross sections of canine myocardium in vivo with positron emission transaxial tomography and 11C-palmitate". 1977. *Circulation* 55: 66-73.

Wieler, H., Kaiser, K. P., Frank, J., Kuikka, J. T., Ladwein, K., and Winkens, A.: "Standardized non-invasive assessment of myocardial free fatty acid kinetics by means of 15-(paraiodo-phenyl) pentadecanoic acid ($^{123}$I-pPPA) scintigraphy: I. Method" 1990. *Nuc. Med. Commun.* 11: 865-878.

Yamamichi, Y., Kusuoka, H., Morishita, K., Shirakami, Y., Kurami, M., Okano, K., Itoh, O., and Nishimura, T.: "Metabolism of iodine-123-BMIPP in perfused rat hearts" 1995. *J. Nucl. Med.* 36:1042-10.

What is claimed is:

1. A method of measuring blood flow in a subject comprising the following steps:
   localizing to a tissue of interest a detectable amount of a radioactively labeled compound selected from the group consisting of:
   [$^{18}$F]-9-fluoro-3,4-cyclopropylheptadecanoic acid;
   [$^{18}$F]-9-fluoro-3,4-cyclobutylheptadecanoic acid;
   [$^{18}$F]-9-fluoro-3,4-cyclopentylheptadecanoic acid;
   [$^{18}$F]-17-(4-fluorophenyl)-3,4-cyclopropyl-heptadecanoic acid; and
   [$^{18}$F]-17-(4-fluorophenyl)-3,4-cyclobutyl-heptadecanoic acid;
   b) detecting a signal from said radioactively labeled compound in said tissue of interest within about 1 second to about 10 minutes;
   c) imaging said tissue of interest, and;
   d) determining the rate of blood flow in said tissue of interest.

2. The method of claim 1, wherein the amount of said radioactively labeled compound is 0.1 mCi to about 25 mCi.

3. The method of claim 1, wherein the amount of said radioactively labeled compound is 1 mCi to about 5 mCi.

4. The method of claim 1, wherein said radioactively labeled compound is detected within 1 minute to about 5 minutes after administration.

5. The method of claim 1, wherein said radioactively labeled compound is administered with a second radioactive tracer.

6. The method of claim 5, wherein the second radioactive tracer is selected from the group consisting of $^{13}$N-Ammonia, $^{57}$Co-Cyanocobalamin, $^{59}$Fe-Ferrous Citrate, $^{18}$F-Fluorodeoxyglucose, $^{69}$Ga-Gallium Citrate, $^{111}$In-Indium Oxyquinoline, $^{111}$In-Indium Pentetate, $^{111}$In-Indium Pentetreotide, $^{111}$In-Indium Satumomab Pendetide, Radioiodinated Iobenguane, $^{123}$I-Iodohippurate Sodium, $^{131}$I-Iodohippurate Sodium, $^{123}$I-Iofetamine, $^{125}$I-Iothalamate Sodium, $^{81}$Krypton, $^{11}$C-Methionine, RadioiodinatedAlbumin, $^{82}$Rubidium, Sodium $^{51}$Chromate, Sodium $^{18}$Fluoride, Sodium $^{123}$Iodide, Sodium $^{131}$Iodide, Sodium $^{99m}$-Pertechnetate, $^{99m}$Tc-Albumin, $^{99m}$Tc-Albumin (Aggregated), $^{99m}$Tc-Albumin (Colloidal), $^{99m}$Tc Arcitumomab, $^{99m}$Tc-Bicisate, $^{99m}$Tc-Disofenin, $^{99m}$Tc-Exametazime, $^{99m}$Tc-Gluceptate, $^{99m}$Tc-Lidofenin, $^{99m}$Tc-Mebrofenin, $^{99m}$Tc-Medronate, $^{99m}$Tc Mertiatide, $^{99m}$Tc-Nofetumomab Merpentan, $^{99m}$Tc-Oxidronate, $^{99m}$Tc-Pentetate, $^{99m}$Tc-Pyrophosphate, $^{99m}$Tc-(Pyro- and trimeta-) Phosphates, $^{99m}$Tc-Sestamibi, $^{99m}$Tc-Succimer, $^{99m}$Tc-Sulfur (Colloidal), $^{99m}$Tc-Teboroxime, $^{99m}$Tc-Tetrofosmin, $^{201}$Thallous Chloride, $^{127}$Xenon and $^{133}$Xenon.

7. The method of claim 1, wherein the tissue of interest is cardiac tissue.

8. The method of claim 1, wherein the cardiac tissue is diseased.

9. The method of claim 8, wherein the disease is selected from the group consisting of acute myocardial infarction, unstable angina, chronic ischemic heart disease, coronary artery disease, myocarditis, cardiomyopathies, congenital heart diseases, hypertensive heart disease, post-transplant heart disease, allograft vasculopathies, and valvular heart disease.

10. The method of claim 7, wherein the cardiac tissue is normal.

11. The method of claim 7, wherein the cardiac tissue is subjected to stress.

12. The method of claim 11, wherein the stress is induced by exercise.

13. The method of claim 11, wherein the stress is induced by pharmacological agents.

14. The method of claim 1, wherein the tissue of interest is not cardiac tissue.

15. The method of claim 14, wherein the tissue of interest is selected from the group consisting of brain, liver, bone, spleen, lung, blood, kidney, gastrointestinal, muscle, and adrenal tissue.

16. The method of claim 14, wherein the tissue is diseased.

17. The method of claim 14, wherein the tissue is normal.

18. The method of claim 16, wherein the disease is selected from the group consisting of abscess and infection; biliary tract blockage; blood volume studies; blood vessel diseases; blood vessel diseases of the brain; bone diseases; bone marrow diseases; brain diseases and tumors; cancer and neoplasms; colorectal disease; diabetes; disorders of iron metabolism and absorption; impaired flow of cerebrospinal fluid in brain; kidney diseases; lipid diseases; liver diseases; lung diseases; parathyroid diseases; parathyroid cancer; pernicious anemia; improper absorption of vitamin B12 from intestines; red blood cell diseases; salivary gland diseases; spleen diseases; stomach disorders and intestinal bleeding; tear duct blockage; thyroid diseases; thyroid cancer; urinary bladder diseases.

19. The method of claim 1, wherein the radioactively labeled compound is detected by positron emission.

20. The method of claim 1, wherein the radioactively labeled compound is detected by photon emission.

21. The method of claim 1, further comprising the step of retaining the radioactively labeled compound, or a metabolic derivative thereof, in the tissue by reducing transport and back-diffusion of the radioactively labeled compound.

22. The method of claim 1, further comprising the step of retaining the radioactively labeled compound, or a metabolic derivative thereof, in the tissue by reducing ketoacetyl elimination of the radioactively labeled compound.

* * * * *